US012685732B2

(12) United States Patent
Park et al.

(10) Patent No.: US 12,685,732 B2
(45) Date of Patent: Jul. 21, 2026

(54) COMPOSITION FOR IMPROVING, PREVENTING OR TREATING MUSCULAR DISORDERS INCLUDING SULFONAMIDE-BASED COMPOUNDS

(71) Applicant: The Industry & Academic Cooperation in Chungnam National University (IAC), Daejeon (KR)

(72) Inventors: Jongsun Park, Daejeon (KR); Jisoo Park, Chungcheongnam-do (KR); Hyunji Lee, Daejeon (KR)

(73) Assignee: The Industry & Academic Cooperation in Chungnam National University (IAC), Daejeon (KR)

( * ) Notice: Subject to any disclaimer, the term of this patent is extended or adjusted under 35 U.S.C. 154(b) by 547 days.

(21) Appl. No.: 18/296,796

(22) Filed: Apr. 6, 2023

(65) Prior Publication Data

US 2023/0321096 A1 Oct. 12, 2023

(30) Foreign Application Priority Data

Apr. 7, 2022 (KR) ........................ 10-2022-0043350
May 13, 2022 (KR) ........................ 10-2022-0058865
Dec. 27, 2022 (KR) ........................ 10-2022-0186355

(51) Int. Cl.
*A61K 31/505* (2006.01)
*A61P 21/00* (2006.01)

(52) U.S. Cl.
CPC ............ *A61K 31/505* (2013.01); *A61P 21/00* (2018.01)

(58) Field of Classification Search
CPC .............................. A61K 31/505; A61P 21/00
USPC .......................................................... 514/49
See application file for complete search history.

(56) References Cited

U.S. PATENT DOCUMENTS

2010/0292306 A1 11/2010 Carlson et al.
2013/0310340 A1* 11/2013 Payan ................ A61K 31/5377 544/323
2016/0158251 A1* 6/2016 Shin ..................... A61K 31/635 514/269

FOREIGN PATENT DOCUMENTS

| | | | |
|---|---|---|---|
| JP | H08512055 | A | 12/1996 |
| KR | 20160069802 | A | 6/2016 |
| WO | 1992014456 | A1 | 9/1992 |
| WO | 1995001096 | A1 | 1/1995 |
| WO | 2006127930 | A2 | 11/2006 |
| WO | 2013127917 | A1 | 9/2013 |
| WO | 2016061509 | A1 | 4/2016 |

OTHER PUBLICATIONS

Chacon-Cabrera et al., "Pharmacological strategies in lung cancer-induced cachexia: effects on muscle proteolysis, autophagy, structure, and weakness," J Cell Physiol. 229(11):1660-72 (2014).
Chitti et al., "Repurposing of Antibiotic Sulfisoxazole Inhibits Lipolysis in Pre-Clinical Model of Cancer-Associated Cachexia," Biology (Basel) 10(8):700 (2021).
Omelchenko et al., "Body composition in woman with rheumatoid arthritis," 2022 IEEE International Multi-Conference on Engineering, Computer and Information Sciences (SIBIRCON) 280-283 (2022).
Widrick et al., "Discovery of Novel Therapeutics for Muscular Dystrophies using Zebrafish Phenotypic Screens," J Neuromuscul Dis. 6(3):271-287 (2019).

* cited by examiner

*Primary Examiner* — Yih-Horng Shiao
(74) *Attorney, Agent, or Firm* — MEDLER FERRO WOODHOUSE & MILLS PLLC

(57) ABSTRACT

Provided is a composition for preventing, improving, or treating muscular disorders including sulfonamide-based compounds or salts thereof. According to the present disclosure, the sulfonamide-based compounds or salts thereof may prevent inhibition of differentiation of myoblasts by regulating the expression of PHF20 and YY1. Accordingly, since the composition may prevent or alleviate muscle loss, promote muscle regeneration, and improve muscle exercise function, balance ability, and grip strength recovery ability through increased muscles and changes in ratio of muscle fibers, the composition may be effectively used for therapeutic agents, foods, or feeds for preventing, improving or treating muscle disorders, and improving muscle functions or muscle mass.

6 Claims, 37 Drawing Sheets

[Fig. 1]
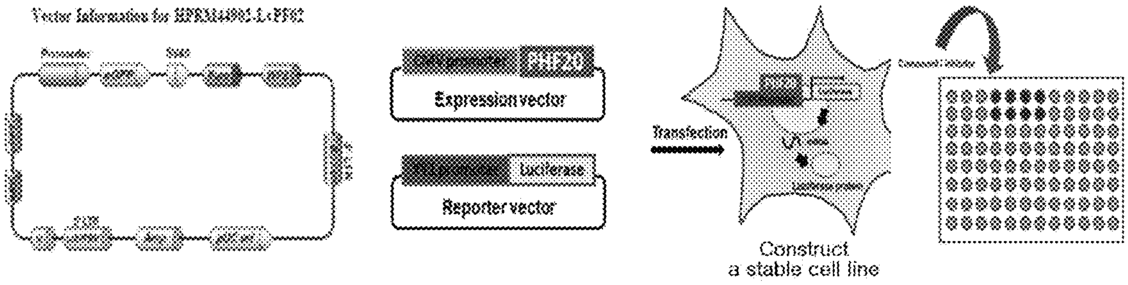
[Fig. 2A]
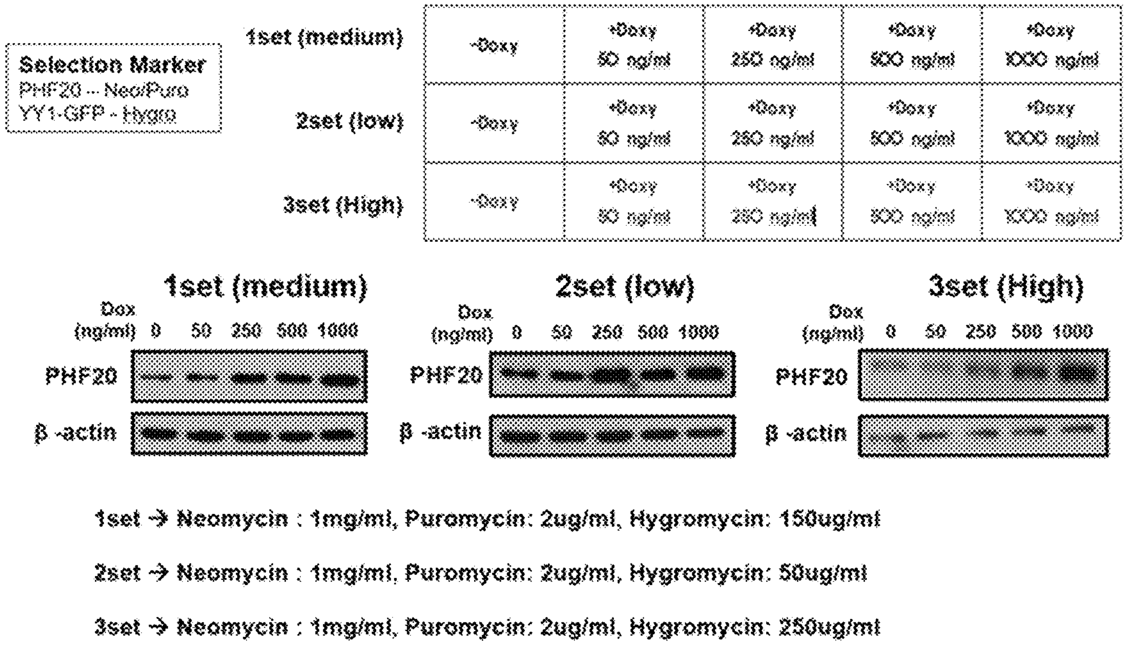

[Fig. 2B]
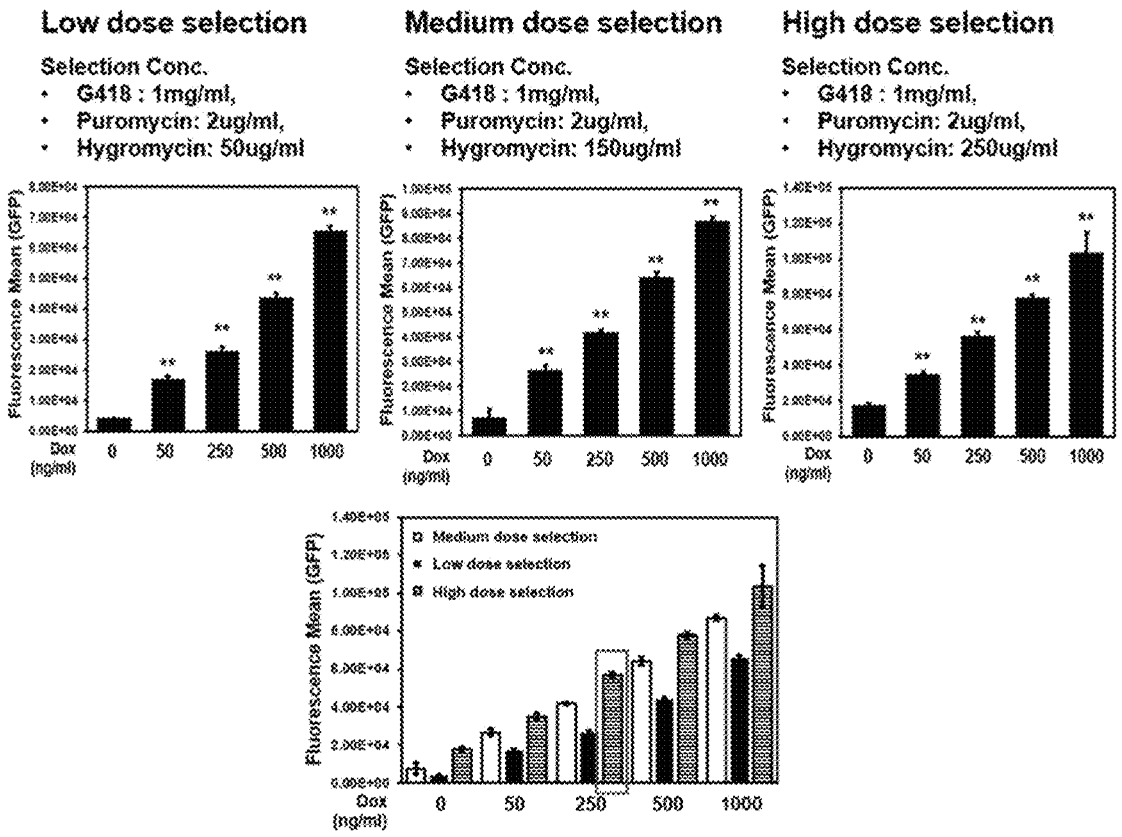

[Fig. 3]
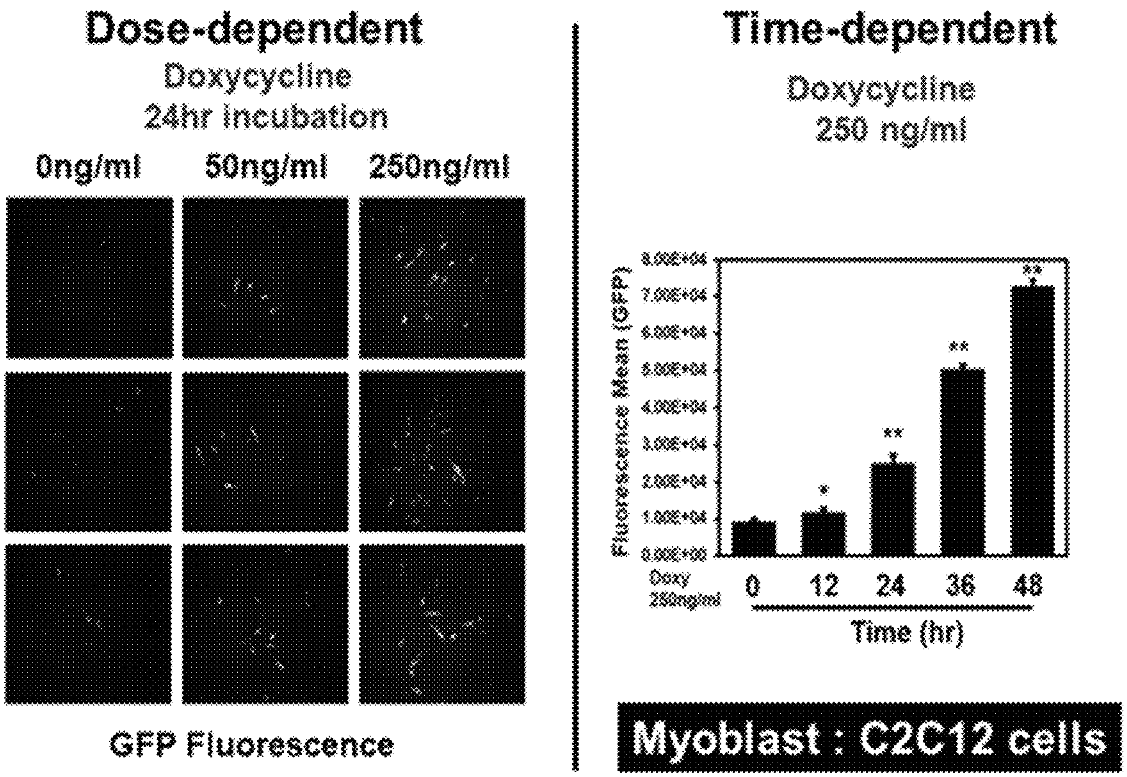

[Fig. 4]
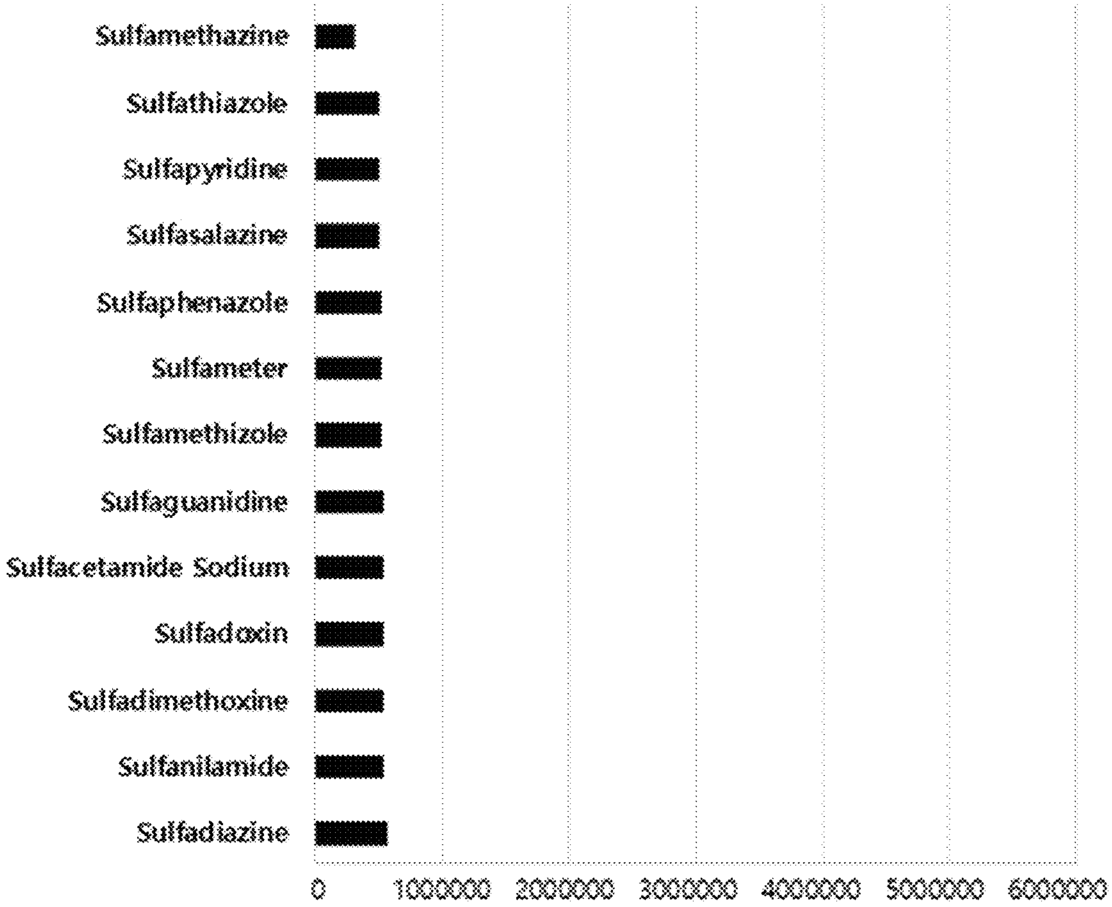

[Fig. 5]
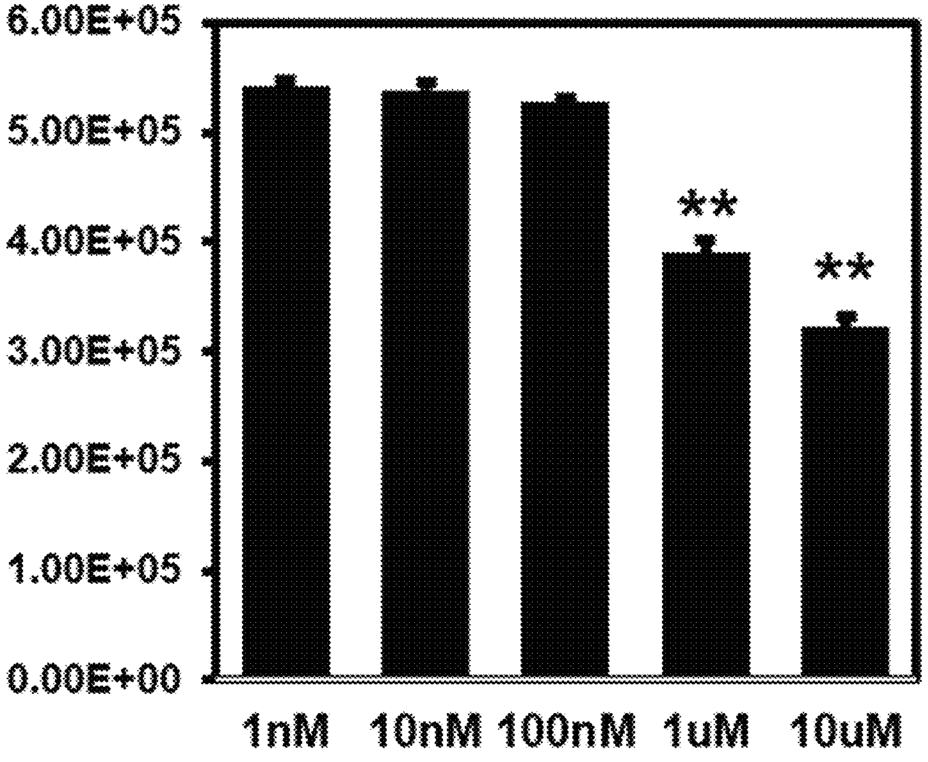

[Fig. 6]
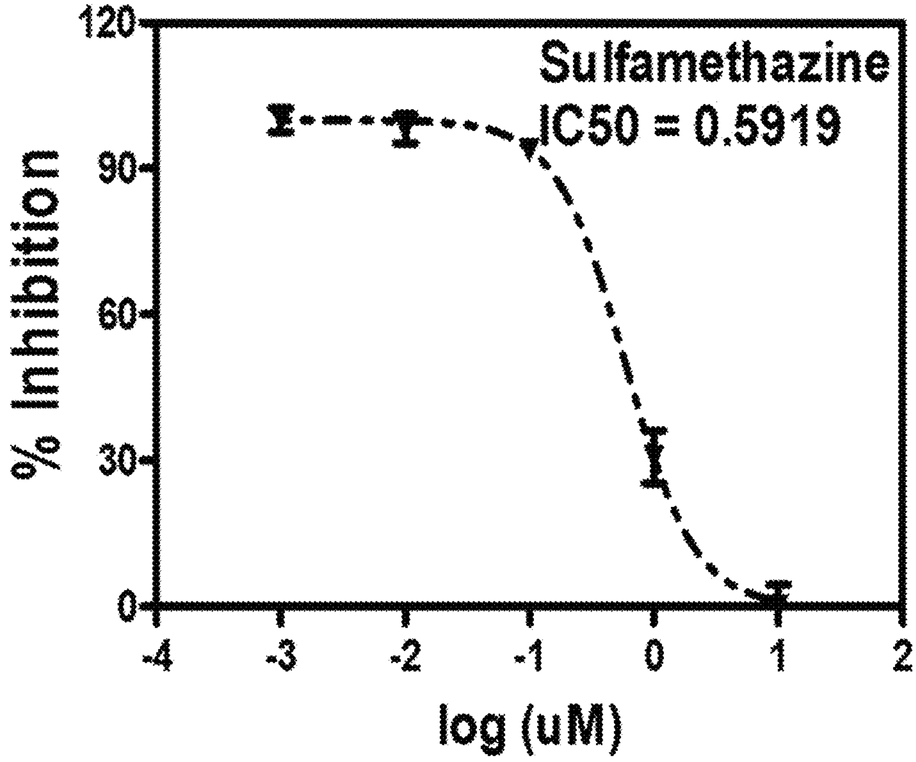

[Fig. 7]
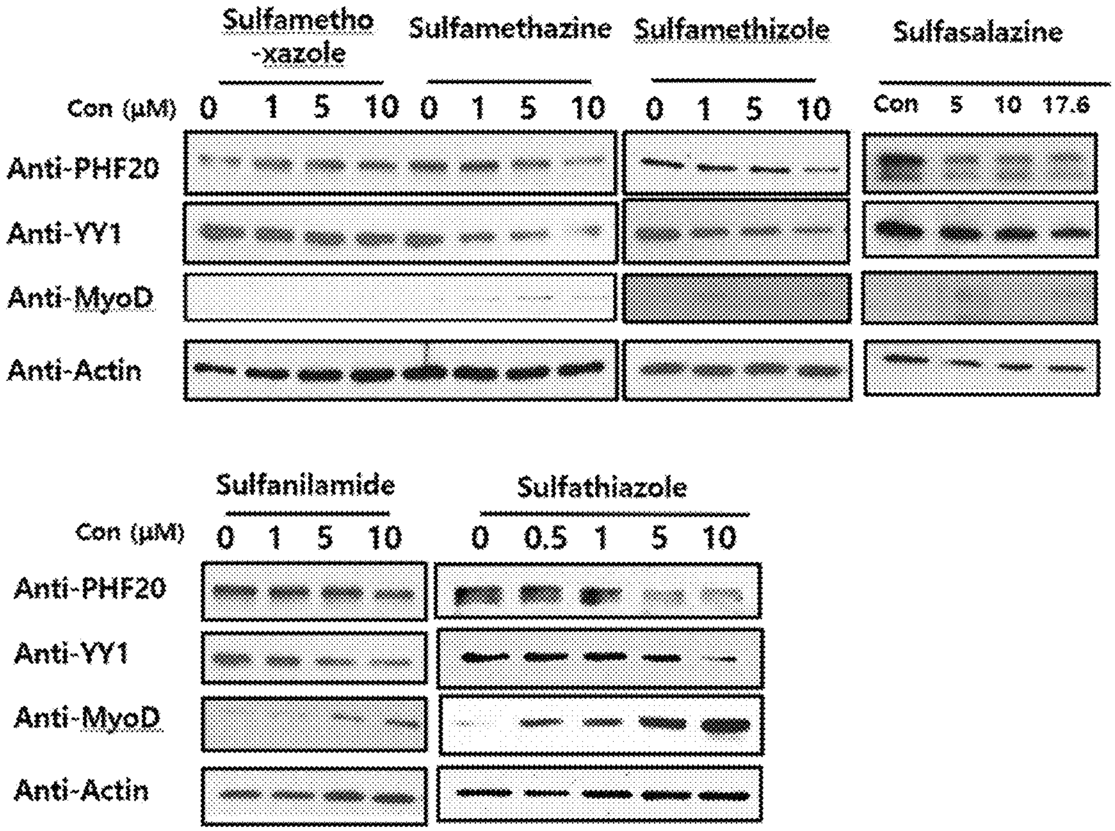

[Fig. 8A]
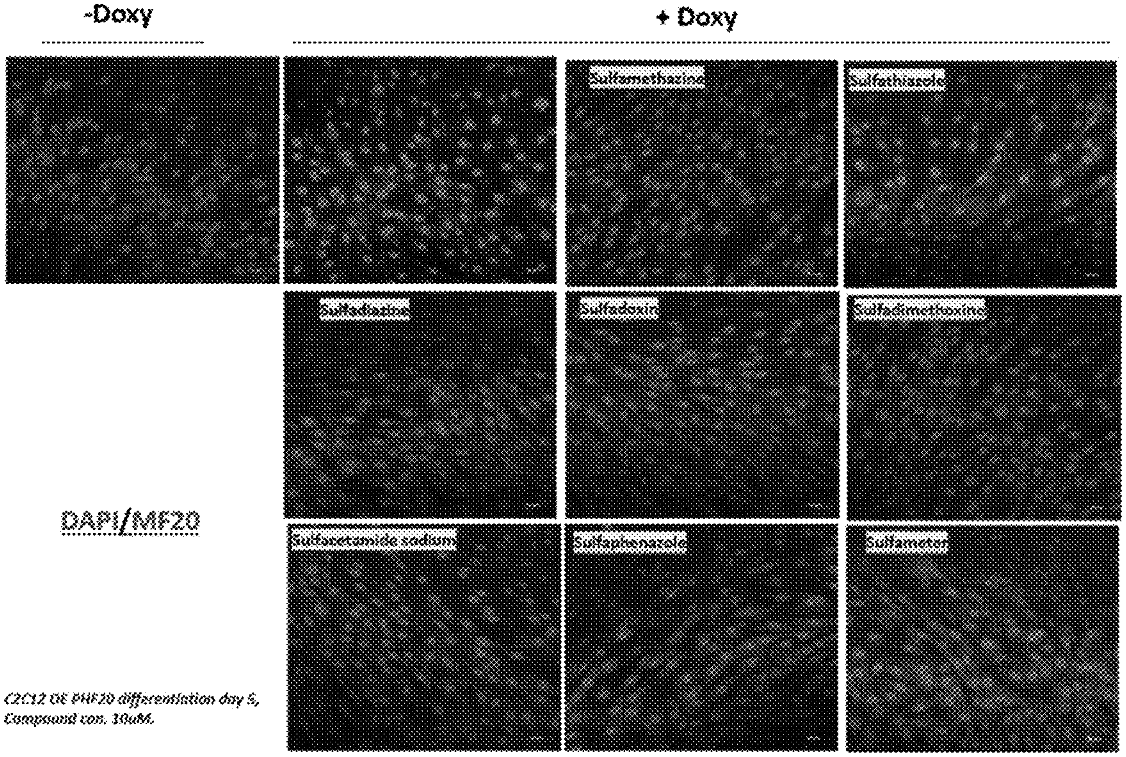
[Fig. 8B]
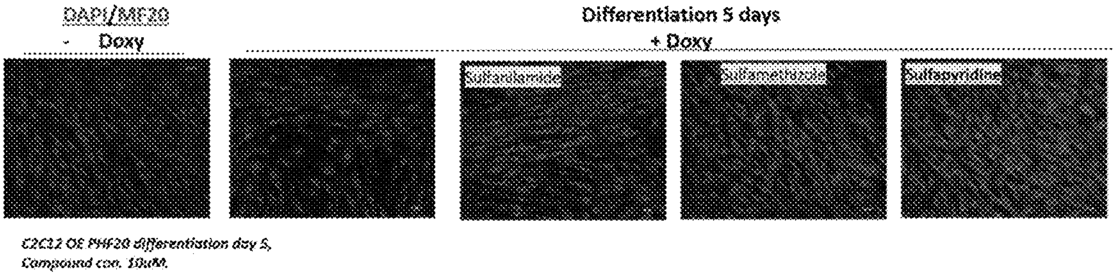

[Fig. 8C]
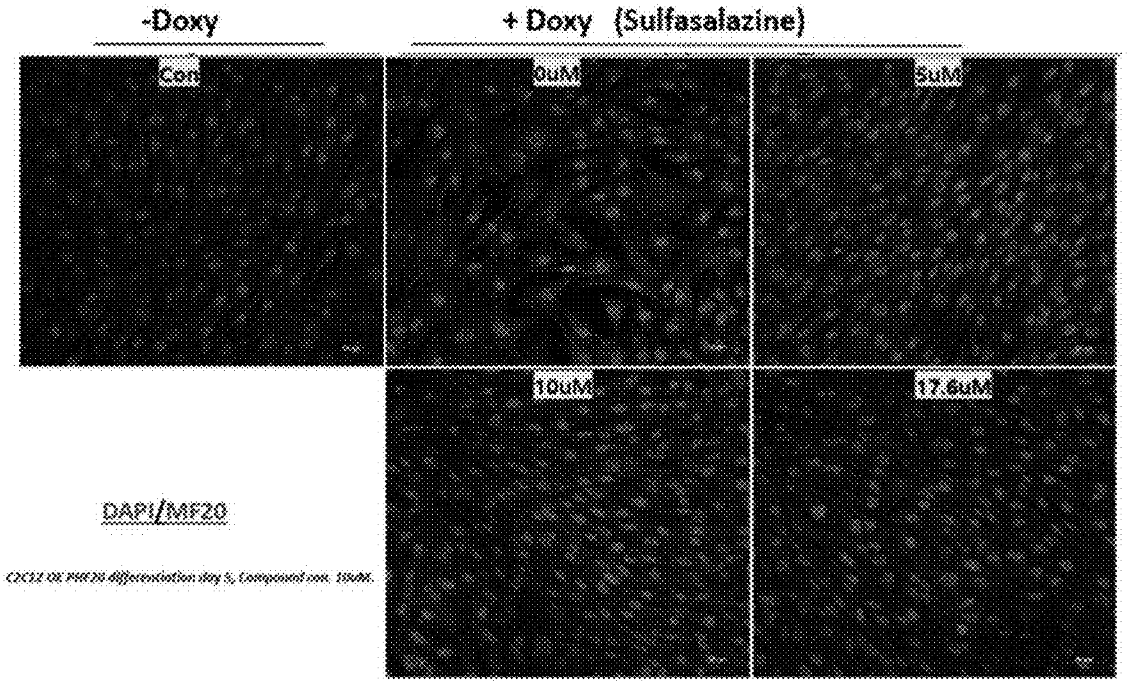
[Fig. 9]
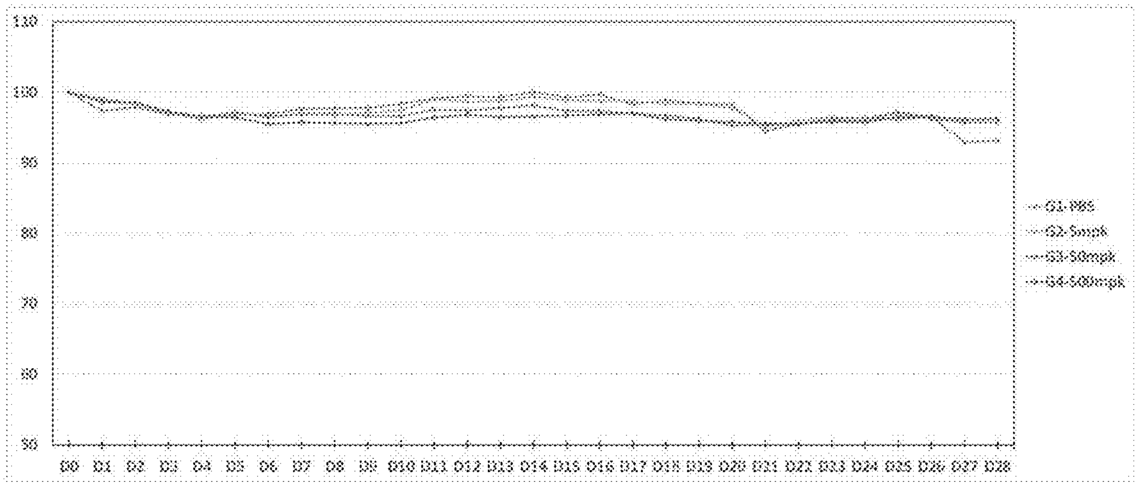

[Fig. 10]
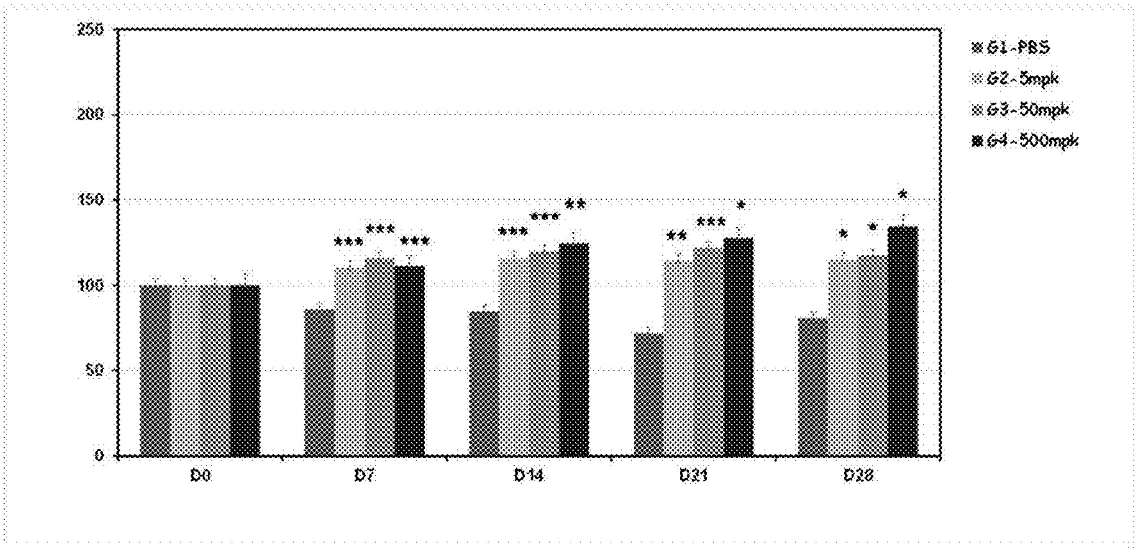
[Fig. 11]
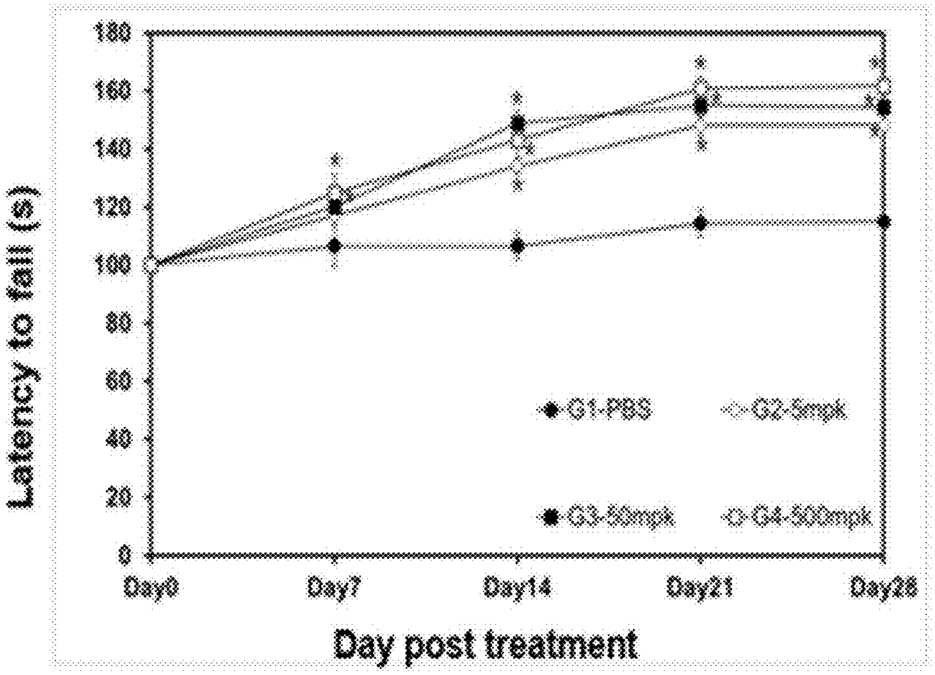

[Fig. 12A]
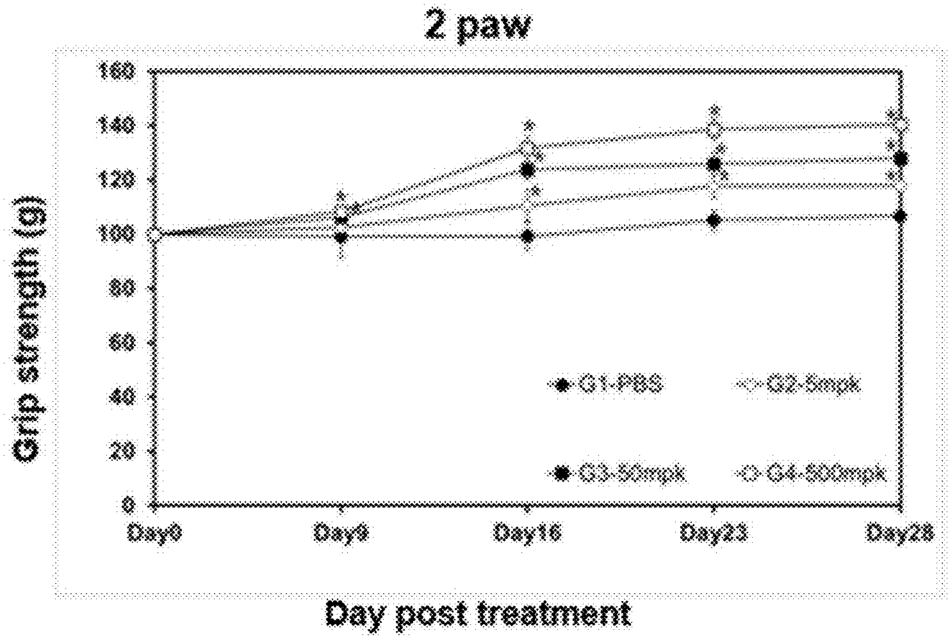
[Fig. 12B]
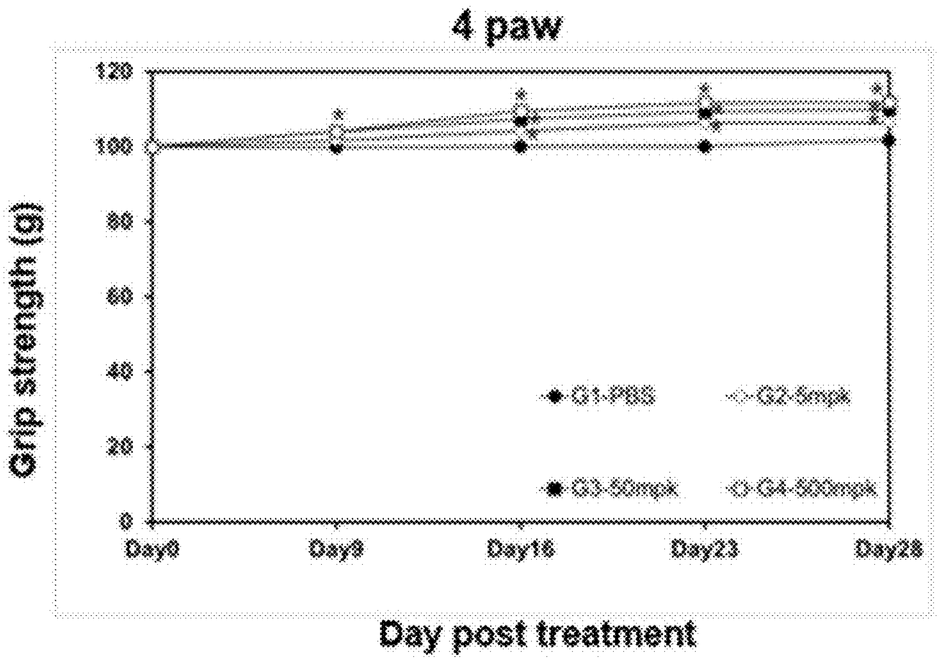

[Fig. 13]
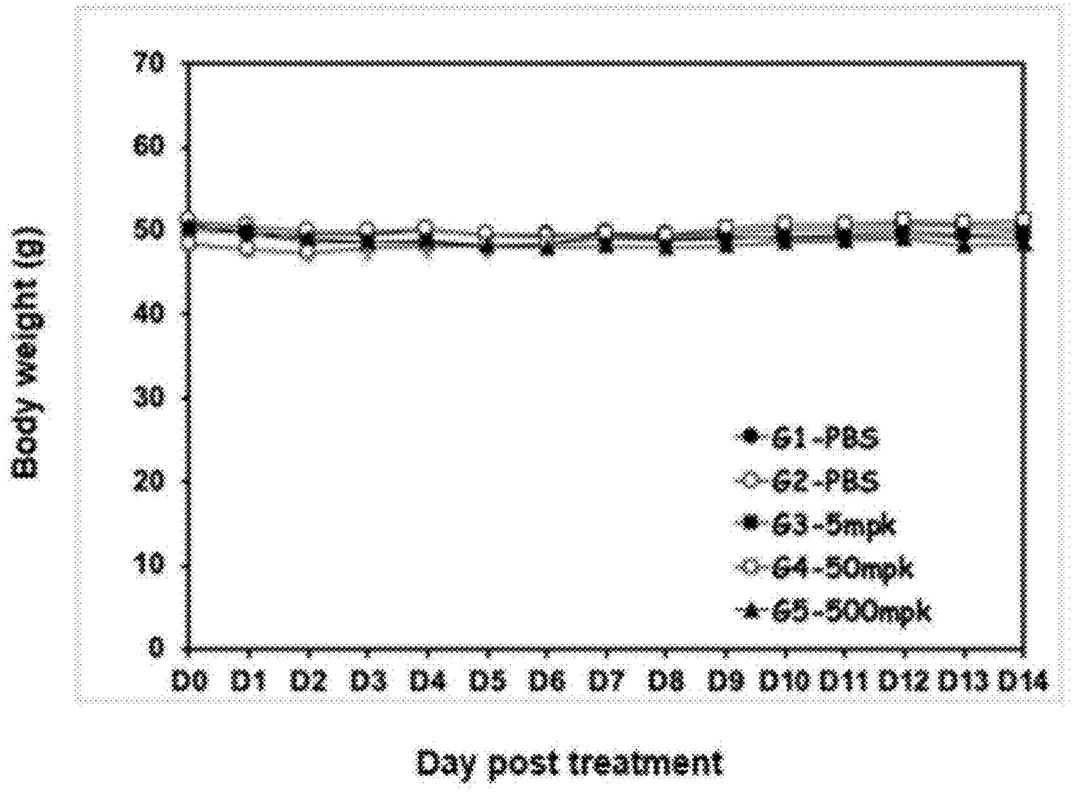
[Fig. 14]
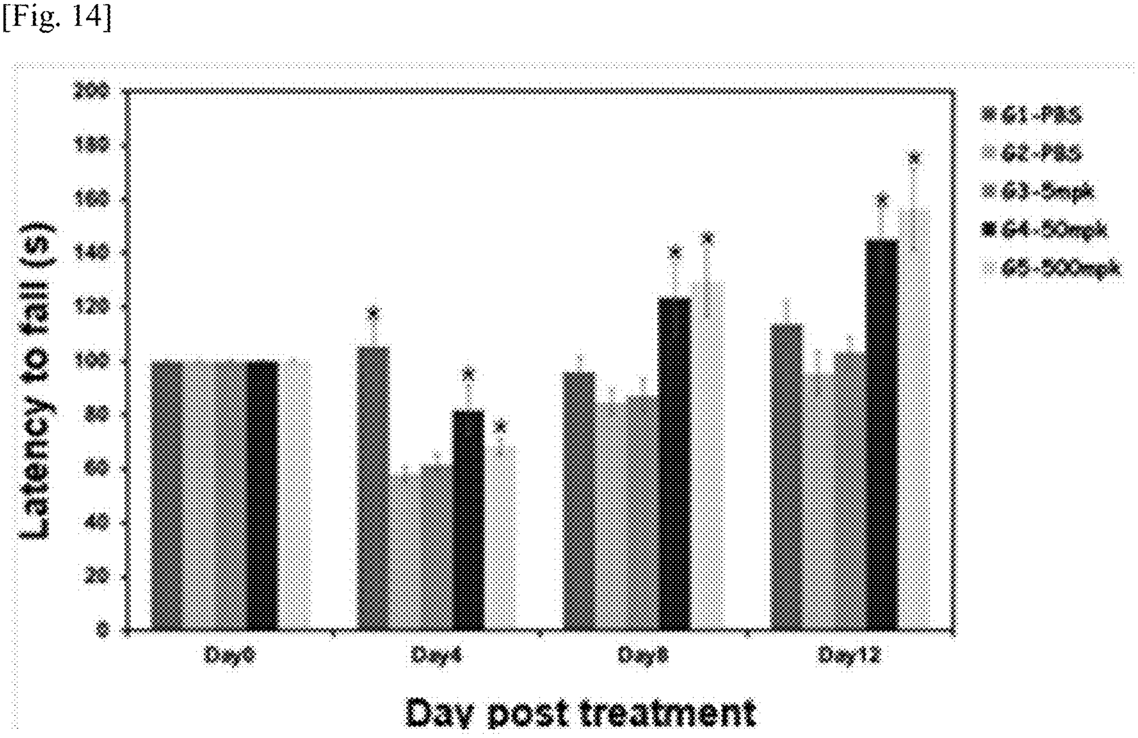

[Fig. 15A]
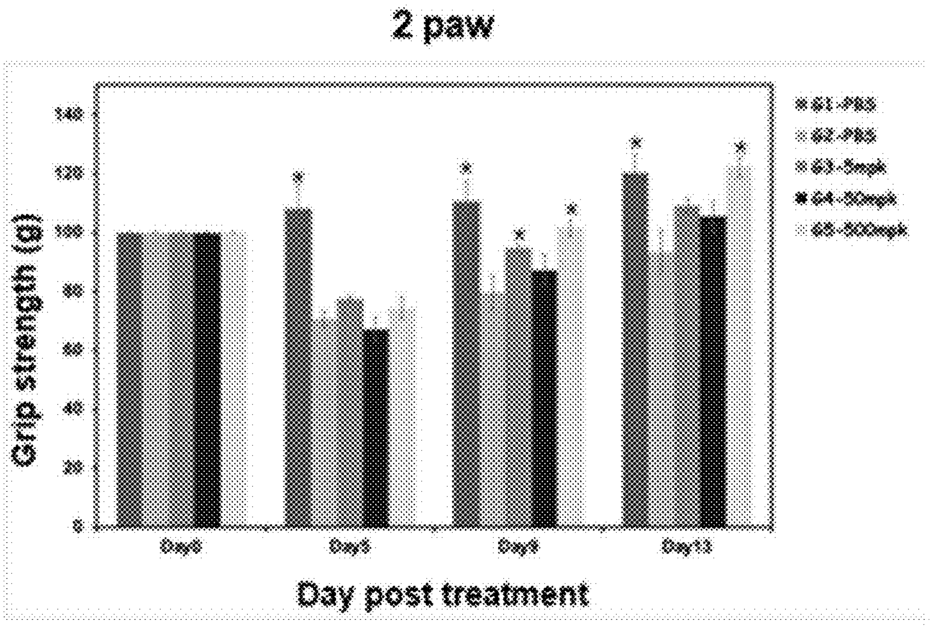
[Fig. 15B]
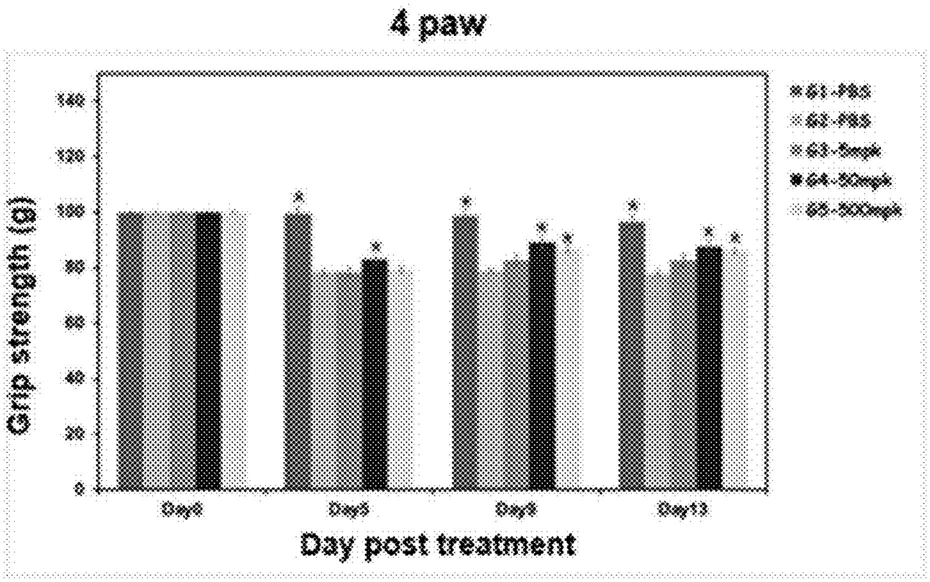

[Fig. 16]
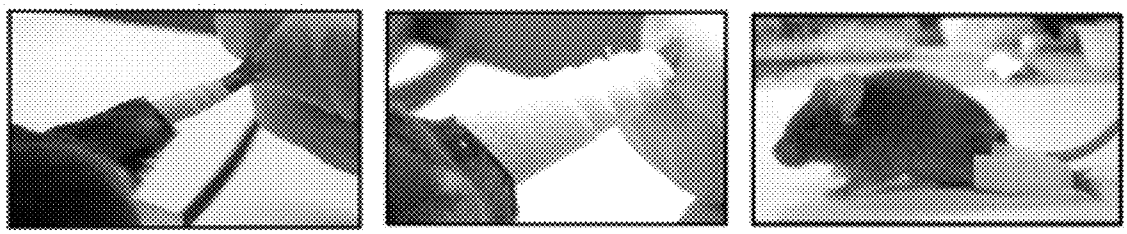
[Fig. 17]
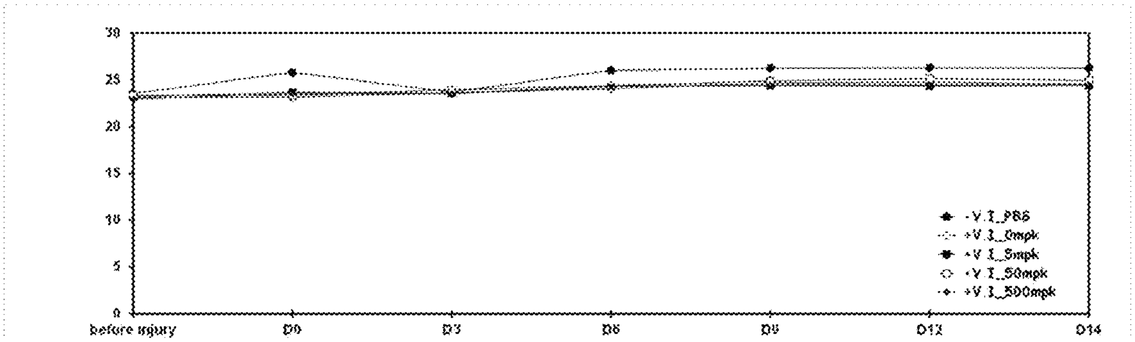
[Fig. 18A]
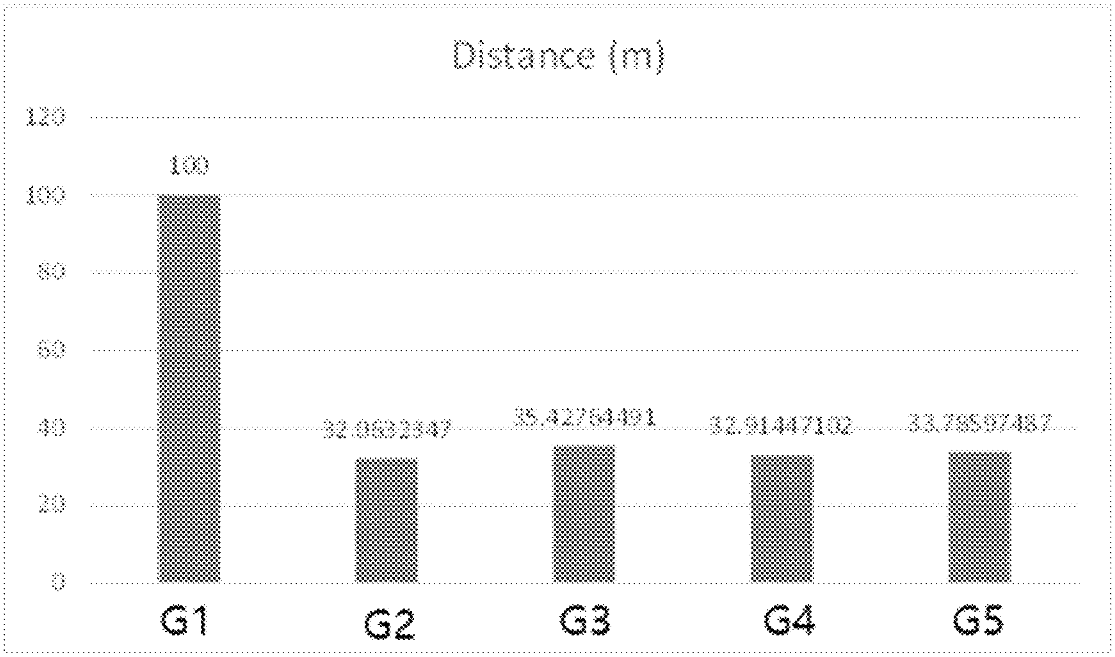

[Fig. 18B]
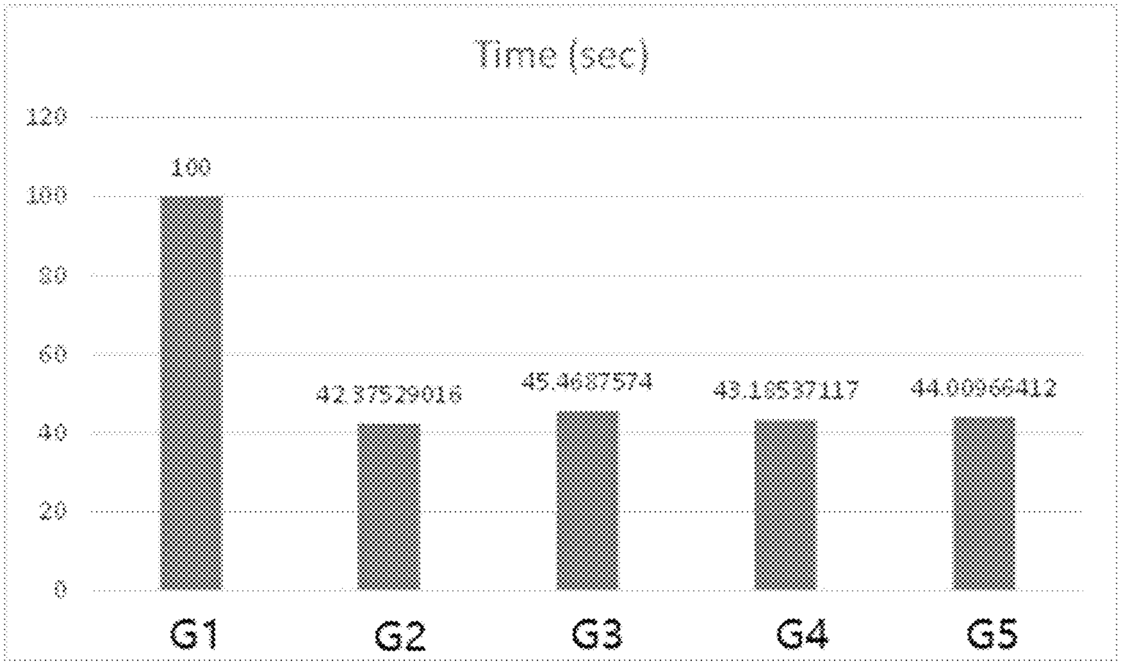
[Fig. 19A]
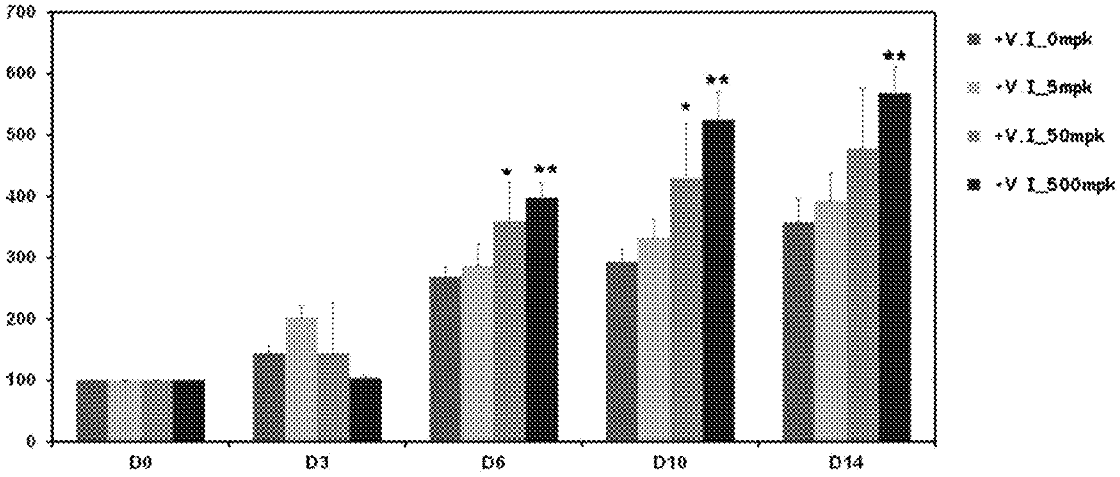

[Fig. 19B]
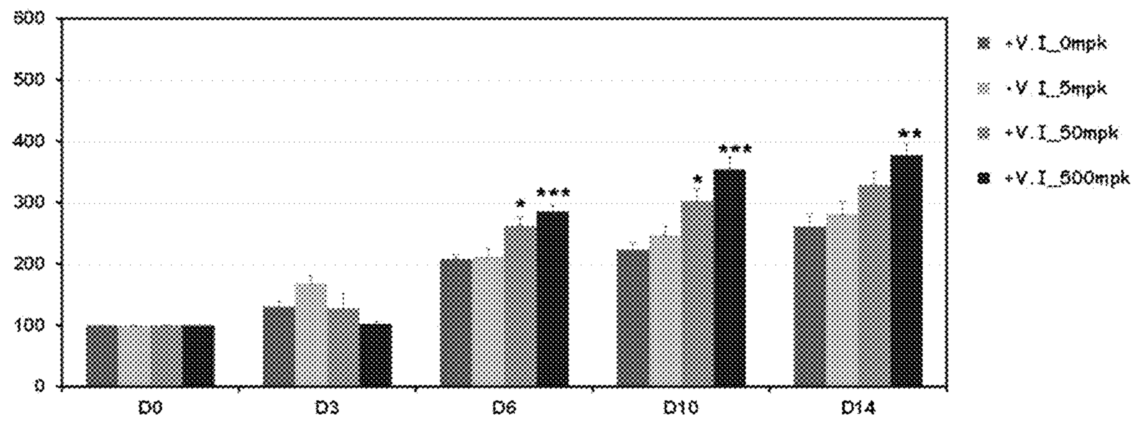
[Fig. 20]
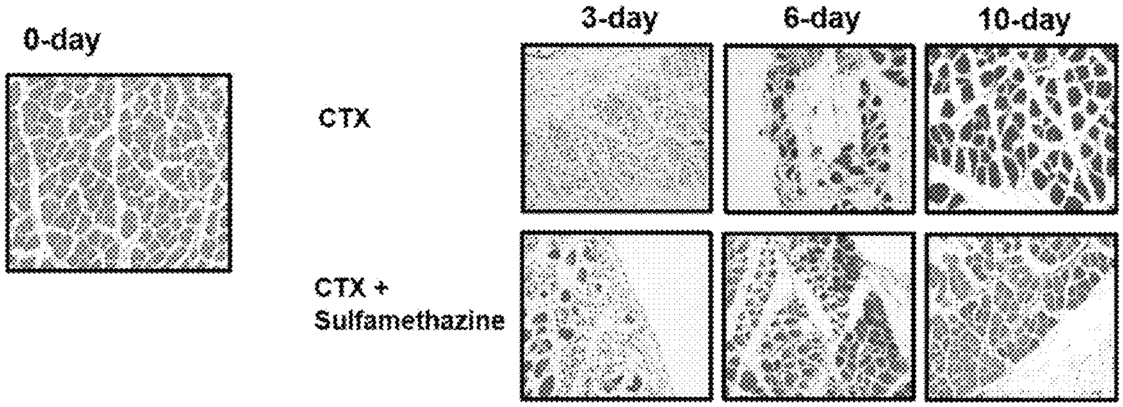
[Fig. 21]
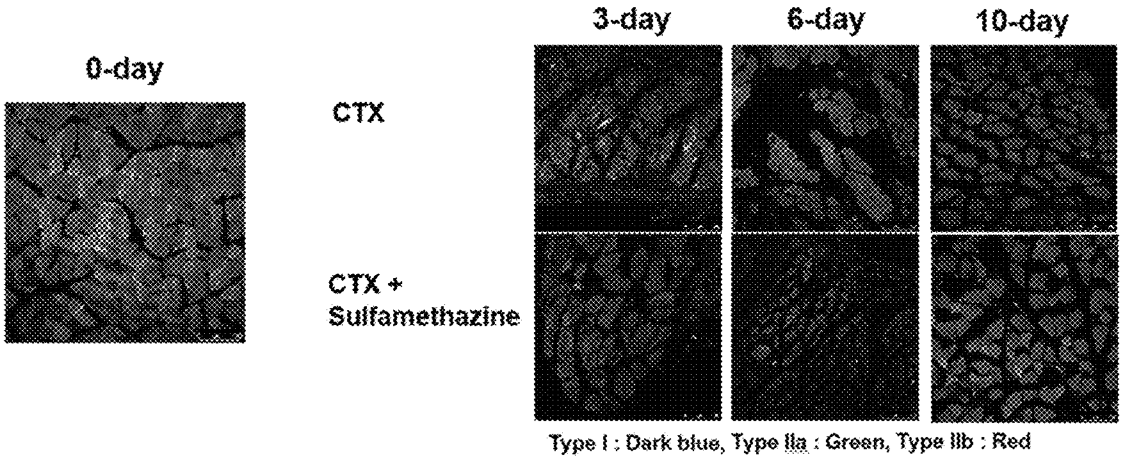

[Fig. 22]
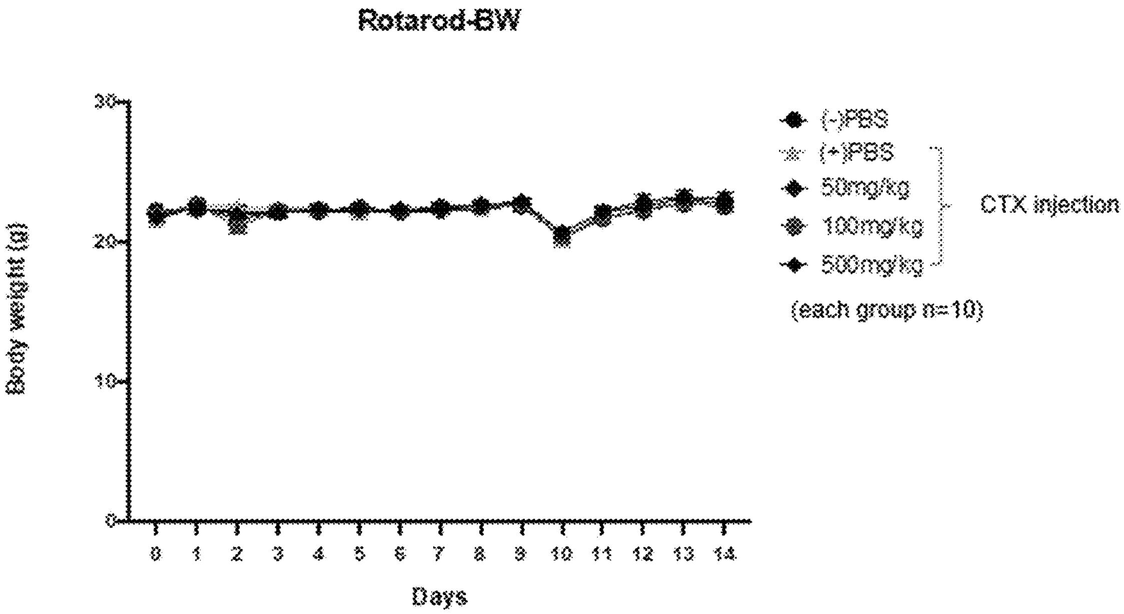
[Fig. 23]
| 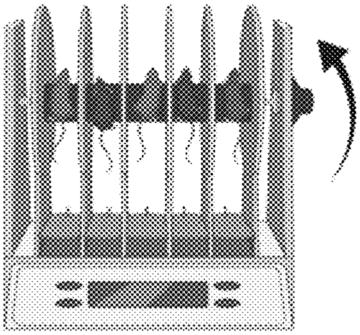 | Constant test | Acceleration |
| --- | --- | --- |
| | 4 rpm in 30 second (mouse standing) | 4 ~ 40 rpm in 300 second (until mouse fall down) |
| | - Wash with 50%EtOH<br>- Interval 15 min | |

[Fig. 24]
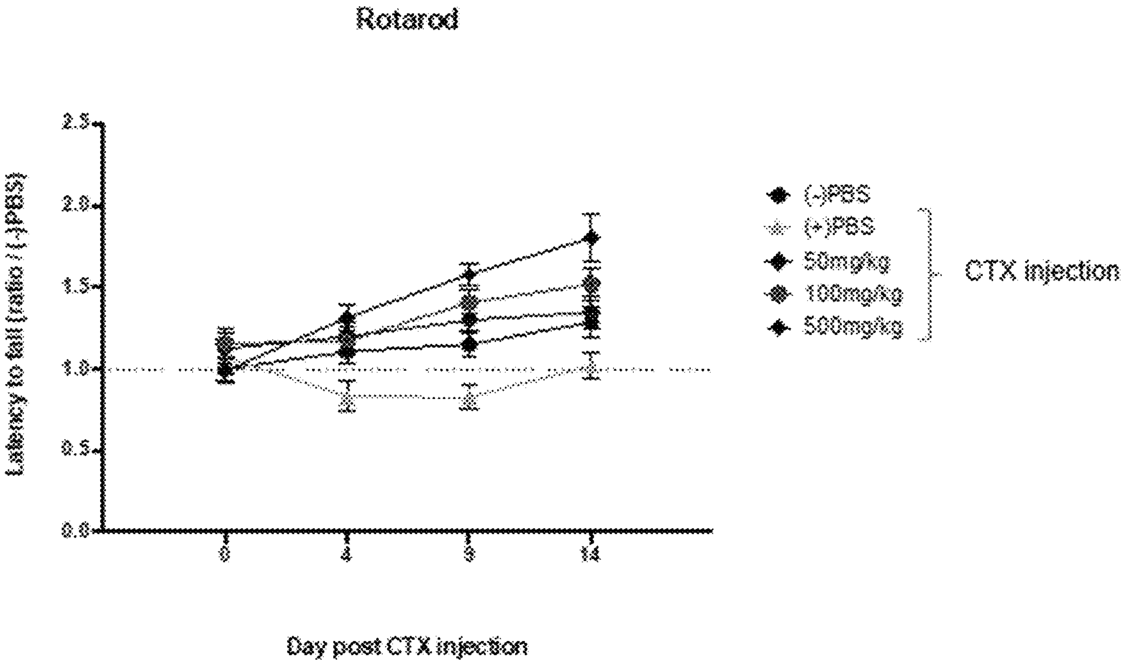
[Fig. 25]
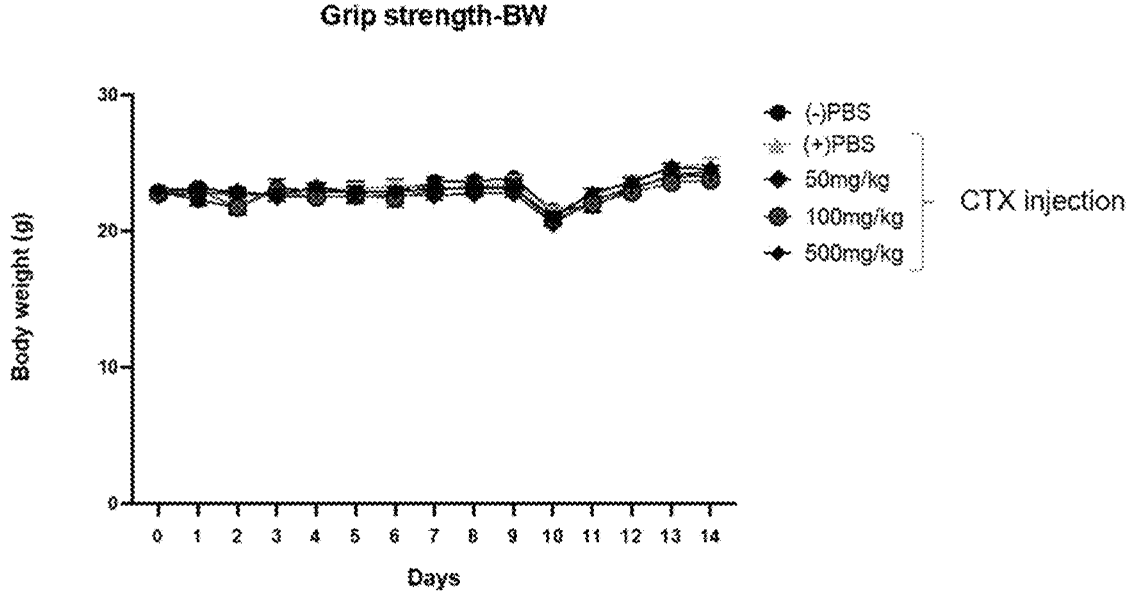

[Fig. 26A]
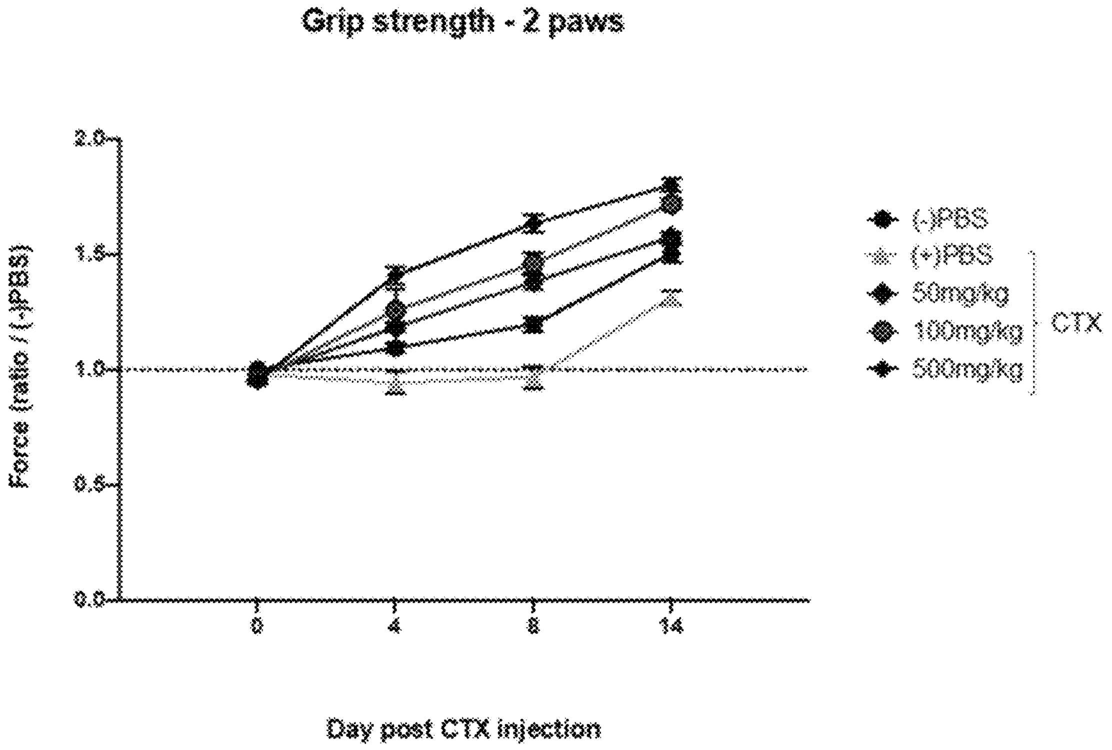

[Fig. 26B]
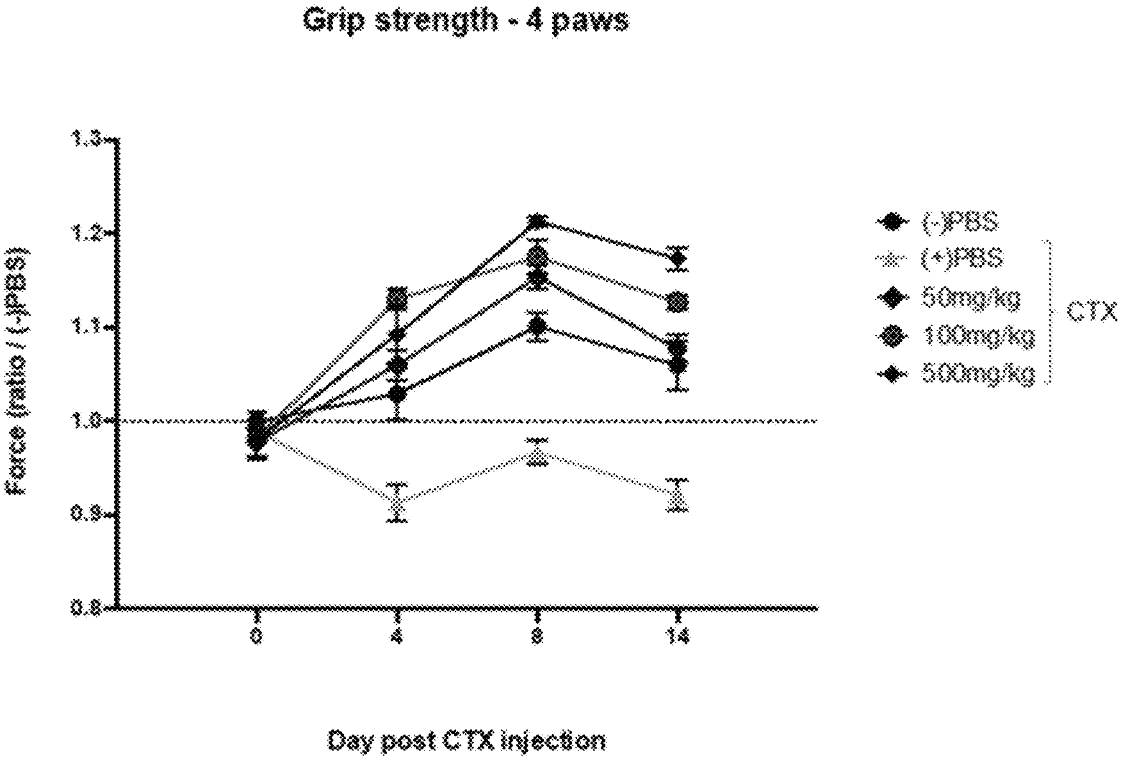
[Fig. 27A]
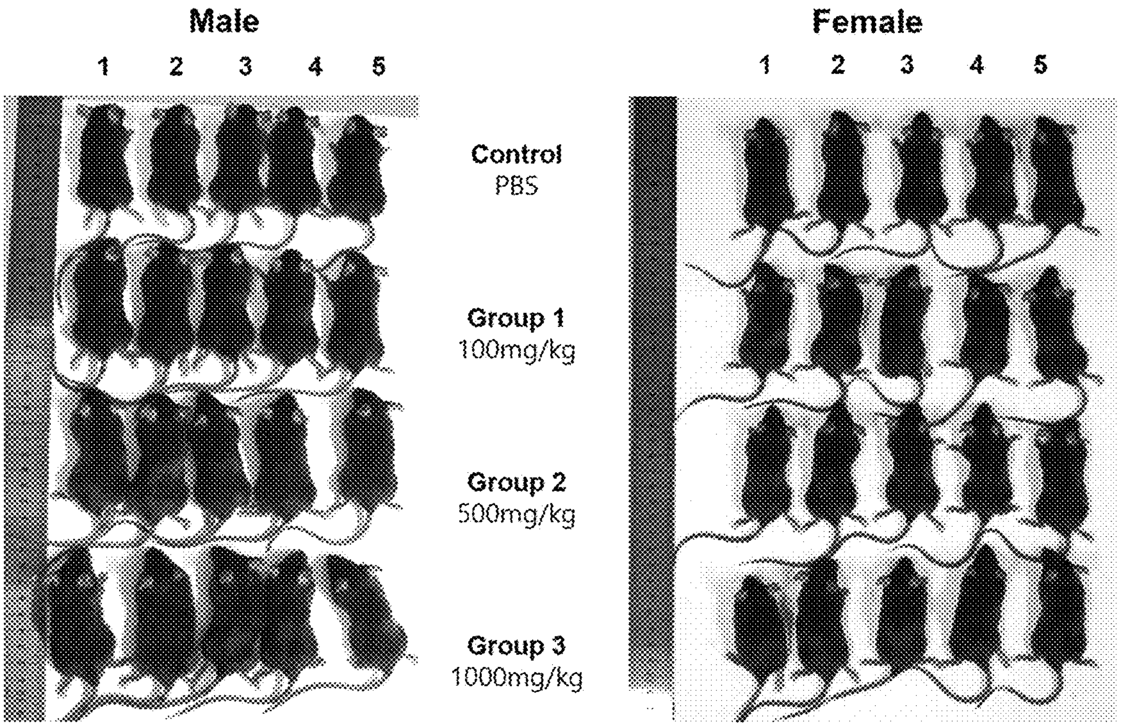

[Fig. 27B]
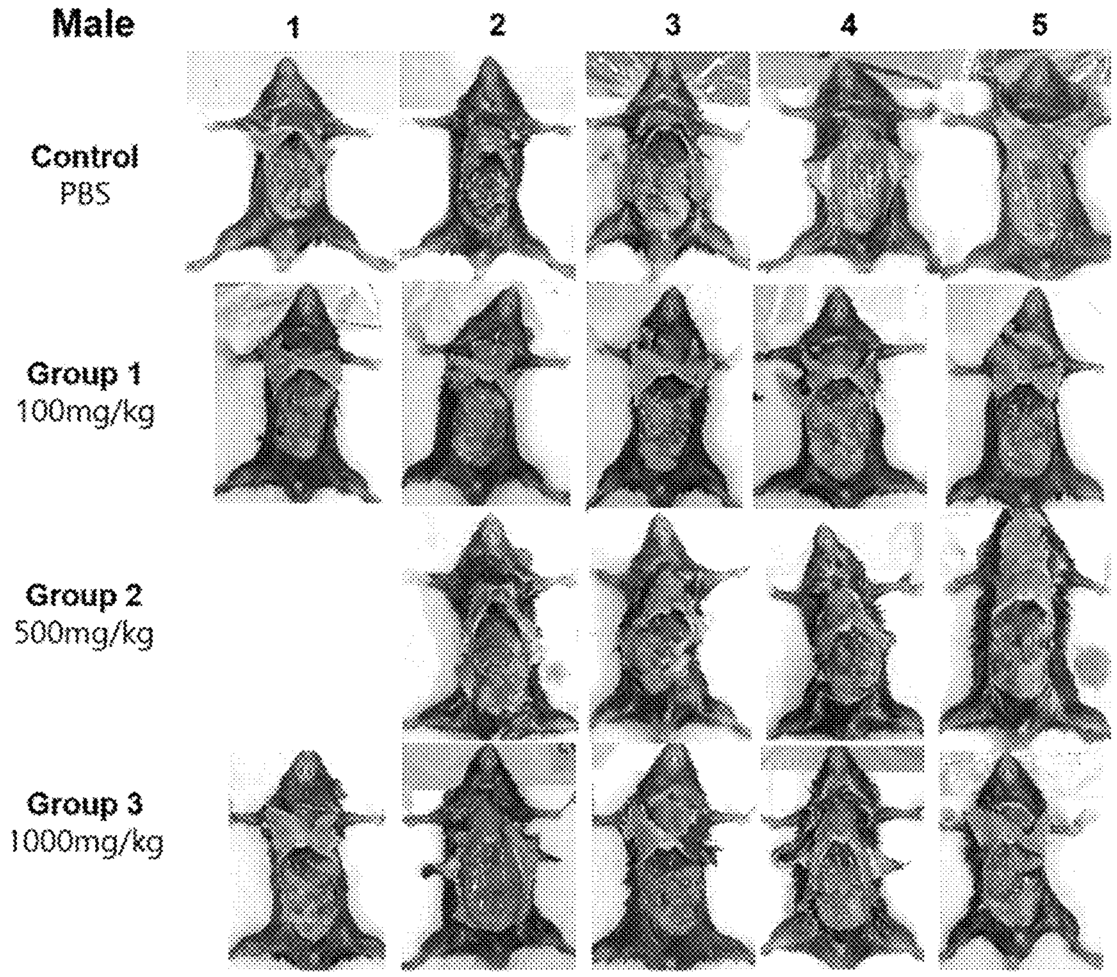

[Fig. 27C]
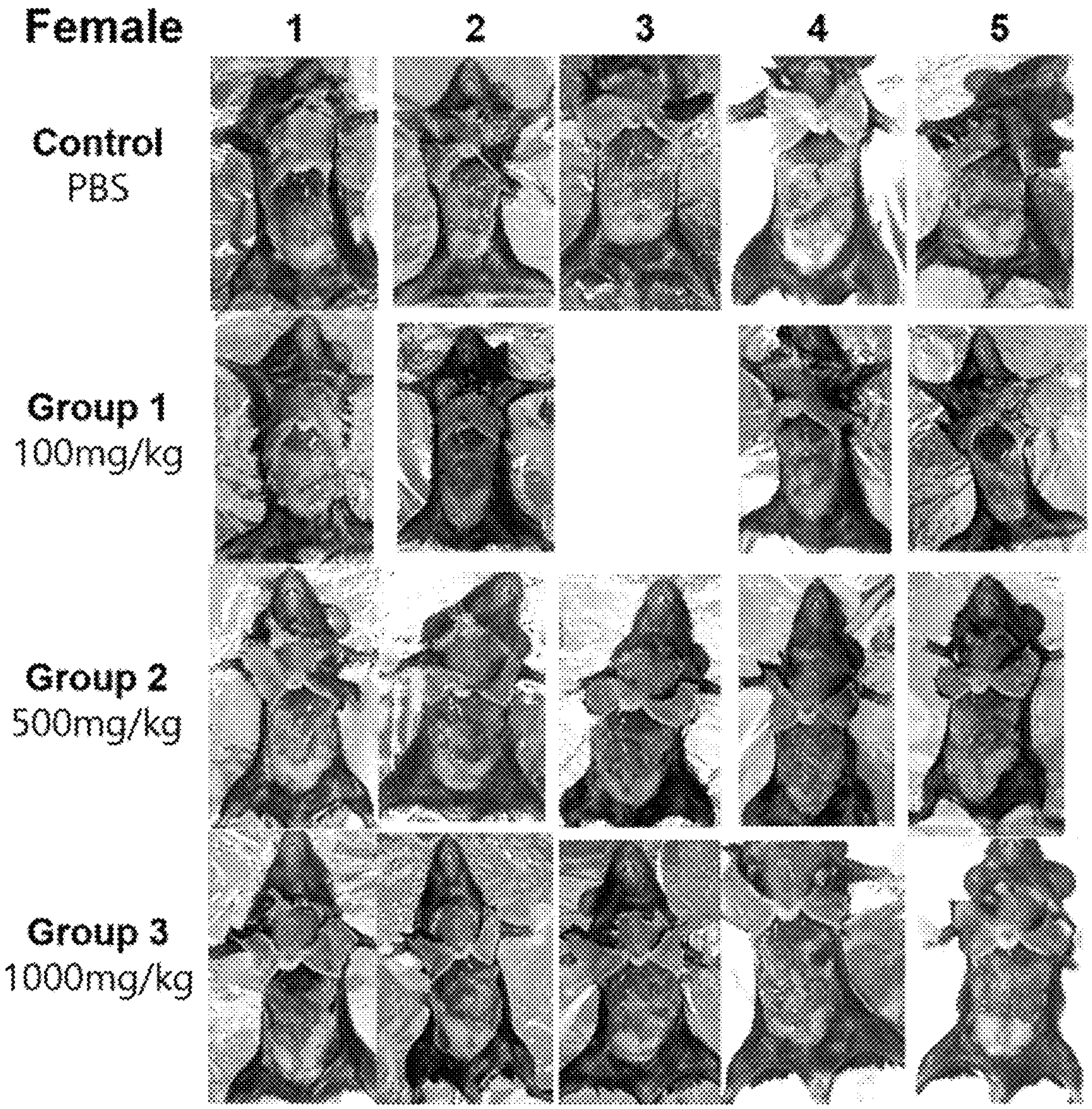

[Fig. 28A]
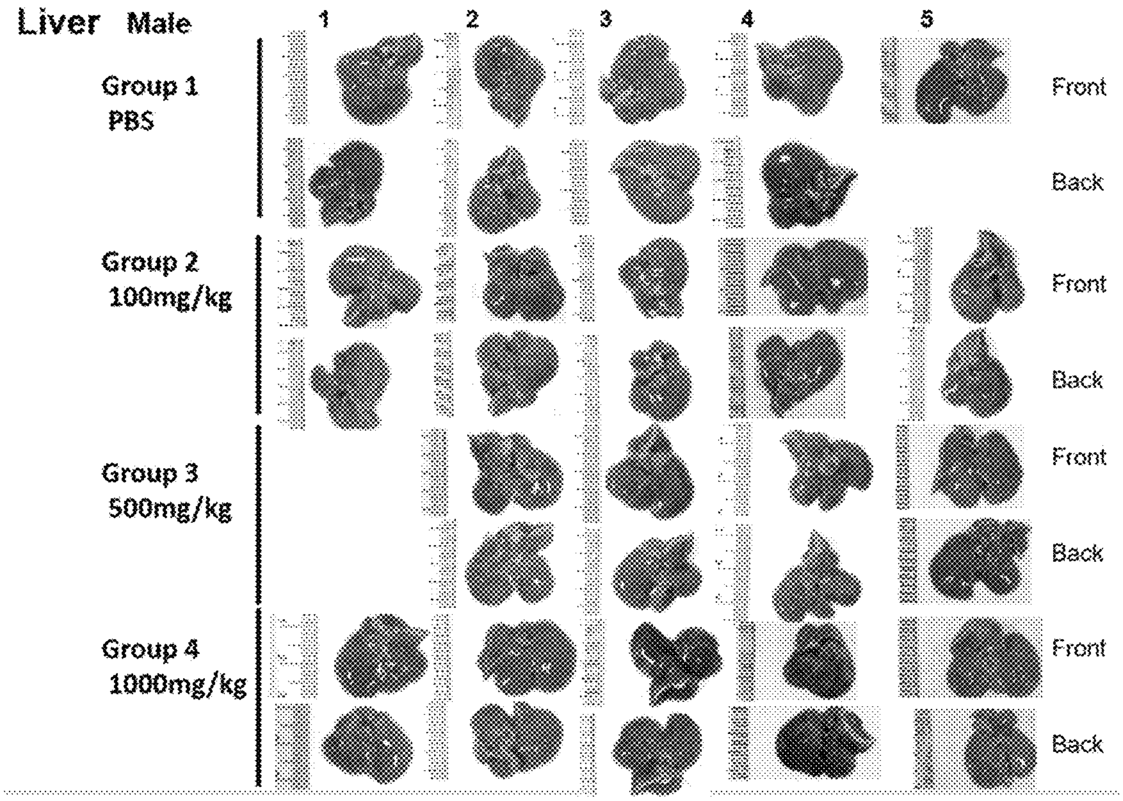

[Fig. 28B]
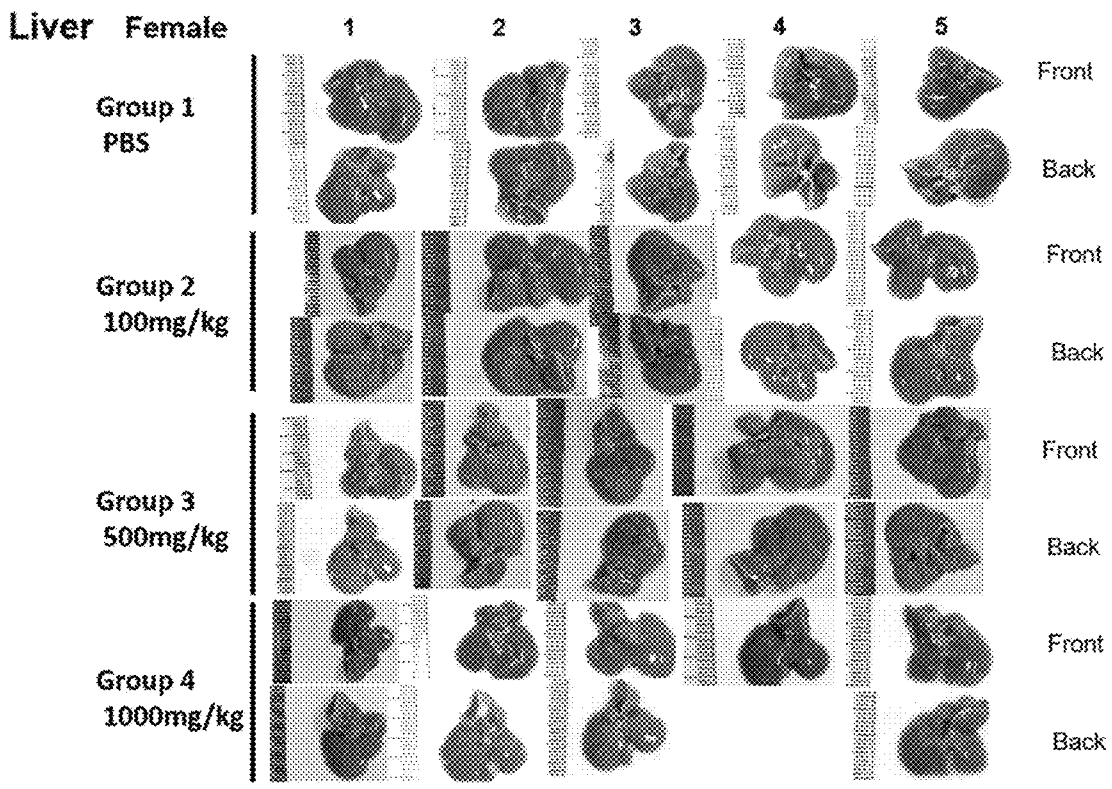

[Fig. 29A]
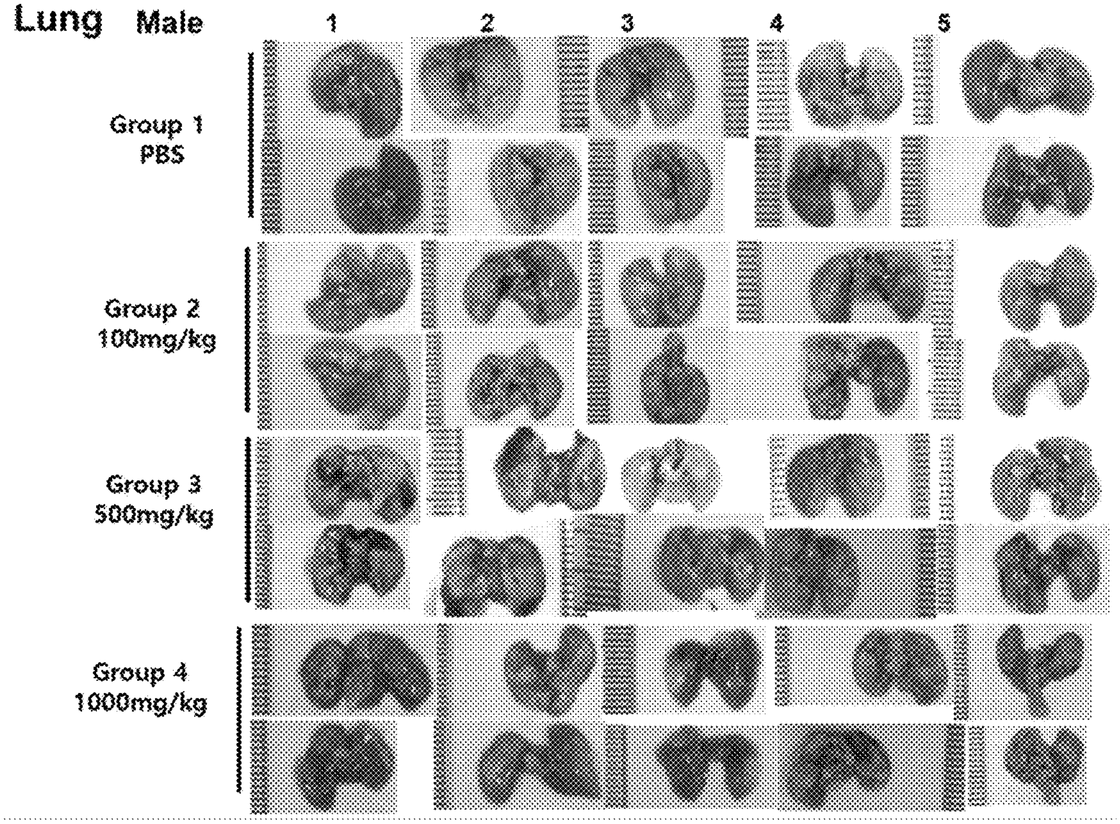

[Fig. 29B]
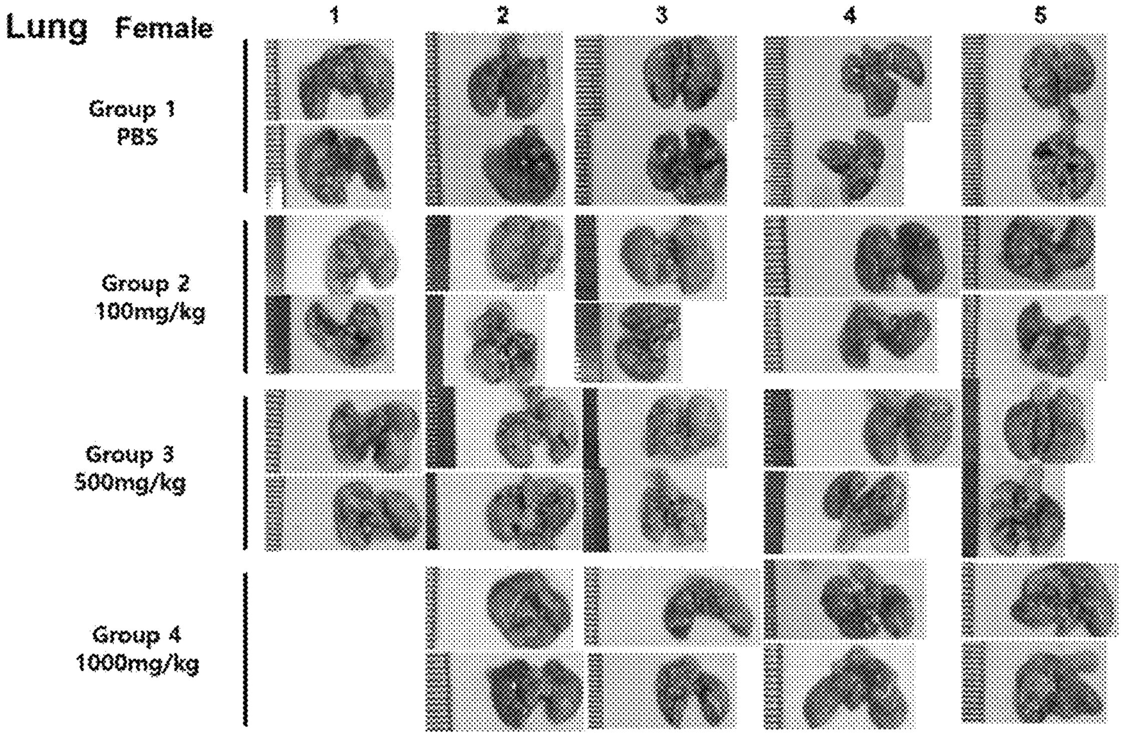
[Fig. 30]
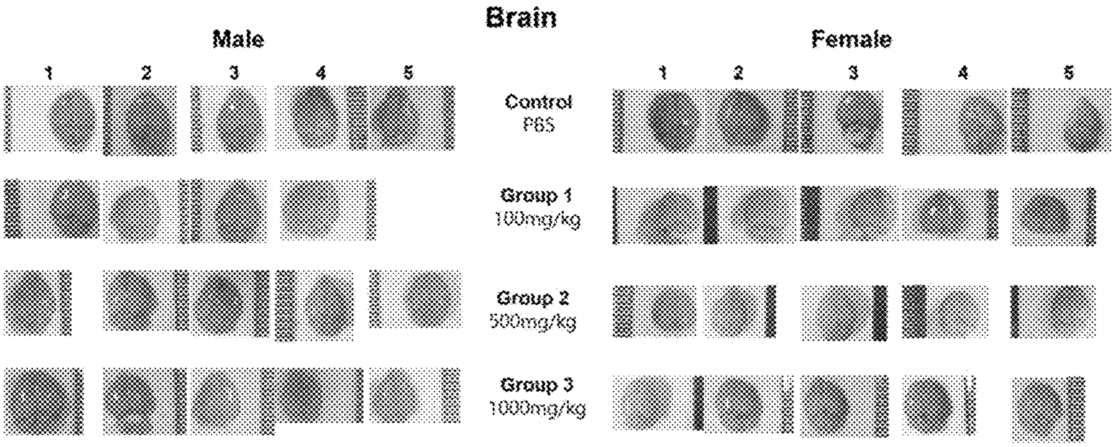

[Fig. 31]
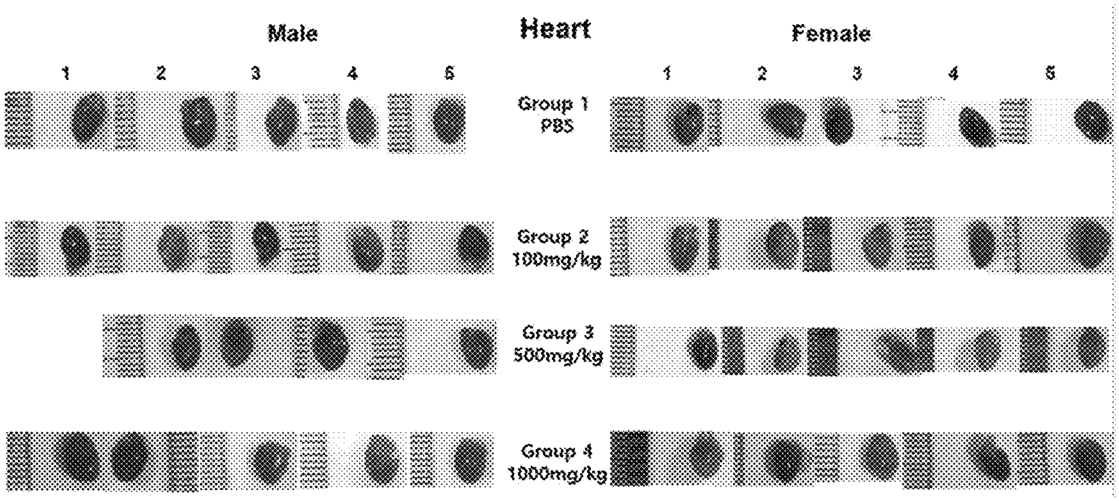
[Fig. 32]
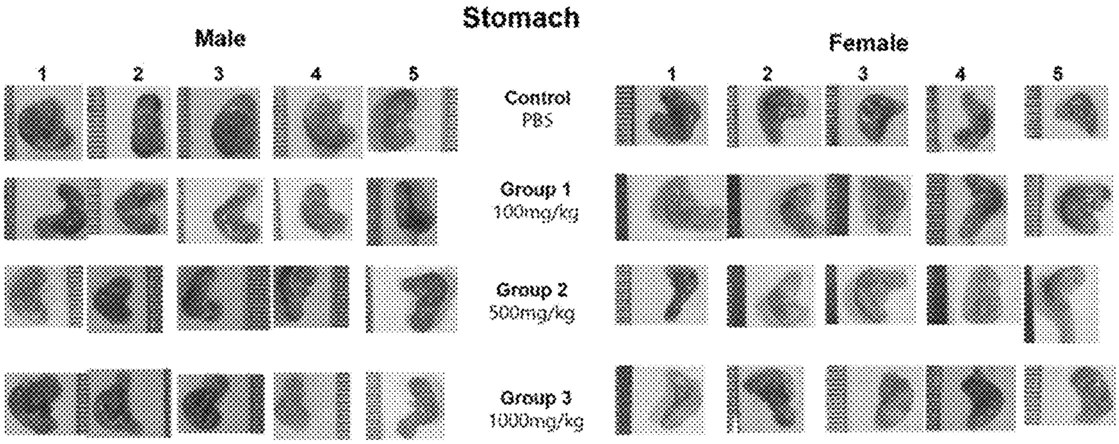

[Fig. 33]
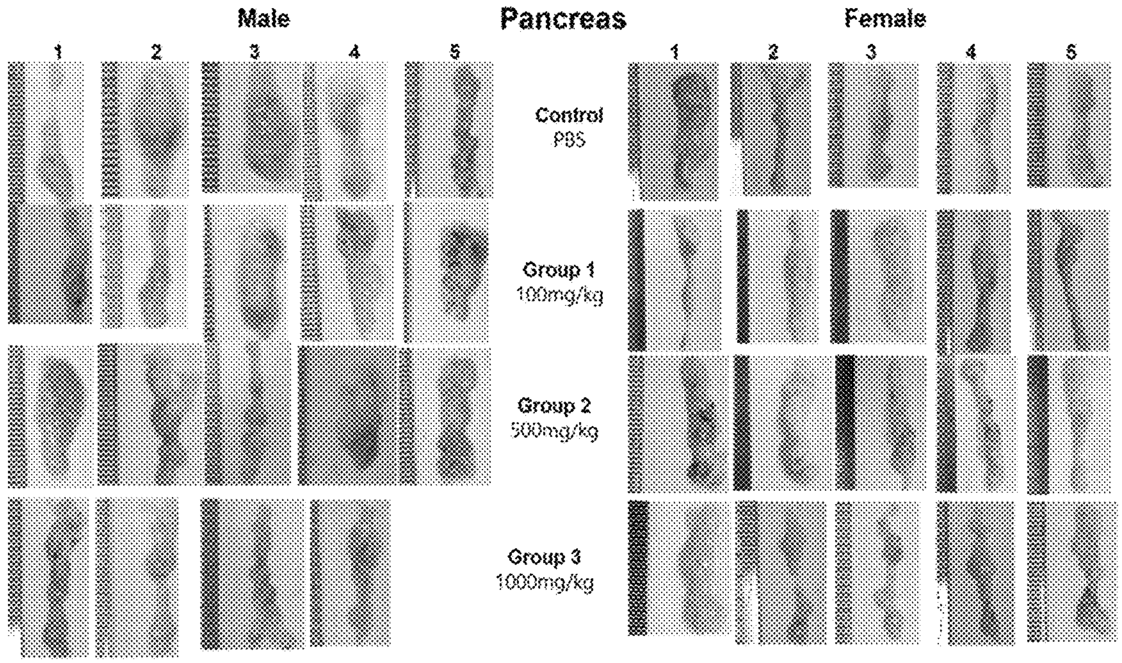
[Fig. 34]
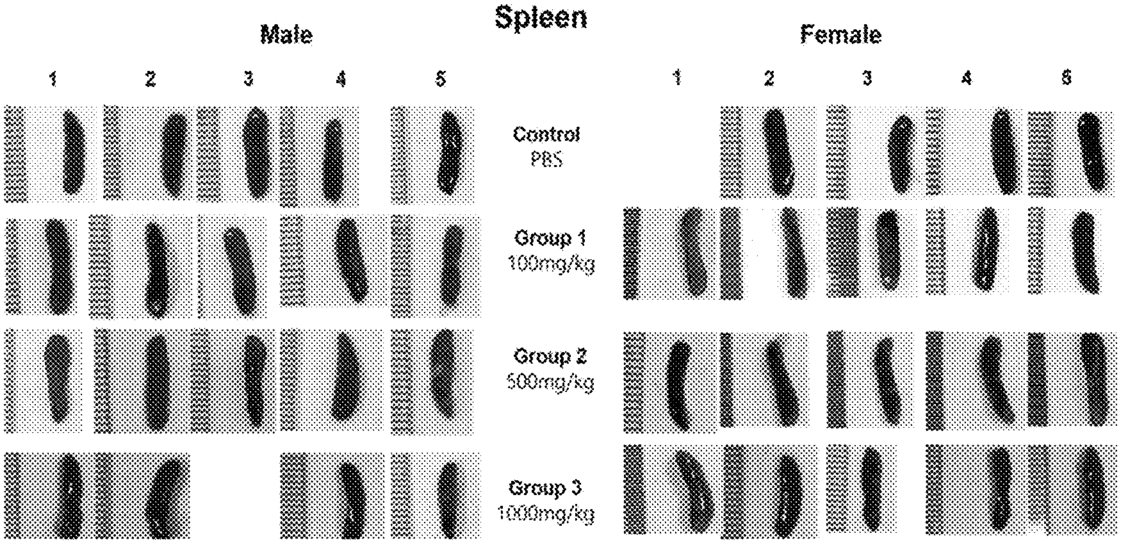

[Fig. 35A]
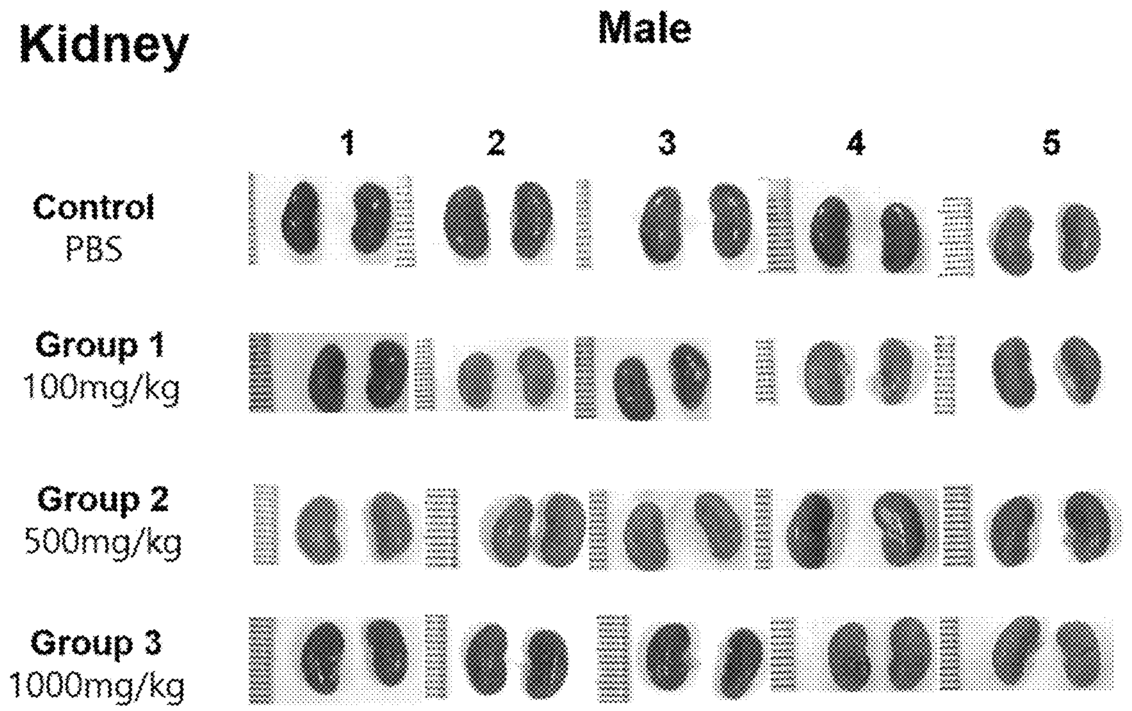
[Fig. 35B]
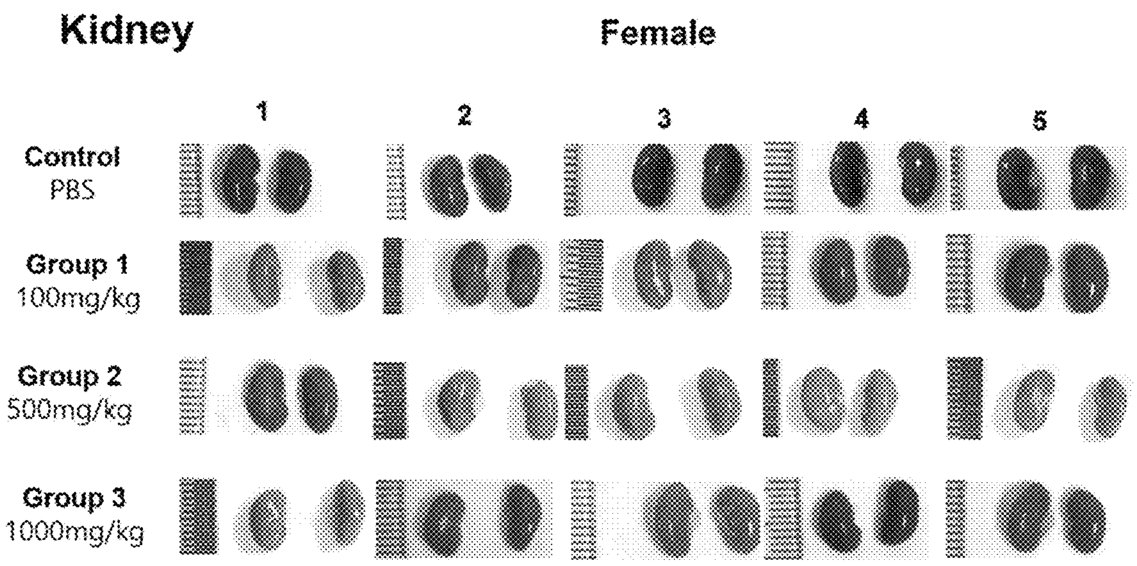

[Fig. 36a]
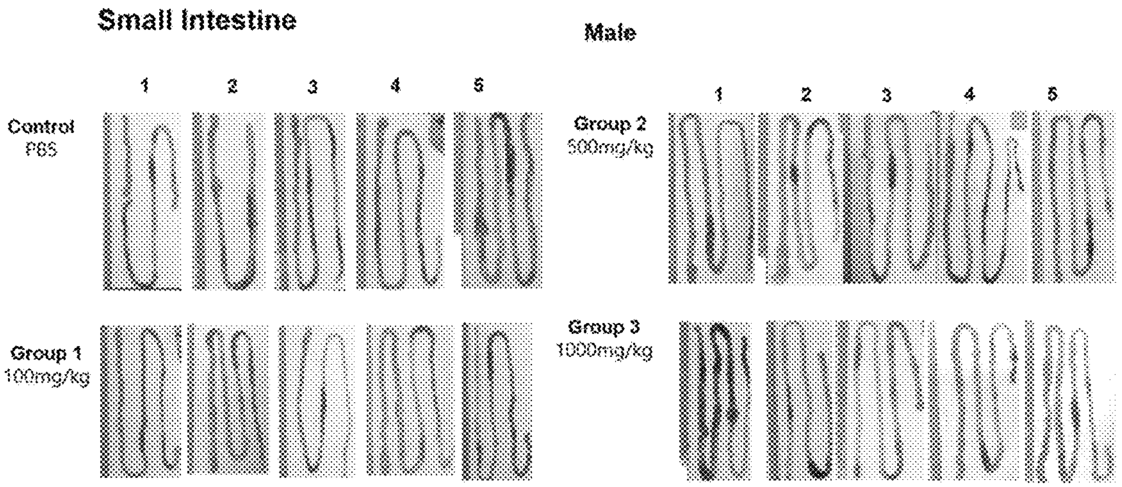
[Fig. 36B]
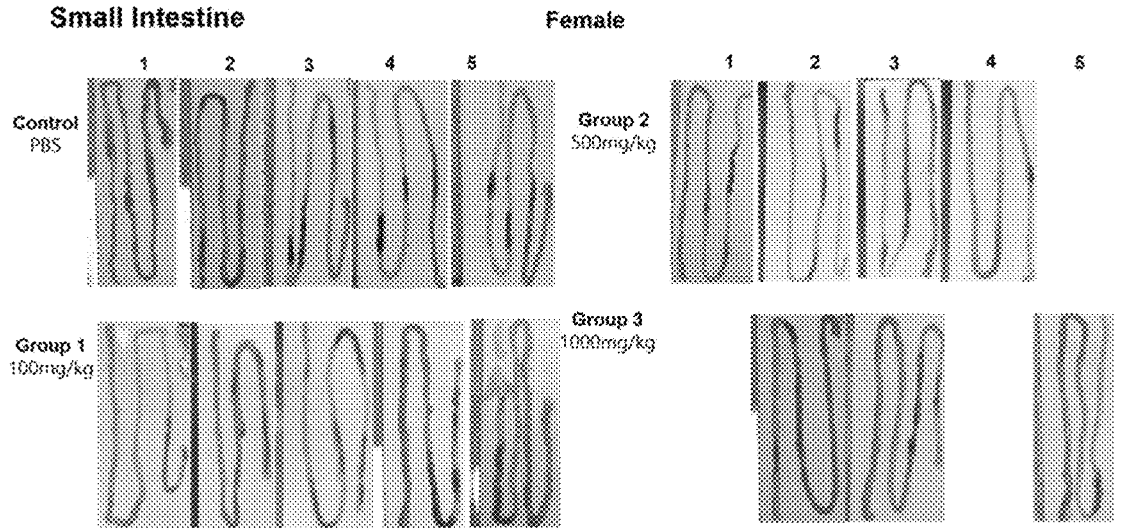

[Fig. 37A]
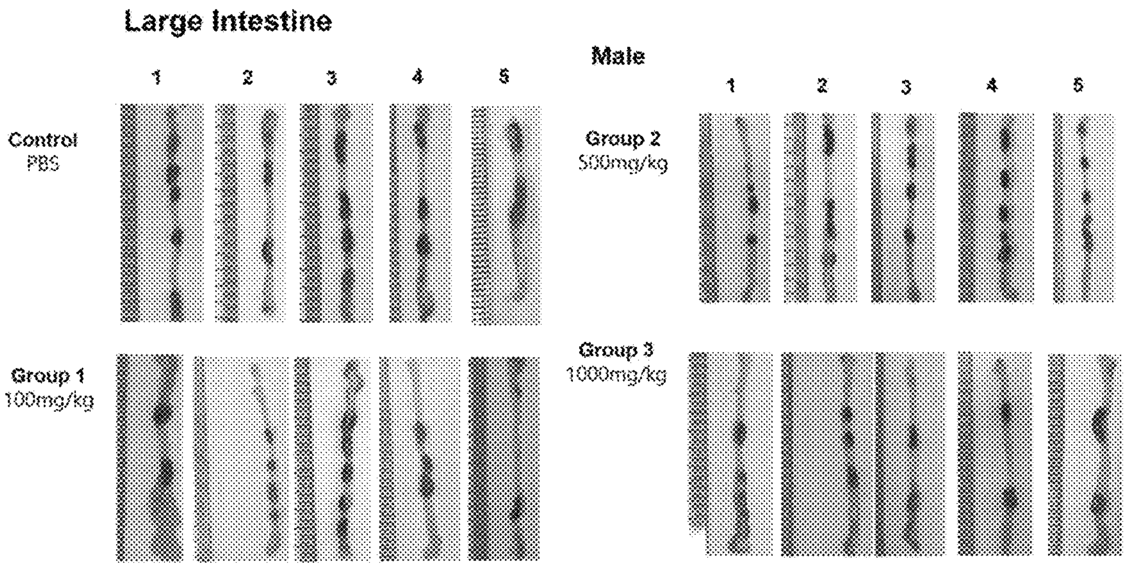
[Fig. 37B]
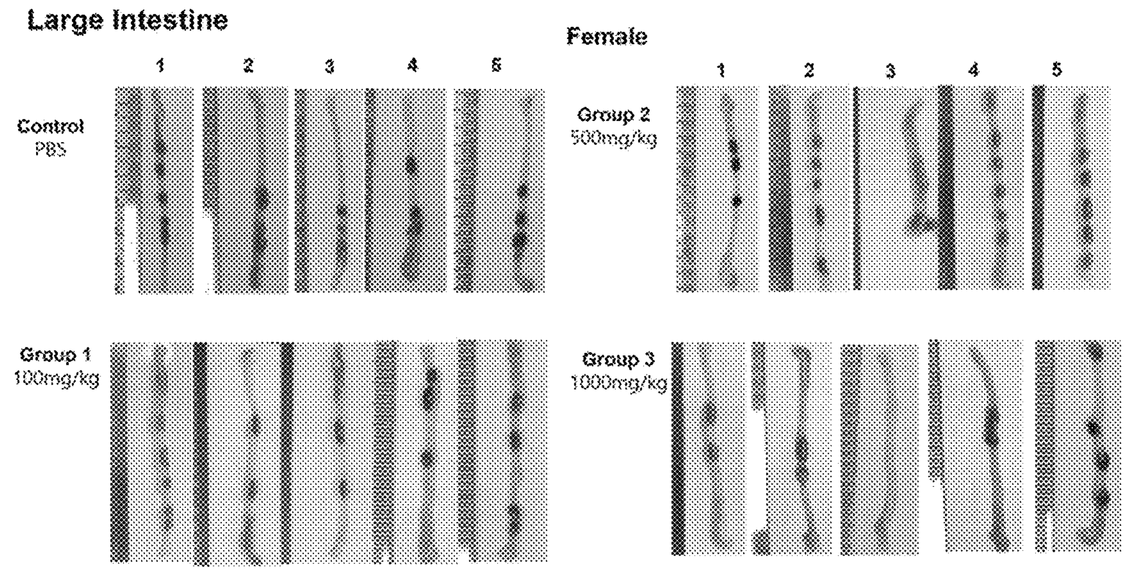

[Fig. 38]
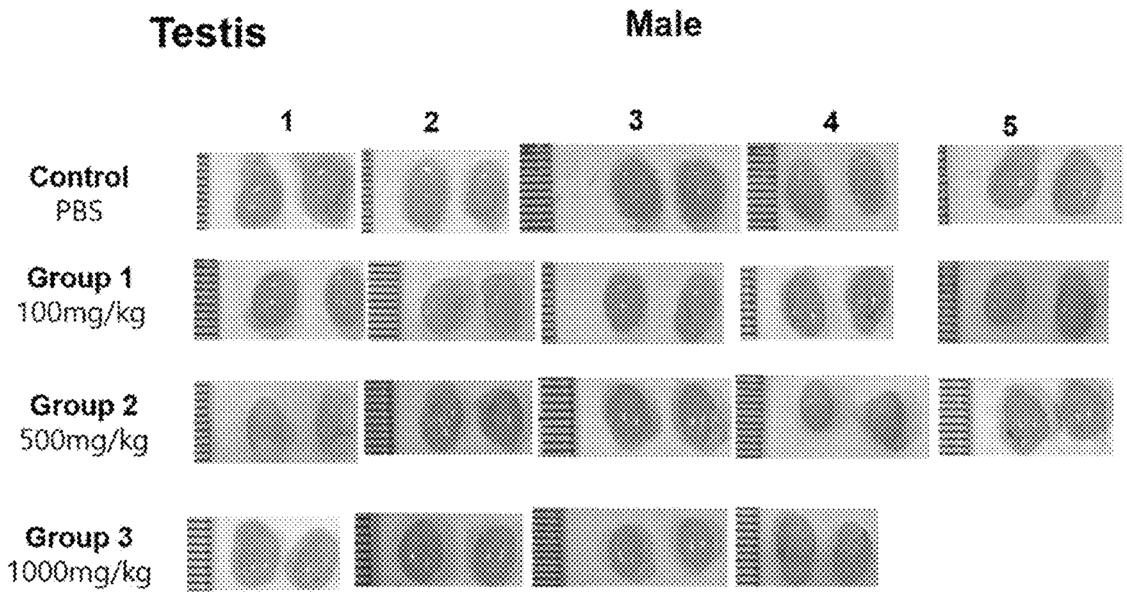
[Fig. 39]
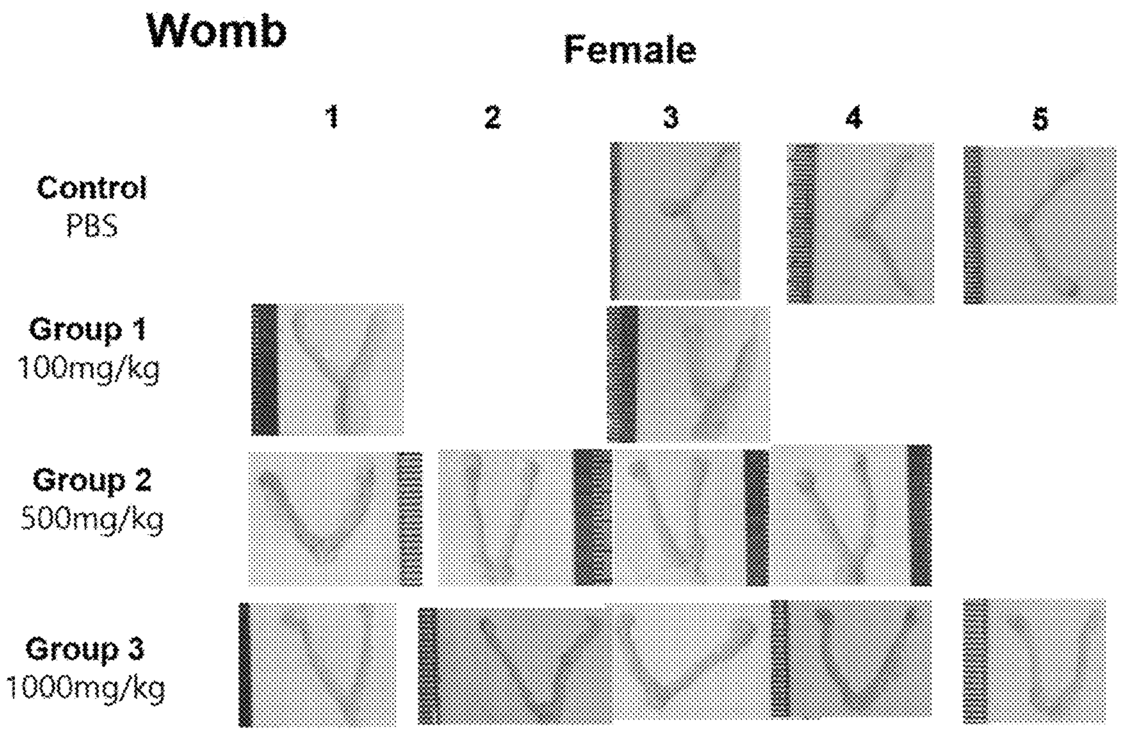

[Fig. 40]
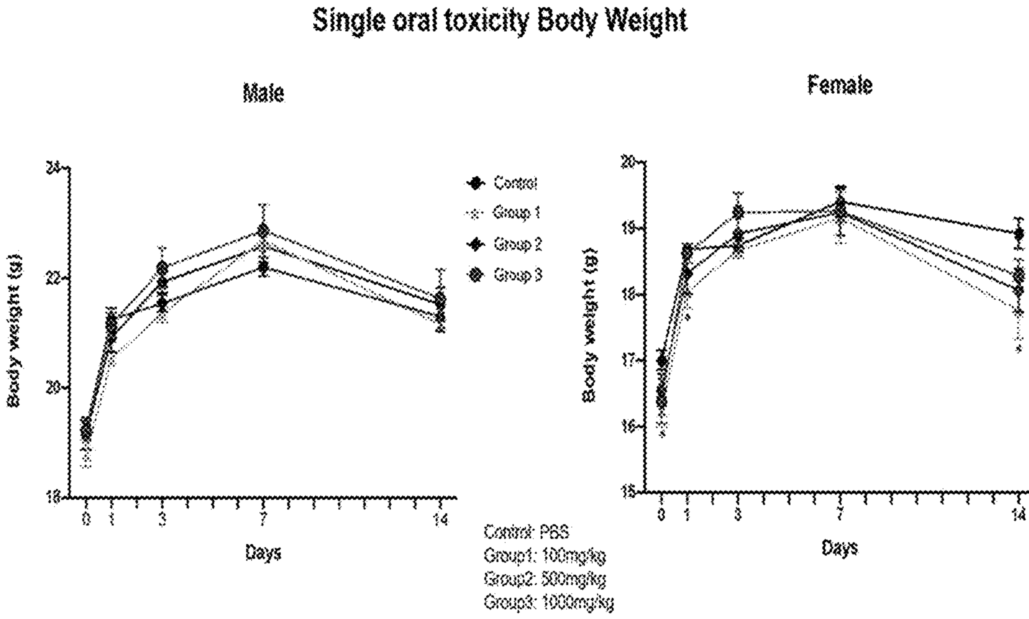
[Fig. 41A]
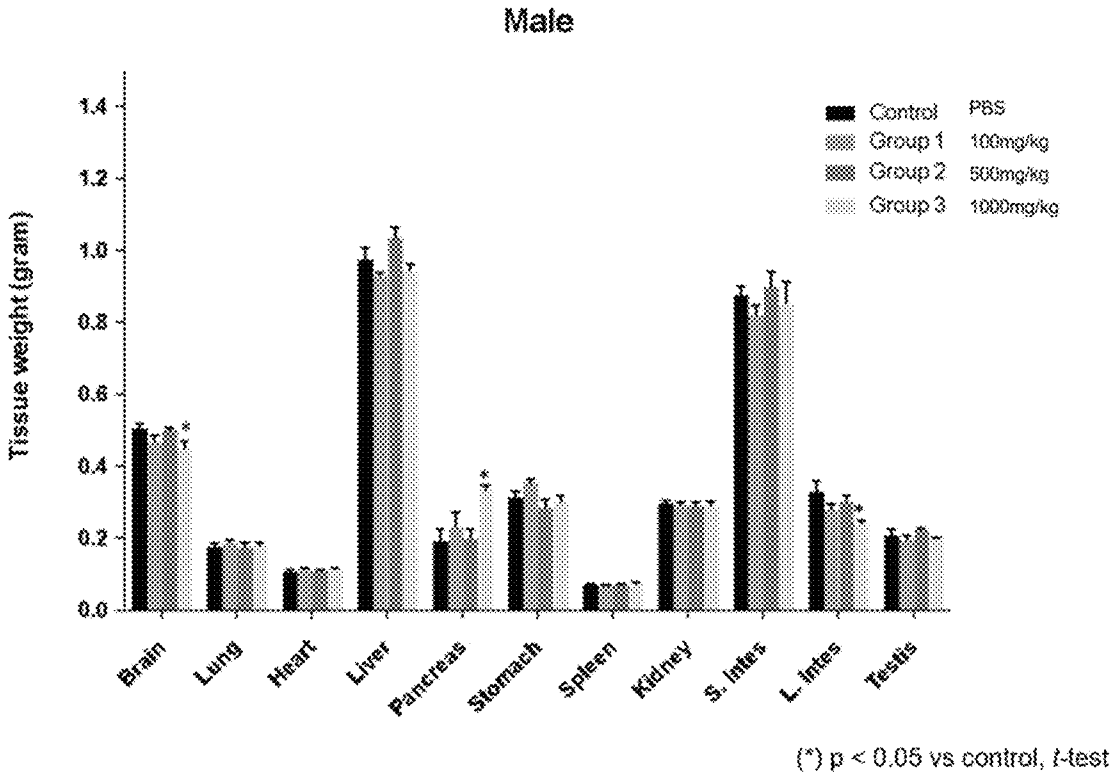

[Fig. 41B]
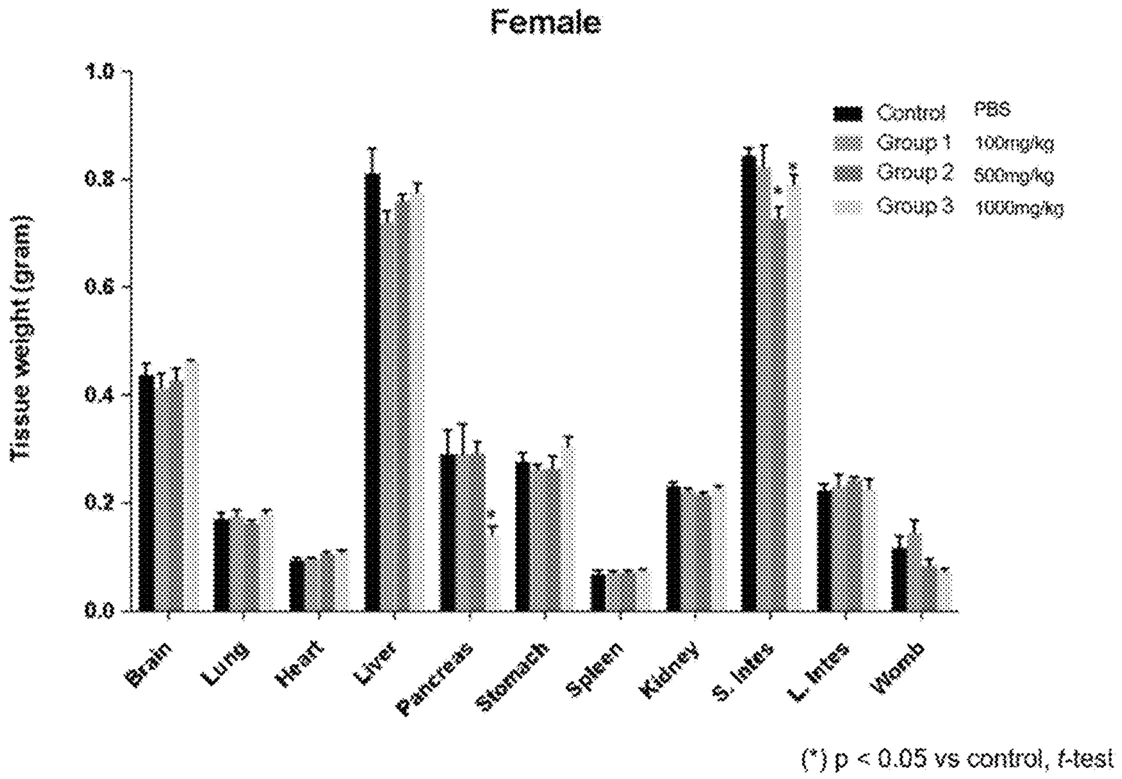
[Fig. 42A]
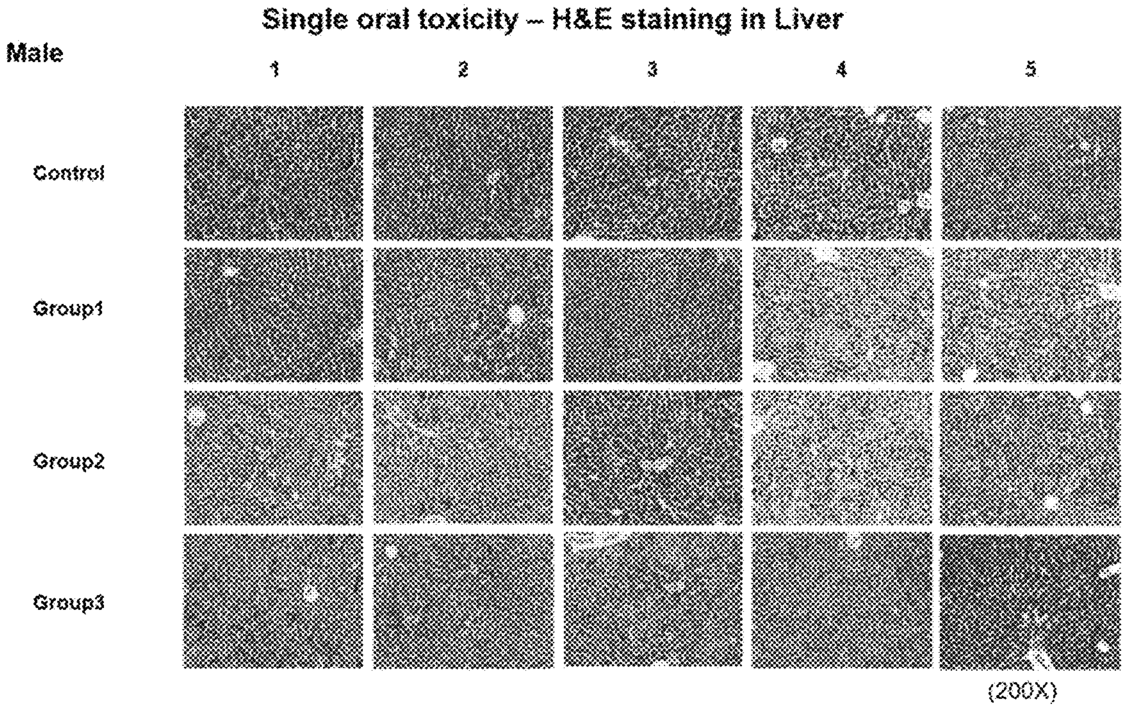

[Fig. 42B]
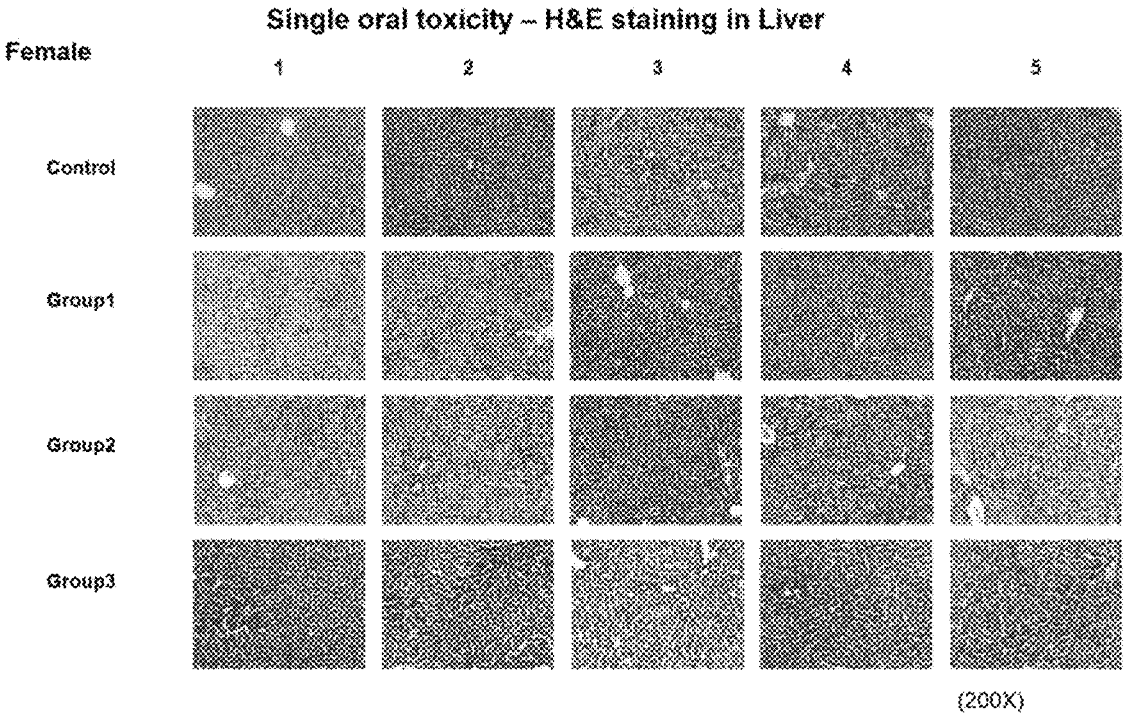

[Fig. 43A]
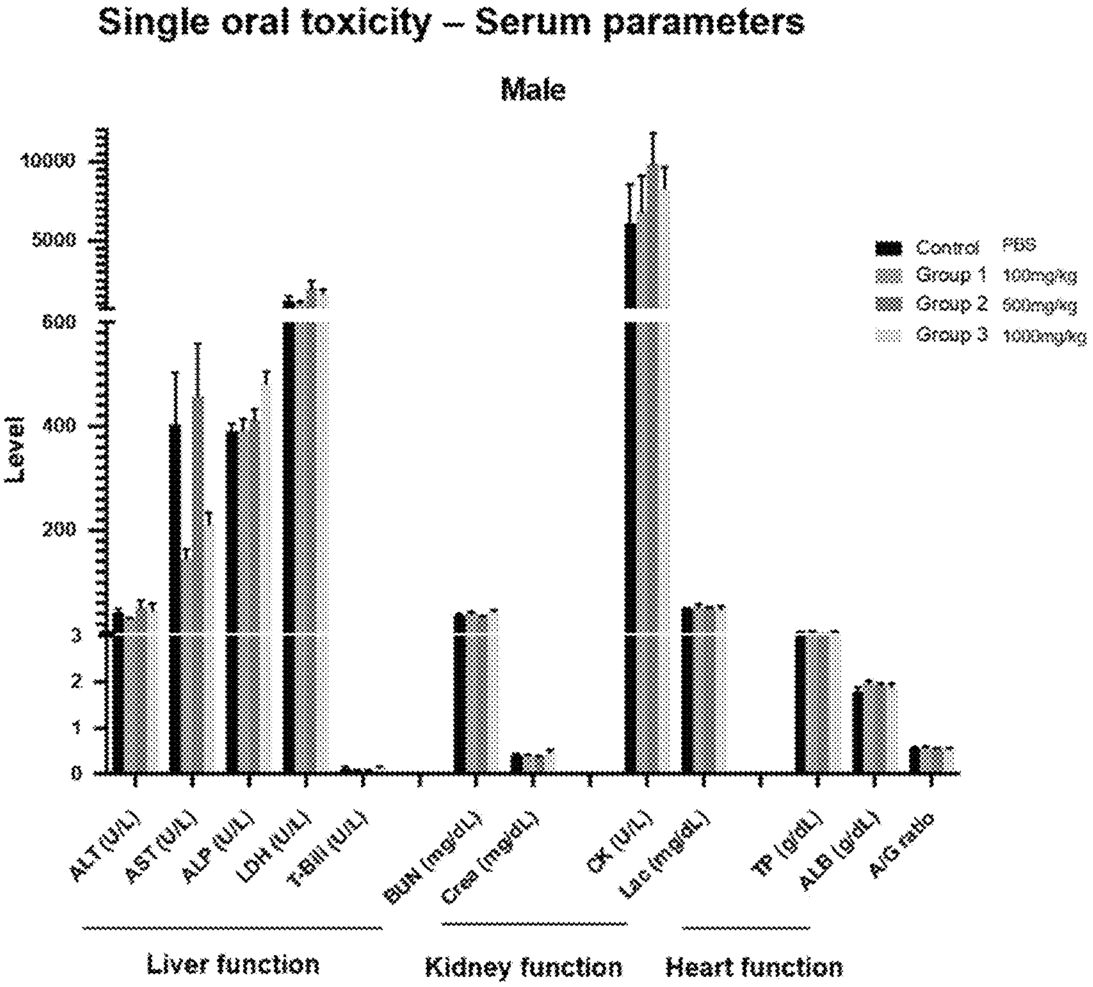

[Fig. 43B]
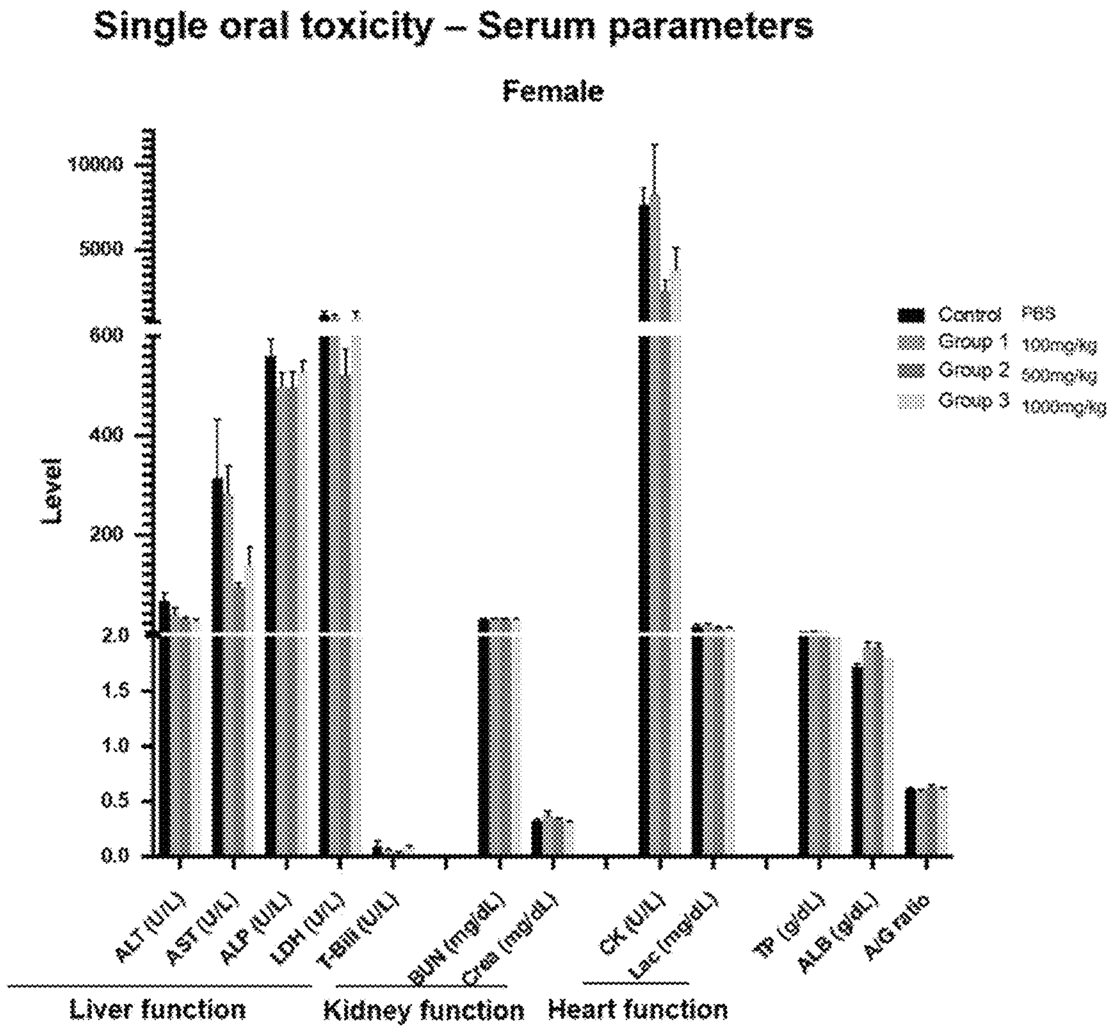

COMPOSITION FOR IMPROVING, PREVENTING OR TREATING MUSCULAR DISORDERS INCLUDING SULFONAMIDE-BASED COMPOUNDS

CROSS-REFERENCE TO RELATED APPLICATIONS

This application is based on and claims priority from Korean Patent Application No. 10-2022-0043350, filed on Apr. 7, 2022, and Korean Patent Application No. 10-2022-0058865, filed on May 13, 2022, and Korean Patent Application No. 10-2022-0186355, filed on Dec. 27, 2022, with the Korean Intellectual Property Office, the disclosure of which is incorporated herein in its entirety by reference.

TECHNICAL FIELD

The present disclosure relates to a composition for improving, treating or preventing muscular disorders including sulfonamide-based compounds.

BACKGROUND

Sarcopenia is a disease in which the muscle mass is reduced or the muscle strength decreases due to diseases, aging, and the like. The muscle mass gradually decreases after the age of 40's, and it is estimated that a decrease of 8% in the muscle mass occurs every 10 years until the age of 70's, and thereafter, a more rapid decrease in the muscle mass occurs, and it is known that the decrease in the muscle mass may occur up to 15% every 10 years.

Through many follow-up studies, it has been found that the physiological changes that occur in the elderly are diverse, and in general, the muscle mass and the bone density decrease simultaneously with increasing age. Senile sarcopenia causes not only direct muscle strength reduction to increase the risk of death due to reduction and disability of various body functions, but also a decrease in metabolism and a decrease in immunity to increase the prevalence of metabolic diseases such as hypertension, diabetes, arthritis, obesity, and cancer. In particular, the senile sarcopenia is a disease that occurs in 40% of the elderly over 80 years of age and is expected to increase social and economic burdens in the aging era.

PHD finger protein 20 (PHF 20) is a protein also known as glioma-expressed antigen 2 (GLEA2). Recently, it has been found that PHF 20, as a transcription factor, acts on muscle damage and sarcopenia by regulating a sub-target protein YY1. It has been reported that the expression of PHF20 increases and then decreases during muscle cell differentiation using myoblasts (C2C12), and this phenomenon is regulated together with the expression of a muscle differentiation inhibitory protein YY1.

Meanwhile, there are three major treatment methods for sarcopenia. The first is exercise. It has been reported that the exercise increases the protein synthesis ability of skeletal muscle in the short term, and increases muscle strength or mobility in the elderly. However, the exercise is not suitable for long-term treatment. Second, testosterone or anabolic steroids can be used as drug treatment, but induces masculinization in women and causes side effects such as prostate symptoms in men. Other approved prescriptions include dehydroepiandrosterone (DHEA) and growth hormone, which have been reported in studies that can be used as treatment methods at sites containing selective androgen receptor modulators (SARMs). In addition, although diet therapy is known as a treatment method, according to nutritional assessments, malnutrition, and modern eating habits are inadequate to maintain adequate total body mass. However, the reality is that there is no fundamental therapeutic agent or enhancer for sarcopenia.

SUMMARY

In order to solve the problems, the present inventors of the present disclosure have screen materials that may restore or alleviate the inhibition of muscle differentiation under conditions that muscle differentiation in myoblasts is inhibited by PHF20 overexpression, by using a screening system constructed using PHF20/YY1. Accordingly, the present inventors confirmed that the selected compounds could be used to inhibit muscle reduction and promote muscle differentiation, and completed the present disclosure.

According to an aspect of the present disclosure, there is provided a pharmaceutical composition for prevention or treatment that may help treat, relieve, alleviate or prevent diseases, including a sulfonamide-based compound represented by Chemical Formula 1 below or a salt thereof; or a food composition; a quasi-drug composition; a feed composition; or a composition for feed additives capable of preventing, improving, relieving or alleviating desired symptoms or assisting in the desired symptoms.

In one embodiment, an objective of the present disclosure is to provide a pharmaceutical composition for preventing or treating muscular disorders including a sulfonamide-based compound represented by Chemical Formula 1 below or a pharmaceutically acceptable salt thereof.

In one embodiment, another objective of the present disclosure is to provide a food composition for preventing or improving muscular disorders including a sulfonamide-based compound represented by Chemical Formula 1 below or a food acceptable salt thereof.

In one embodiment, yet another objective of the present disclosure is to provide a feed composition for preventing or improving muscular disorders including a sulfonamide-based compound represented by Chemical Formula 1 below or a salt thereof.

[Chemical Formula 1]

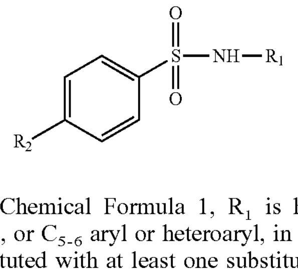

In Chemical Formula 1, $R_1$ is hydrogen, cyamamide, acetyl, or $C_{5-6}$ aryl or heteroaryl, in which $R_1$ is optionally substituted with at least one substituent selected from $C_{1-3}$ alkyl, $C_{1-3}$ alkoxy, and phenyl, and $R_2$ is —$NH_2$ or a compound represented by Chemical Formula 1-1 below.

[Chemical Formula 1-1]

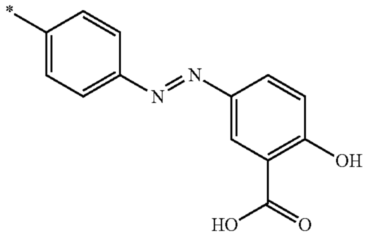

In the present disclosure, the term “prevention” refers to all actions that inhibit the development of muscular disorders by administering the composition, or inhibit or delay the severity of muscular disorders.

In the present disclosure, the term “treatment”, “improvement”, “relief”, or “alleviation” refers to all actions that improve or beneficially change the symptoms of muscular disorders by administration of the composition.

In the present disclosure, “capable of assisting” means to inhibit or delay symptoms of muscular disorders by administering the composition of the present disclosure, or to help or be able to help in improving the symptoms caused by muscular disorders. It may be used as an adjuvant to enhance an effect of medicines for treatment, and has meaning as an adjuvant as a health functional food or functional food.

In the present disclosure

“ 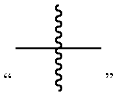 ”

and ——* means a position to be linked.

The terms used in the exemplary embodiments are used for the purpose of description only, and should not be construed to be limited. The singular expression includes the plural expression unless the context clearly dictates otherwise. In the present application, it should be understood that term “comprising” or “having” indicates that a feature, a number, a step, an operation, a component, a part or the combination thereof described in the specification is present, but does not exclude a possibility of presence or addition of one or more other features, numbers, steps, operations, components, parts or combinations thereof, in advance.

Unless otherwise contrarily defined, all terms used herein including technological or scientific terms have the same meanings as those generally understood by a person with ordinary skill in the art to which exemplary embodiments pertain. Terms which are defined in a generally used dictionary should be interpreted to have the same meaning as the meaning in the context of the related art, and are not interpreted as ideal or excessively formal meanings unless otherwise defined in the present application.

In addition, in the description with reference to the accompanying drawings, like components designate like reference numerals regardless of reference numerals and a duplicated description thereof will be omitted. In describing the example exemplary embodiments, a detailed description of related known technologies will be omitted if it is determined that they unnecessarily make the gist of the example exemplary embodiments unclear.

According to the present disclosure, the composition for preventing, improving or treating muscular disorders including the sulfonamide-based compounds or salts thereof can prevent inhibition of differentiation of myoblasts by regulating the expression of PHF20 and YY1. Accordingly, since the composition may prevent or alleviate muscle loss, or promote muscle regeneration to improve muscle functions and muscle mass, the composition can be effectively used for therapeutic agents, foods, or feeds for prevention, improvement or treatment of muscle disorders, and improving muscle functions or muscle mass.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1 is a diagram showing a process of constructing a high throughput screening (HTS) system in a cell line that may easily monitor the differentiation pattern of muscle cells according to an exemplary embodiment of the present disclosure.

FIGS. 2A and 2B are diagrams illustrating results of confirming PHF20 expression (FIG. 2A) and GFP expression (FIG. 2B) according to a concentration of a selection marker in order to prepare a stable cell line for constructing a high throughput screening (HTS) system according to an exemplary embodiment of the present disclosure.

FIG. 3 is a fluorescent picture and a graph showing a result of GFP expression according to a marker concentration and time in order to prepare a stable cell line for constructing a high throughput screening (HTS) system according to an exemplary embodiment of the present disclosure.

FIG. 4 is a diagram illustrating a result of screening candidate substances using the HTS system constructed according to an exemplary embodiment of the present disclosure.

FIG. 5 is a graph showing an effect of suppressing an action of inhibiting the formation of myoblasts upon treatment with sulfamethazine according to an exemplary embodiment of the present disclosure.

FIG. 6 is a graph showing $IC_{50}$ values based on the results of suppressing the inhibition of the formation of myoblasts by concentration of sulfamethazine according to an exemplary embodiment of the present disclosure.

FIG. 7 is a diagram illustrating a Western blot analysis result for each compound in a C2C12 muscle cell line, according to an exemplary embodiment of the present disclosure.

FIGS. 8A to 8C are cellular immunofluorescence staining images for confirming the differentiation ability of muscle cells after differentiation into myotubes from a group of treating a C2C12-PHF20 inducible cell line with doxycyclin to overexpress PHF20 and a control group treated with no doxycyclin, treating a drug (sulfonamide-based compound) on day 4 of differentiation, and then staining with heavy chain of myosin II (MF20) involved in muscle function and development on day 5 of differentiation, according to an exemplary embodiment of the present disclosure.

FIG. 9 is a graph of confirming a change in body weight of mice for each administration group in order to confirm a treadmill exercise capacity recovery effect depending on a dose of sulfasalazine in an aging mouse model according to an exemplary embodiment of the present disclosure (a horizontal axis of the graph means a day of administration, and a vertical axis means a weight of the mouse).

FIG. 10 is a graph showing changes in treadmill exercise capacity recovery effect depending on a dose of sulfasalazine in an aging mouse model according to an exemplary embodiment of the present disclosure (a horizontal axis of the graph means a day of administration, and a vertical axis means a latency to fall).

FIG. 11 is a graph showing changes in balance ability recovery effect of a Rota Rod depending on a dose of sulfasalazine in an aging mouse model according to an exemplary embodiment of the present disclosure.

FIGS. 12A and 12B are diagrams illustrating confirming a grip strength recovery effect depending on a dose of sulfasalazine in an aging mouse model according to an exemplary embodiment of the present disclosure, and show changes in grip strength recovery (12A) of hind legs (2 paws) and changes in grip strength recovery (12B) of all legs (4 paws) depending on a dose.

FIG. 13 is a graph of confirming changes in body weight of mice for each administration group in order to confirm a treadmill exercise capacity recovery effect depending on a dose of sulfasalazine in a high-fat diet CTX sarcopenia mouse model according to an exemplary embodiment of the present disclosure.

FIG. 14 is a graph showing changes in balance ability recovery effect of a Rota Rod depending on a dose of sulfasalazine in a high-fat diet CTX sarcopenia mouse model according to an exemplary embodiment of the present disclosure.

FIGS. 15A and 15B are diagrams illustrating confirming a grip strength recovery effect depending on a dose of sulfasalazine in a high-fat diet CTX sarcopenia mouse model according to an exemplary embodiment of the present disclosure and show changes in grip strength recovery (15A) of hind legs (2 paws) and changes in grip strength recovery (15B) of all legs (4 paws) depending on a dose.

FIG. 16 is an image of photographing a Velcro injured sarcopenia mouse model according to an exemplary embodiment of the present disclosure, in which a left image is an image taken after winding a sports tape around the ankle and calf of the mouse, and middle and right images are images taken after winding and fixing a sports tape around the entire leg from the ankle of the mouse and then winding and fixing the entire leg with Velcro.

FIG. 17 is a graph of confirming changes in body weight of mice for each administration group in order to confirm a treadmill exercise capacity recovery effect depending on a dose of sulfasalazine in a Velcro injured sarcopenia mouse model according to an exemplary embodiment of the present disclosure.

FIGS. 18A and 18B are diagrams showing a distance (FIG. 18A) and time (FIG. 18B) of running a treadmill before drug administration in order to determine whether to construct a Velcro injured sarcopenia mouse model according to an exemplary embodiment of the present disclosure (in FIG. 18A, a horizontal axis means a relative ratio (%) to a distance in a control group, and a vertical axis means a drug treatment group, and in FIG. 18B, a horizontal axis means a relative ratio (%) to time in a control group, and a vertical axis means a drug treatment group).

FIGS. 19A and 19B are graphs of confirming distance (FIG. 19A) and time (FIG. 19B) run on a treadmill for each group depending on a dose and an administration date of sulfasalazine in order to confirm treadmill exercise capacity of a Velcro injured sarcopenia mouse model according to an exemplary embodiment of the present disclosure (in FIG. 19A, a horizontal axis means an administration day, and a vertical axis means a distance, and in FIG. 19B, a horizontal axis means an administration day, and a vertical axis means time).

FIG. 20 is a photograph of muscle damage recovery observed with an optical microscope after H&E staining after oral administration of sulfamethazine for 10 days after CTX injection into the thigh of a mouse according to an exemplary embodiment of the present disclosure.

FIG. 21 is a photograph observed under a fluorescence microscope to identify a muscle recovery effect for each muscle type (myosin type I, myosin type IIa, and myosin type IIb) according to oral administration of sulfamethazine for 10 days in a CTX-induced sarcopenia mouse model according to an exemplary embodiment of the present disclosure.

FIG. 22 is a graph of confirming changes in body weight of mice for each administration group in order to confirm a balance ability recovery effect of Rota Rod according to a dose of sulfamethazine according to an exemplary embodiment of the present disclosure.

FIG. 23 is a diagram illustrating a method and conditions for confirming Rota Rod balance ability according to an exemplary embodiment of the present disclosure.

FIG. 24 is a graph showing changes in balance ability recovery effect of a Rota Rod depending on a dose of sulfamethazine according to an exemplary embodiment of the present disclosure.

FIG. 25 is a graph of confirming changes in body weight of mice for each administration group in order to confirm a grip strength recovery effect according to a dose of sulfamethazine according to an exemplary embodiment of the present disclosure.

FIGS. 26A and 26B are diagrams illustrating confirming a grip strength recovery effect depending on a dose of sulfamethazine according to an exemplary embodiment of the present disclosure, and show changes in grip strength recovery (26A) of hind legs (2 paws) and changes in grip strength recovery (26B) of all legs (4 paws) depending on a dose.

FIGS. 27A to 27C are diagrams illustrating results of confirming toxicity according to a single oral administration of sulfamethazine according to an exemplary embodiment of the present disclosure:

Control—PBS administration;
Group 1—Sulfamethazine 100 mg/kg;
Group 2—Sulfamethazine 500 mg/kg;
Group 3—Sulfamethazine 1000 mg/kg)

FIGS. 28A and 28B are photographs of confirming toxicity to the liver in mice orally administered with sulfamethazine according to an exemplary embodiment of the present disclosure.

FIGS. 29A and 29B are photographs of confirming toxicity to the lung in mice orally administered with sulfamethazine according to an exemplary embodiment of the present disclosure.

FIG. 30 is a photograph of confirming toxicity to the brain in mice orally administered with sulfamethazine according to an exemplary embodiment of the present disclosure.

FIG. 31 is a photograph of confirming toxicity to the heart in mice orally administered with sulfamethazine according to an exemplary embodiment of the present disclosure.

FIG. 32 is a photograph of confirming toxicity to the stomach in mice orally administered with sulfamethazine according to an exemplary embodiment of the present disclosure.

FIG. 33 is a photograph of confirming toxicity to the pancreas in mice orally administered with sulfamethazine according to an exemplary embodiment of the present disclosure.

FIG. 34 is a photograph of confirming toxicity to the spleen in mice orally administered with sulfamethazine according to an exemplary embodiment of the present disclosure.

FIGS. 35A and 35B are photographs of confirming toxicity to the kidney in mice orally administered with sulfamethazine according to an exemplary embodiment of the present disclosure.

FIGS. 36A and 36B are photographs of confirming toxicity to the small intestine in mice orally administered with sulfamethazine according to an exemplary embodiment of the present disclosure.

FIGS. 37A and 37B are photographs of confirming toxicity to the large intestine in mice orally administered with sulfamethazine according to an exemplary embodiment of the present disclosure.

FIG. 38 is a photograph of confirming toxicity to the testis in mice orally administered with sulfamethazine according to an exemplary embodiment of the present disclosure.

FIG. 39 is a photograph of confirming toxicity to the womb in mice orally administered with sulfamethazine according to an exemplary embodiment of the present disclosure.

FIG. 40 is a graph showing changes in body weight for each administration group in mice orally administered with sulfamethazine according to an exemplary embodiment of the present disclosure.

FIGS. 41A and 41B are graphs of confirming a weight of each of the brain, lung, heart, liver, pancreas, stomach, spleen, kidney, small intestine, large intestine, testis and womb of each administration group in mice on day 14 after orally administering sulfamethazine according to an exemplary embodiment of the present disclosure.

FIGS. 42A and 42B are photographs showing H&E staining to confirm toxicity in the liver of mice on day 14 after orally single-administering sulfamethazine according to an exemplary embodiment of the present disclosure.

FIGS. 43A and 43B are graphs showing confirming the expression of blood liver toxicity, heart toxicity, and kidney toxicity markers in mice orally single-administered with sulfamethazine according to an exemplary embodiment of the present disclosure.

DETAILED DESCRIPTION

Hereinafter, the present disclosure will be described in more detail.

The present disclosure provides a use for preventing, improving or treating muscular disorders including a sulfonamide-based compound represented by Chemical Formula 1 or a salt thereof; and a composition for preventing, improving or treating muscular disorders including a sulfonamide-based compound represented by Chemical Formula 1 or a salt thereof.

[Chemical Formula 1]

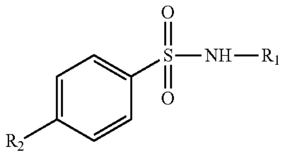

In Chemical Formula 1, $R_1$ is hydrogen, cyamamide, acetyl, or $C_{5-6}$ aryl or heteroaryl, in which $R_1$ is optionally substituted with at least one substituent selected from $C_{1-3}$ alkyl, $C_{1-3}$ alkoxy, and phenyl, and $R_2$ is —$NH_2$ or a compound represented by Chemical Formula 1-1 below.

[Chemical Formula 1-1]

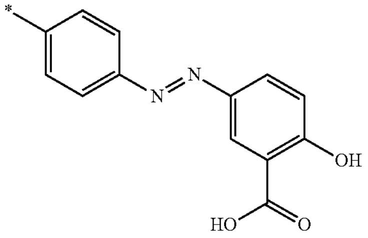

In one embodiment, the hetero element of the hetero aryl may be one or more selected from S, N, and O, one or more hetero elements may be included, and one or more hetero elements different from each other may be included.

In one embodiment, the aryl or heteroaryl may be selected from the group consisting of pyrrole, pyrazole, triazole, oxazole, furan, isoxazole, isothiazole, imidazole, diazole, thiadiazole, phenyl, pyridine, pyrimidine, triazine, oxazine, and thiazine.

In one embodiment, the aryl or heteroaryl may be thiazole, diazole, thiadiazole, phenyl, pyridine or pyrimidine.

In one embodiment, the substituent of $R_1$ may be at least one substituent selected from $C_{1-3}$ alkyl, $C_{1-3}$ alkoxy, and phenyl. In a preferred embodiment, the substituent of $R_1$ may be at least one selected from the group consisting of methyl, ethyl, methoxy, ethoxy and phenyl. One substituent of $R_1$ may be included, and one or more substituents identical to or different from each other may be included.

In one embodiment, the compound of Chemical Formula 1 may be sulfasalazine, sulfamethazine, sulfathiazole, sulfapyridine, sulfaphenazole, sulfameter, sulfamethizole, sulfaguanidine, sulfacetamide sodium, sulfadoxin, sulfadimethoxine, sulfanilamide or sulfadiazine.

In one embodiment, the salt of the compound of the present disclosure includes all kinds of salts commonly accepted in the art of the present disclosure, and may be, for example, a sodium salt.

In one embodiment, the sulfasalazine may be a compound represented by Chemical Formula 2 below.

[Chemical Formula 2]

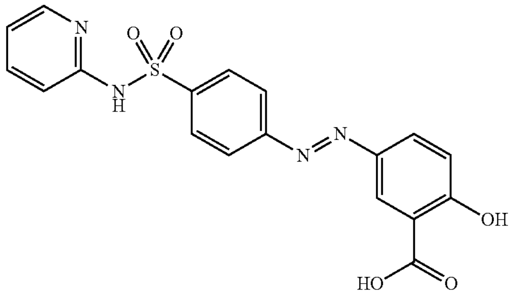

In one embodiment, the sulfamethazine may be a compound represented by Chemical Formula 3 below.

[Chemical Formula 3]

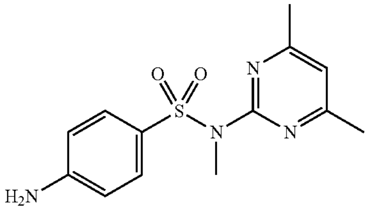

In one embodiment, the sulfathiazole may be a compound represented by Chemical Formula 4 below.

[Chemical Formula 4]

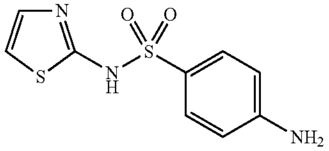

In one embodiment, the sulfapyridine may be a compound represented by Chemical Formula 5 below.

[Chemical Formula 5]

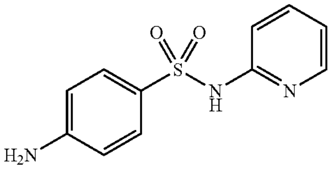

In one embodiment, the sulfaphenazole may be a compound represented by Chemical Formula 6 below.

[Chemical Formula 6]

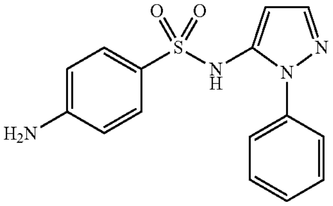

In one embodiment, the sulfameter may be a compound represented by Chemical Formula 7 below.

[Chemical Formula 7]

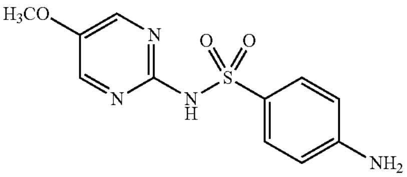

In one embodiment, the sulfamethizole may be a compound represented by Chemical Formula 8 below.

[Chemical Formula 8]

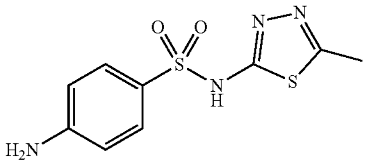

In one embodiment, the sulfaguanidine may be a compound represented by Chemical Formula 9 below.

[Chemical Formula 9]

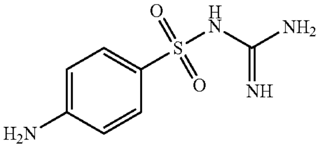

In one embodiment, the sulfacetamide may exist in the form of a sodium salt, and more specifically, may be a compound represented by Chemical Formula 10 below.

[Chemical Formula 10]

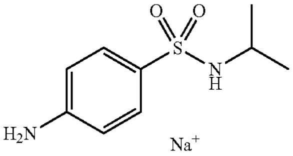

In one embodiment, the sulfadoxin may be a compound represented by Chemical Formula 11 below.

[Chemical Formula 11]

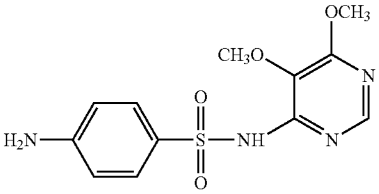

In one embodiment, the sulfadimethoxine may be a compound represented by Chemical Formula 12 below.

[Chemical Formula 12]

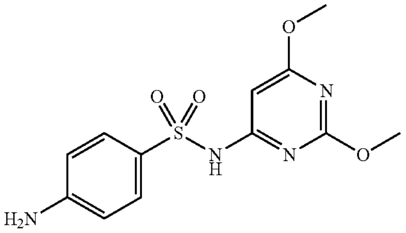

In one embodiment, the sulfanilamide may be a compound represented by

[Chemical Formula 13]

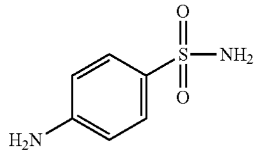

In one embodiment, the sulfadiazine may be a compound represented by Chemical Formula 14 below.

[Chemical Formula 14]

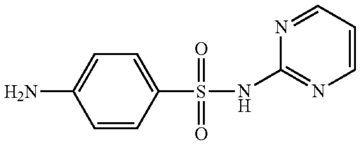

In the present disclosure, the muscular disorder means a disease or symptom that causes a reduced muscle function; a decrease in muscle mass; muscle wasting; or muscle degeneration, or worsens these symptoms.

In this specification, the term 'muscle' collectively refers to tendons and muscles. Further, the 'muscle function' refers to the ability to exert power by contraction of muscles, and includes muscular strength which is the ability of the muscles to exhibit maximum contraction to overcome resistance, muscular endurance which is the ability to exhibit how long or how many times muscles may repeat contraction and relaxation at a given weight, and quickness which is the ability to exert strong power in a short time.

In this specification, the term 'improvement of muscle function' refers to improving the muscle function better by increasing the muscle mass, promoting regeneration of damaged muscles, or improving regeneration.

In this specification, the 'promoting the muscle regeneration' means shortening the regeneration or recovery time of damaged muscles, increasing muscle mass by activating the muscles, or lowering the degree of muscle mass loss.

The muscle wasting and degeneration are caused by genetic factors, acquired factors, aging, etc., and the muscle wasting is characterized by a gradual loss of muscle mass, weakness and degeneration of muscles, especially skeletal or voluntary muscle and cardiac muscle, but is not limited to a type of muscle.

In one embodiment, the muscular disorder may be one selected from the group consisting of sarcopenia, atony, muscular atrophy, muscular dystrophy, muscle degeneration, cachexia and myasthenia.

The present disclosure provides a pharmaceutical composition for preventing or treating muscular disorders including a sulfonamide-based compound represented by Chemical Formula 1 or a salt thereof; a food composition for preventing or treating muscular disorders; and a feed composition for preventing or treating muscular disorders:

[Chemical Formula 1]

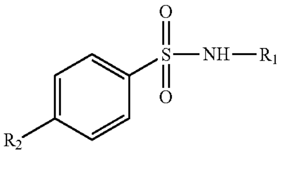

In Chemical Formula 1, $R_1$ is hydrogen, cyamamide, acetyl, or $C_{5-6}$ aryl or heteroaryl, in which $R_1$ is optionally substituted unsubstituted, or substituted with at least one substituent selected from $C_{1-3}$ alkyl, $C_{1-3}$ alkoxy, and phenyl, and $R_2$ is $—NH_2$ or a compound represented by Chemical Formula 1-1 below.

[Chemical Formula 1-1]

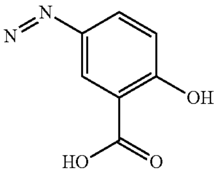

In one embodiment, the hetero element of the hetero aryl may be one or more selected from S, N, and O, one or more hetero elements may be included, and one or more hetero elements different from each other may be included.

In one embodiment, the aryl or heteroaryl may be selected from the group consisting of pyrrole, pyrazole, triazole, oxazole, furan, isoxazole, isothiazole, imidazole, diazole, thiadiazole, phenyl, pyridine, pyrimidine, triazine, oxazine, and thiazine.

In one embodiment, the aryl or heteroaryl may be thiazole, diazole, thiadiazole, phenyl, pyridine or pyrimidine.

In one embodiment, the substituent of $R_1$ may be at least one substituent selected from $C_{1-3}$ alkyl, $C_{1-3}$ alkoxy, and phenyl. In a preferred embodiment, the substituent of $R_1$ may be at least one selected from the group consisting of methyl, ethyl, methoxy, ethoxy and phenyl. One substituent of $R_1$ may be included, and one or more substituents identical to or different from each other may be included.

In one embodiment, the compound of Chemical Formula 1 may be sulfasalazine, sulfamethazine, sulfathiazole, sulfapyridine, sulfaphenazole, sulfameter, sulfamethizole, sulfaguanidine, sulfacetamide sodium, sulfadoxin, sulfadimethoxine, sulfanilamide or sulfadiazine.

In one embodiment, the salt of the compound of the present disclosure includes all kinds of salts commonly accepted in the art of the present disclosure, and may be, for example, a sodium salt.

In one embodiment, the compound of Chemical Formula 1 of the present disclosure acts on PHD20/YY1 to suppress the inhibition of the formation of myoblasts, thereby inhibiting a decrease in muscles in muscle tissues or promoting muscle formation.

As an embodiment, the sulfamethazine of the present disclosure acts on PHD20/YY1 to suppress the inhibition of the formation of myoblasts, thereby inhibiting muscle damage and promoting regeneration, and as a result, it was confirmed in vivo that the balance ability and grip strength recovery of Rota Rod were superior to those of muscle-damaged mice.

When the composition for preventing or treating the muscular disorders of the present disclosure is the pharmaceutical composition, the composition may be used for preventing or treating muscular disorders caused by muscle wasting or degeneration. The muscle wasting and degeneration occur due to genetic factors, acquired factors, aging, etc., and the muscle wasting is characterized by a gradual loss of muscle mass, weakness and degeneration of muscles, especially skeletal or voluntary muscle and cardiac muscle. Examples of related disorders may include sarcopenia, atony, muscular atrophy, muscular dystrophy, muscle degeneration, cachexia and myasthenia, but are not limited thereto. The pharmaceutical composition of the present disclosure may include a pharmaceutically acceptable carrier.

The pharmaceutically acceptable carrier may further include, for example, a carrier for oral administration or a carrier for parenteral administration. The carrier for oral administration may include lactose, starch, cellulose derivatives, magnesium stearate, stearic acid, and the like. In addition, the carrier for parenteral administration may include water, suitable oil, saline, aqueous glucose, glycol, and the like. In addition, a stabilizer and a preservative may be further included. A suitable stabilizer includes antioxidants such as sodium hydrogen sulfite, sodium sulfite or ascorbic acid. A suitable preservative includes benzalkonium chloride, methyl- or propyl-paraben and chlorobutanol.

The pharmaceutical composition of the present disclosure may be administered to mammals including humans even by any method. For example, the pharmaceutical composition may be administered orally or parenterally, and the parenteral administration method is not limited thereto, but may include intravenous, intramuscular, intraarterial, intramedullary, intrathecal, intracardiac, transdermal, subcutaneous, intraperitoneal, intranasal, intestinal, topical, sublingual or rectal administration.

The pharmaceutical composition of the present disclosure may be formulated as formulations for oral administration or parenteral administration according to the route of administration as described above. The formulation may be prepared by using one or more buffers (e.g., saline or PBS), antioxidants, bacteriostatic agents, chelating agents (e.g., EDTA or glutathione), fillers, extenders, binders, adjuvants (e.g., aluminum hydroxide), suspending agents, thickening agents, wetting agents, disintegrants or surfactants, and diluents or excipients.

Solid preparations for oral administration include tablets, pills, powders, granules, liquids, gels, syrups, slurries, suspensions or capsules. These solid preparations may be prepared by mixing at least one excipient, for example, starch (including corn starch, wheat starch, rice starch, potato starch, etc.), calcium carbonate, sucrose, lactose, dextrose, sorbitol, mannitol, xylitol, erythritol maltitol, cellulose, methyl cellulose, sodium carboxymethyl cellulose and hydroxypropyl methyl cellulose or gelatin with the pharmaceutical composition of the present disclosure. For example, tablets or sugar-coated tablets may be obtained by mixing an active ingredient with a solid excipient, pulverizing the mixture, adding a suitable adjuvant, and then processing the mixture into a granule mixture.

Lubricants such as magnesium stearate and talc is also used in addition to simple excipients. Liquid preparations for oral administration may correspond to suspensions, oral liquids, emulsions, syrups, or the like, and may include various excipients, for example, a wetting agent, a sweetener, an aromatic agent, and a preserving agent, in addition to water or liquid paraffin which is a commonly used simple diluent. In addition, in some cases, cross-linked polyvinylpyrrolidone, agar, alginic acid or sodium alginate may be added as a disintegrant, and an anti-coagulant, a lubricant, a wetting agent, a fragrance, an emulsifier, a preservative, and the like may be additionally included.

As one embodiment, when administered parenterally, the pharmaceutical composition of the present disclosure may be formulated according to a method known in the art in the form of injections, transdermal agents, and nasal inhalers together with suitable parenteral carriers. The injections need to be sterilized and protected from contamination of microorganisms such as bacteria and fungi. Examples of suitable carriers for injections are not limited thereto, but may be solvents or dispersion media containing water, ethanol, polyols (e.g., glycerol, propylene glycol, and liquid polyethylene glycols), mixtures thereof and/or vegetable oils. More preferably, as suitable carriers, a Hanks' solution, a Ringer's solution, a phosphate buffered saline (PBS) containing triethanol amine or sterile water for injection, and an isotonic solution such as 10% ethanol, 40% propylene glycol and 5% dextrose may be used. In order to protect the injection from microbial contamination, various antibacterial and antifungal agents such as paraben, chlorobutanol, phenol, sorbic acid, and thimerosal may be further included. In addition, most of the injections may further include an isotonic agent, such as sugar or sodium chloride.

As an example, the transdermal agents are included in the form of ointments, creams, lotions, gels, external liquids, pastas, liniments, and aerosols. Hereinabove, the 'transdermal administration' means that an effective dose of the active ingredient contained in the pharmaceutical composition is delivered into the skin by topically applying the pharmaceutical composition to the skin.

As an example, in the case of the inhalers, the compound used according to the present disclosure may be conveniently delivered in the form of an aerosol spray from a pressurized pack or a nebulizer by using a suitable propellant, for example, dichlorofluoromethane, trichlorofluoromethane, dichlorotetrafluoroethane, and carbon dioxide, or other suitable gases. In the case of a pressurized aerosol, a dosage unit may be determined by providing a valve that delivers a metered amount. For example, gelatin capsules and cartridges used in an inhaler or insufflator may be formulated to contain a powder mixture of a compound and a suitable powder base such as lactose or starch.

The pharmaceutical composition for preventing or treating the muscular disorders of the present disclosure may provide preferred preventive or therapeutic effects on muscular disorders when including an effective dose of the compound of Chemical Formula 1.

In one embodiment, there is provided a method for treating muscular disorders, including administering the compound represented by Chemical Formula 1 or a pharmaceutically acceptable salt thereof to a subject in a therapeutically effective dose.

Preferably, the treatment method may further include identifying a subject in need of prevention or treatment of the muscular disorders before the administering step.

In the present specification, the 'therapeutically effective dose' or 'effective dose' refers to an amount that exhibits a greater response than that of a negative control group, and preferably refers to an amount sufficient to improve muscle function. The pharmaceutical composition of the present disclosure may contain 0.01 to 99.99% of the compound of Chemical Formula 1 or the pharmaceutically acceptable salt thereof, and the remaining amount may account for the pharmaceutically acceptable carrier. The effective dose of the compound of Chemical Formula 1 or the pharmaceutically acceptable salt thereof included in the pharmaceutical composition of the present disclosure may vary depending on a form in which the composition is commercialized.

The total effective dose of the pharmaceutical composition of the present disclosure may be administered to a subject in a single dose, or may be administered to the subject in a multiple dose for a long period of time according to a fractionated treatment protocol. In the pharmaceutical composition of the present disclosure, the content of the active ingredient may vary depending on the severity of disease. In the dosage, an effective dose to the subject may be determined by considering various factors such as the age, weight, health condition, sex, severity of disease, diet and excretion rate of the subject as well as the route of administration of the pharmaceutical composition and the number of treatments. Considering these points, those skilled in the art may determine an appropriate effective dose of the compound of Chemical Formula 1 or the pharmaceutically acceptable salt thereof according to a specific use for preventing or treating muscular disorders. The pharmaceutical composition according to the present disclosure is not particularly limited to the formulation, the administration route, and the administration method thereof, as long as the effects of the present disclosure are shown.

The "subject" may refer to mammals such as human or non-human primates, mice, dogs, cats, horses, and cows, but is not limited thereto.

The pharmaceutical composition for preventing or treating the muscular disorders of the present disclosure may also be provided in a formulation for external use including the compound of Chemical Formula 1 or the pharmaceutically acceptable salt thereof as an active ingredient.

When the pharmaceutical composition of the present disclosure is used as an external skin preparation, the pharmaceutical composition may further contain adjuvants commonly used in the field of dermatology, such as any other ingredients commonly used in external skin preparations, such as fatty substances, organic solvents, solubilizers, concentrate and gelling agents, emollients, antioxidants, suspending agents, stabilizers, foaming agents, fragrances, surfactants, water, ionic emulsifiers, nonionic emulsifiers, fillers, sequestering agents, chelating agents, preservatives, vitamins, blockers, wetting agents, essential oils, dyes, pigments, hydrophilic activators, lipophilic activators or lipid vesicles. In addition, the ingredients may be introduced in an amount generally used in the field of dermatology.

When the pharmaceutical composition of the present disclosure is provided as an external skin preparation, the external skin preparation is not limited thereto, but may be a formulation such as ointments, patches, gels, creams, or sprays.

In another aspect, a composition for preventing or improving muscular disorders of the present disclosure may be a food composition for preventing or improving muscular disorders including a compound of Chemical Formula 1 or a food acceptable salt thereof.

When the composition for preventing or treating the muscular disorders of the present disclosure is the food composition, the composition may be used for preventing or treating muscular disorders caused by muscle wasting or degeneration. The muscle wasting and degeneration occur due to genetic factors, acquired factors, aging, etc., and the muscle wasting is characterized by a gradual loss of muscle mass, weakness and degeneration of muscles, especially skeletal or voluntary muscle and cardiac muscle. Examples of related disorders may include sarcopenia, atony, muscular atrophy, muscular dystrophy, muscle degeneration, cachexia and myasthenia, but are not limited thereto.

As one embodiment, the food composition means including all forms such as functional foods, nutritional supplements, health foods, food additives, or feeds, and is taken for animals including humans or livestock.

The type of food composition may be prepared in various forms according to a general method known in the art. General foods are not limited thereto, but may be prepared by adding the compound of Chemical Formula 1 of the present disclosure or the food acceptable salt thereof to beverages (including alcoholic beverages), fruits and processed foods thereof (e.g., canned fruit, bottled food, jam, and marmalade), fish, meat and processed foods thereof (e.g. ham, sausage, and corned beef), bread and noodles (e.g. udon, buckwheat noodles, ramen, spaghetti, and macaroni), fruit juice, various drinks, cookies, sweets, dairy products (e.g. butter, and cheese), edible vegetable oil, margarine, vegetable proteins, retort food, frozen food, various seasonings (e.g., soybean paste, soy sauce, and sauce), etc. In addition, the nutritional supplements are not limited thereto, but may be prepared by adding the compound of Chemical Formula 1 of the present disclosure or the food acceptable salt thereof to capsules, tablets, pills, etc. In addition, the health functional food is not limited thereto, but for example, may be taken by liquefying, granulating, encapsulating, and powdering so as to be drunken (health beverages) by preparing the compound of Chemical Formula 1 of the present disclosure or the food acceptable salt thereof in the form of tea, juice, and drinks.

In addition, in order to use the compound of Chemical Formula 1 of the present disclosure or the food chemically acceptable salt thereof in the form of food additives, the health functional food may be prepared and used in the form of powders or concentrates. In addition, the health functional food may be prepared in the form of a composition by mixing the compound of Chemical Formula 1 of the present disclosure or the food acceptable salt thereof with known active ingredients known to have an effect of preventing or improving muscular disorders.

When the composition for preventing or improving muscular disorders of the present disclosure is used as a health drink composition, the health drink composition may contain various flavoring agents or natural carbohydrates as an additional ingredient, like a general drink. The natural carbohydrates may be monosaccharides such as glucose and fructose; disaccharides such as maltose and sucrose; polysaccharides such as dextrin and cyclodextrin; and sugar alcohols such as xylitol, sorbitol, and erythritol. As the sweetening agent, natural sweetening agents such as thaumatin and stevia extracts; synthetic sweetening agents such as saccharin and aspartame may be used. A ratio of the natural carbohydrates may be generally about 0.01 to 0.04 g, preferably about 0.02 to 0.03 g per 100 mL of the composition of the present disclosure.

The compound represented by Chemical Formula 1 of the present disclosure or the food acceptable salt thereof may be included as an active ingredient in the food composition for preventing or improving the muscular disorders, but the amount is not particularly limited to an amount effective to achieve an action for preventing or improving muscular disorders, but is preferably 0.01 to 100 wt % based on the total weight of the total composition. The food composition of the present disclosure may be prepared by mixing the compound represented by Chemical Formula 1 or the food acceptable salt thereof with other active ingredients known to be effective in the composition for preventing or improving the muscular disorders.

In addition, the food composition may contain various nutrients, vitamins, electrolytes, flavoring agents, coloring agents, pectic acid and salts thereof, alginic acid and salts thereof, organic acid, protective colloidal thickeners, pH adjusting agents, stabilizers, preservatives, glycerin, alcohol, carbonic acid agents, or the like. In addition, the health food of the present disclosure may contain pulp for preparing natural fruit juice, fruit juice beverage, or vegetable beverage. These ingredients may be used independently or in combination. Although the ratio of these additives is not very important, generally, the ratio thereof is selected in a range of 0.01 to 0.1 part by weight per 100 parts by weight of the composition of the present disclosure.

In yet another aspect, the composition for preventing or improving muscular disorders of the present disclosure may be a feed composition or a feed additive composition for preventing or improving muscular disorders including the compound of Chemical Formula 1.

In the present disclosure, the term 'feed' may mean any natural or artificial diet, one-meal diet, or ingredients of one-meal diet to be eaten, ingested, and digested by animals or suitable therefor. The feed including the composition for preventing or improving the muscular disorders according to the present disclosure as an active ingredient may be prepared with various types of feed known in the art, and preferably, may include concentrated feeds, roughage and/or special feeds, but is not limited thereto.

In the present disclosure, the term 'feed additives' includes substances added to the feeds for the purpose of various effects, such as nutrient supplementation and weight loss prevention, improvement of digestibility of fiber in feed, oil quality improvement, reproduction disorder prevention and conception rate improvement, and summer high temperature stress prevention. The feed additives composition of the present disclosure correspond to supplementary feeds under the Feed Management Act, and may further include mineral preparations such as sodium bicarbonate, bentonite, magnesium oxide, and complex minerals, mineral preparations which are trace minerals such as zinc, copper, cobalt, and selenium, vitamins such as carotene, vitamins A, D, E, nicotinic acid, and vitamin B complex, protected amino acid supplements such as methionine and lysine, protected fatty acid preparations such as fatty acid calcium salts, active bacteria such as probiotics (lactic acid bacteria), yeast cultures, and mold fermented products, yeast agents, and the like.

The concentrated feeds include seed fruits including grains such as wheat, oats and corn, bran including rice bran, wheat bran, and barley bran as by-products obtained by refining grains, residues such as seed cakes which are by-products obtained from oil extraction of beans, oil, sesame, linseed, and coco palms, and residual starches as a main ingredient of starch residues which are the remainder after removing starch from sweet potatoes and potatoes, fish soluble which is a concentrate of fresh liquids obtained from fish meal, fish residues, and fish, animal feeds such as meat meal, blood meal, feather meal, skim milk powder, dried whey, which is obtained by drying whey as the balance when preparing cheese from milk and casein from skim milk, yeast, chlorella, and seaweed, but are not limited thereto.

The roughage includes raw grass feed such as wild grass, grass, and green cutting, root vegetables such as turnips for feed, beets for feed, and Lutherbearer as a type of turnip, silage which is stored feed made by filling a silo with green grass, green crops, and grains, and fermenting the silo with lactic acid, dried hay made by cutting and drying wild grass and grass, straw of breeding crops, and leaves of leguminous plants, but is not limited thereto. The special feed includes mineral feeds such as oyster shells and rock salt, urea feeds such as urea or its derivative, diureideisobutane, feed additives which are substances supplemented with ingredients that tend to be insufficient when only natural feed raw materials are mixed, or added in a small amount to the formulated feed to improve the storage of feeds, and dietary supplements, but is not limited thereto.

The feed additives for preventing or improving the muscular disorders according to the present disclosure may be prepared by adding the compound of Chemical Formula 1 of the present disclosure or the salt thereof in an appropriate effective concentration range according to various feed preparation methods known in the art.

In order to avoid redundant description, the definitions and descriptions of each component of the present disclosure described in Chemical Formula 1 and the pharmaceutical composition section are applied to the food composition and the feed composition as they are, unless otherwise specified.

Hereinafter, exemplary embodiments will be described in detail with reference to the accompanying drawings. However, since various modifications may be made to the exemplary embodiments, the scope of the present disclosure is not limited or restricted by these exemplary embodiments. It should be understood that all modifications, equivalents and substitutes for the exemplary embodiments are included in the scope of the present disclosure.

Example 1. Construction of High Throughput Screening (HTS) System

1-1. Preparation of Cell Line

In order to find a sarcopenia control substance, a high throughput screening (HTS) system was constructed in a cell line capable of easily monitoring a differentiation pattern of muscle cells.

Specifically, a mouse normal myoblast C2C12 cell line was obtained from ATCC (Manassas, VA, USA). C2C12 cells were subcultured every 2 to 3 days in a 100 mm dish containing a DMEM supplemented with 10% fetal bovine serum, 2 mM glutamine, 100 unit/ml penicillin and 100 μg/ml streptomycin (Life Technologies, Grand Island, NY, USA). The cells were cultured and grown under 5% $CO_2$ and 37° C. conditions in a humidified state. While used in experiments, the cells were collected at the end of treatment for additional analysis.

C2C12 myoblasts, which were stable cells in which PHF20 was overexpressed, were transformed with a plasmid coexisting with a YY1 promoter and GFP, which inhibited muscle differentiation, to prepare a stable cell line. The degree of GFP signal suppression was quantified and measured, and the degree of muscle differentiation was used as a quantitative measurement index (FIG. 1).

1-2. Confirmation of PHF20 Expression According to Concentration of Selection Marker In order to construct an HTS system capable of being used as a measurement index of a quantitative measurement system of the degree of muscle differentiation, a stable cell line was selected by treatment with hygromycin, a selection marker for GFP expression, by concentration.

Specifically, C2C12 cell lines transformed with PHF20 and YY1-promoter-GFP plasmid were treated with 150 μg/ml (1 set), 50 μg/ml (2 set) or 250 μg/ml (3 set) of hygromycin together with 1 mg/ml of neomycin and 2 μg/ml of puromycin, respectively, to select only perfectly transformed cell lines. The medium was replaced once every two days, and neomycin, puromycin, and hygromycin were treated at each concentration, and proceeded for about a month.

In addition, C2C12-PHF20/YY1-promoter-GFP cell lines of three types (150 μg/ml (1 set), 50 μg/ml (2 set) or 250 μg/ml (3 set)) selected separately were dispensed in a 96-well white plate in $0.5\times10^5$, cultured for 24 hours, and cells in a 70% confluent state were treated with doxycycline at 0, 50 ng/ml, 250 ng/ml, 500 ng/ml, or 1000 ng/ml, and then cultured for 24 hours. In order to confirm the fluorescence of GFP according to a concentration of doxycycline, the cells were collected and the fluorescence was confirmed using GloMax microplate readers explorer (Promega, Madison, Wisconsin, USA). Extension values were set to 435 to 488 and then measured to quantify the luminescence degree of GFP.

In addition, for Western blot analysis, C2C12 cells were left on ice, washed twice with cold PBS, an then dissolved at 4° C. for 30 minutes in a cell lysis buffer (50 mmol/L Tris-HC1, pH 7.5, 1% (v/v) Nonidet P-40, 250 mmol/L NaCl, 0.1 mmol/L phenyl methyl sulfonyl fluoride, 0.1 mmol/L sodium vanadate, 20 mmol/L β-glycerol phosphate, 2 mmol/L DTT, 1 mmol/L Leupeptin and 10 mmol/L PNPP). Thereafter, the cell lysate was centrifuged at 16,000× g at 4° C. for 20 minutes. The supernatant was collected and used for SDS-PAGE, and the protein content was evaluated by bovine serum albumin protein assay. Proteins were mixed with a sample buffer containing β-mercamptoethanol and heated at 100° C. for 2 minutes. 40 μg of each cell lysate was fractionated by SDS-PAGE on a 10% polyacrylamide gel and transferred to a nitrocellulose membrane. The cell lysate was blocked for 1 hour at room temperature with 5% skim milk dissolved in tri-buffered saline (TBS) containing 0.02% Tween 20, and then reacted overnight at 4° C. with a primary antibody (1:1000 dilution). Actin (1:5000 dilution) was used as a dose control. After the cell lysate was reacted with the primary antibody, before the cell lysate was dissolved in TBS/Tween-20 containing 5% skim milk and reacted for 1 hour at room temperature with goat anti-mouse or anti-rabbit horse radish peroxidase (HRP)-conjugated antibody diluted at 1:2000, blots were washed 4 times in TBS/Tween-20. After washing in TBS/Tween-20, the blots were used for antigen detection using an enhanced chemiluminescence system. Proteins were visualized with an ECL-chemiluminescence kit (GE Healthcare, Life Sciences).

As illustrated in FIGS. 2A and 2B, as a result of confirming using a fluorescence microscope and Western blot analysis in the cell line in Example 1-1, it was confirmed that the luminescence intensity was increased in a doxycycline-dose dependent manner. As a result of comparative analysis by collecting the degree of light luminescence under each condition, the condition of treating 250 μg/ml of hygromycin was the most efficient, and the experiment was performed by fixing the condition of treating 250 ng/ml of doxycycline.

1-3. Confirmation of Effects According to Doxycycline Concentration and Treatment Time The C2C12-PHF20/YY1-promoter-GFP cell line was treated with 50 ng/ml or 250 ng/ml of doxycycline, and after 24 hours, the degree of green luminescence was confirmed through a fluorescence microscope.

In addition, the degree of green luminescence was confirmed using a GloMax microplate readers explorer (Promega, Madison, Wisconsin, USA) after treating the C2C12-PHF20/YY1-promoter-GFP cell line with 250 ng/ml of doxycycline for 12, 24, 36, and 48 hours, respectively.

As a result, as illustrated in FIG. 3, it was confirmed that the degree of luminescence increased as the reaction time increased under a fixed doxycycline concentration condition (250 ng/ml).

Example 2: Screening of Candidate Substances 2-1. Screening of Candidate Substances In order to screen substances using the HTS system constructed in Example 1, an FDA-approved drug library (APExBIO, DiscoveryProbe) was purchased and the degree of GFP inhibition for a total of 1670 compounds was confirmed.

Specifically, the C2C12-PHF20/YY1-promoter-GFP cell line according to Example 1 was dispensed in a 96-well plate at $0.5\times10^5$, cultured for 24 hours, and cells in a 70% confluent state were treated with 250 ng/ml of doxycycline for 24 hours, and then treated with each compound at a final concentration of 10 μM. After 24 hours of compound treatment, the degree of green luminescence was confirmed using GloMax microplate readers explorer (Promega, Madison, Wisconsin, USA).

For fluorescence intensity, C2C12-PHF20/YY1-promoter-GFP cells were dispensed at $4\times10^5$ in a 6-well culture plate and cultured for 24 hours. Then, cells in a 70% confluent state were treated with 250 ng/ml of doxycycline and then after 24 hours, treated with sulfamethazine, ciclopirox, or IOX1 for 24 hours at a final concentration of 10 μM, respectively. Thereafter, the degree of green luminescence was confirmed using GloMax microplate readers explorer (Promega, Madison, Wisconsin, USA).

As a result, 13 kinds of compounds having an effect of reducing green luminescence were derived as candidate substances, in which the compounds included sulfasalazine, sulfamethazine, sulfathiazole, sulfapyridine, sulfaphenazole, sulfameter, sulfamethizole, sulfaguanidine, sulfacetamide sodium, sulfadoxin, sulfadimethoxine, sulfanilamide and sulfadiazine (FIG. 4).

2-2. Quantitative Evaluation of Inhibitory Ability of Myoblast Differentiation Inhibition The effect was confirmed using one of the candidate substances, sulfamethazine. The sulfamethazine was purchased from Sigma (catalog No. S8876) and used, and then dissolved in DMSO at 10 mM and subsequently used in cell experiments.

In order to quantitatively measure the inhibitory ability of myoblast formation inhibition according to a concentration of sulfamethazine, the HTS system constructed in Example 1 was treated with 1 nM, 10 nM, 100 nM, 1 μM or 10 μM of sulfamethazine, respectively, to measure green fluorescence.

As a result, as illustrated in FIG. 6, it was confirmed that the higher the treated concentration of sulfamethazine, the weaker the intensity of fluorescence, which meant that the sulfamethazine acted on PHF20 to inhibit the expression of YY1 that inhibited the formation of myoblasts, and the inhibitory ability was improved in a concentration-dependent manner.

In addition, it was confirmed that the $IC_{50}$ value of sulfamethazine was 0.591 μM based on the green fluorescence intensity obtained in the experiment (FIG. 6).

In addition, the C2C12 muscle cell line was treated with each compound for each concentration for 24 hours, and the expression of proteins PHF20, YY1, and MyoD1 was confirmed by western blotting. In a group treated with each compound, it was confirmed that the protein expression of PHF20 and YY1 decreased, and the expression of MyoD increased (FIG. 7).

2-3. MF 20 (Anti-Myosin) Staining

A sterile coverslip was placed in a 12-well plate, and $1\times10^5$ C2C12/Tet-On PHF20 cells per well were plated and grown at 37° C. The cells were treated with doxycycline for 24 hours. After 24 hours, the cells were differentiated with DM (HS 2%) for 5 days, and at this time, each sulfonamide-based compound was treated for each concentration on day 4 of differentiation. Thereafter, on day 5 of differentiation, the cells were washed twice with PBS at 37° C., reacted in 4% paraformaldehyde for 1 hour, and fixed on the coverslip. Then, the cells were washed twice with PBS. Before blocking, the cells were reacted with Triton x-100 in PBS for 30 minutes. The coverslip was blocked in 1% BSA for 1 hour at room temperature while shaking. An anti-Myosin (MF20) antibody was added to 1% BSA (1:200) and reacted overnight at 4° C. Then, the coverslip was washed three times each with PBS, and an Alexa Fluor 568 secondary antibody (1:1000) in 1% BSA was added, and then reacted at room temperature in the dark for 1 hour while mixing. Thereafter, the coverslip was washed three times with PBS and mounted on a slide using a mounting medium containing DAPI VECTASHIELD (St. Louis, USA), and images of the stained cells were photographed using Zeiss, which were illustrated in FIGS. 8A to 8C.

Specifically, FIG. 8A shows a cellular immunofluorescence staining image for confirming the differentiation ability of muscle cells after differentiation into myotubes from a group of treating a C2C12-PHF20 inducible cell line with doxycyclin to overexpress PHF20 and a control group treated with no doxycyclin, treating drugs (sulfamethazine, sulfatiazole, sulfadiazine, sulfadoxin, sulfadimethoxine, sulfacetamide sodium, sulfaphenazole, and sulfameter) on day 4 of differentiation, and then staining with heavy chain of myosin II (MF20) involved in muscle function and development on day 5 of differentiation.

FIG. 8A shows a cellular immunofluorescence staining image for confirming the differentiation ability of muscle cells when treated with sulfamethazine, sulfatiazole, sulfadiazine, sulfadoxin, sulfadimethoxine, sulfacetamide sodium, sulfaphenazole, and sulfameter, FIG. 8B shows a cellular immunofluorescence staining image for confirming the differentiation ability of muscle cells when treated with sulfamethazine, sulfapyridine, sulfanilamide, and sulfamethizole, and FIG. 8C shows a cellular immunofluorescence staining image for confirming the differentiation ability of muscle cells when treated with sulfasalazine for each concentration.

Example 3: Confirmation of Effect in Aging Mouse Model 3-1. Construction of Aging Mouse Model and Treadmill Adaptation Experiment 32 48-week-old C57BL/6J male mice were obtained from KBSI and then bred under constant room temperature and 12 h night/day cycle for 2 weeks before the experiment, and the mice were fed with a standard rodent diet and freely taken with water.

Treadmill adaptation was performed randomly for 3 days under conditions of grade 0, speed 15 (cm/sec), 10 minutes, electrical stimulation 02 AM (defined as exhaustion when electrical stimulation occurred consecutive 4 times or more), and according to the treadmill result, mice with similar ability were distributed into each group and divided into 4 groups of 8 mice per group.

3-2. Confirmation of Treadmill Exercise Capacity According to Sulfasalazine Dose in Aging Mouse Model In order to confirm the treadmill exercise capacity according to a dose of sulfasalazine, the mice divided in 3-1 above were orally administered at 10:30 every day for 28 days with Group 1 of PBS (Hyclone Dulbecco's Phaosphate Buffer saline Cat. SH30028.02), Group 2 of sulfasalazine (Sigma, Cat. Nr S0883. CAS Number 599-79-1) 5 mpk, Group 3 of sulfasalazine 50 mpk, and Group 4 of sulfasalazine 500 mpk. In order to reduce an error on treadmill exercise ability, the mice were starved for 3 hours before measuring the treadmill, and then the treadmill was performed 4 times at 7-day intervals (0 days, 7 days, 14 days, and 28 days) according to Table 1 below.

TABLE 1

| Grade | Time (min) | Speed (cm/sec) |
|---|---|---|
| 0 | 0~3 | 15 |
| 0 | 3~6 | 20 |
| 0 | 6~9 | 25 |
| 0 | 9~12 | 30 |
| 0 | 12~15 | 35 |
| 0 | 15~18 | 40 |

Electrical stimulation 02 AM
Day 0 before administration, days 7, 14, 21, and 28 after administration
Defined as exhaustion when electric stimulation occurred consecutive 4 or more times For a total of 28 days, the body weight of the mouse was measured, and any change in body weight was confirmed. As shown in FIG. 9, no difference in body weight was observed for each group during the entire experimental period.

As a result of confirming the treadmill exercise capacity, as shown in FIG. 10, it was confirmed that the higher the sulfasalazine dose, the higher the treadmill exercise capacity of the mouse ((*) p≤0.05 vs G1, () p≤0.01 vs G1, (*) p≤0.001 vs G1).

3-3. Confirmation of Recovery of Balance Ability and Grip Strength of Rota Rod According to Sulfasalazine Dose in Aging Mouse Model In order to confirm the balance ability and the grip strength recovery effect of the Rota Rod according to a dose of sulfasalazine, 50-week-old C57BL/6J male mice were divided into Group 1 of PBS, Group 2 of sulfasalazine 5 mg/kg, Group 3 of sulfasalazine 50 mg/kg, and Group 4 of sulfasalazine 500 mg/kg, and orally administered every day at 10 am for 28 days, and then the body weight was measured.

The Rota Rod was measured on days 0, 7, 14, 21, and 28 with the animal group constructed in Group 2 under the conditions shown in Table 2 below, and the results were shown in FIG. 11 ((*) p≤0.05 vs G1). In the same animal group as the Rota Rod, the grip strength was measured on the 2 paws and 4 paws of the mouse on days 0, 9, 16, 23, and 28, and the results were shown in FIGS. 12A and 12B.

TABLE 2

| Constant test | Acceleration |
|---|---|
| 4 rpm in 30 second (mouse standing) | 4-40 rpm in 300 second (until mouse fall down) |

Wash with 50% EtOH
Interval 15 min

As shown in FIGS. 11A and 11B, it was confirmed that as the dose of sulfasalazine increased and the administration day increased, the recovery of balance ability of the mouse on the Rota Rod was improved. In addition, as shown in FIGS. 12A and 12B, in both 2 paws and 4 paws measurement, it was confirmed that the grip strength was improved with the increase in sulfasalazine dose compared to a control group, Group 1, and the grip strength was improved as the administration day was increased.

Example 4: Confirmation of Effect of High-Fat Diet CTX-Induced Sarcopenia Mouse Model 4-1. Construction of High-Fat Diet CTX-Induced Sarcopenia Mouse Model and Confirmation of Body Weight In order to construct a high-fat diet CTX-induced sarcopenia mouse model, for 23-week-old C57BL/6J male mice subjected to 60% HFD for 19 weeks, cardiotoxin (LATOXAN, Portes-lés-Valence, France) was dissolved at 1 mg/ml in PBS to make a high-concentration stock solution. For application to mice, the stock solution was diluted again in PBS (Hyclone Dulbecco's Phaosphate Buffer saline Cat. SH30028.02) to a final concentration of 0.03 mg/ml and used, and intramuscularly injected into both quadriceps muscles of the mouse using a 1 ml syringe (24 G) to construct the high-fat diet CTX-induced sarcopenia mouse model.

Five groups of Group 1 of orally administering PBS to a high-fat diet mouse without injecting CTX, Group 2 of orally administering PBS to a high-fat diet mouse injected with CTX, Group 3 of orally administering sulfasalazine 5 mg/kg to the high-fat diet mouse injected with CTX, Group 4 of orally administering sulfasalazine 50 mg/kg to the high-fat diet mouse injected with CTX, and Group 5 of orally administering sulfasalazine 500 mg/kg to the high-fat diet mouse injected with CTX were divided and orally administered at 10 am every day for 14 days, and the body weights were measured and the results were shown in FIG. 13.

As shown in FIG. 13, no difference in body weight was observed for each group during the entire experimental period.

4-2. Confirmation of Balance Ability and Grip Strength Recovery Ability of Rota Rod in High-Fat Diet CTX-Induced Mouse The measurement before injecting CTX into the sarcopenia mouse constructed in 4-1 above was set as day 0, and on days 4, 8, and 12 after injecting CTX into the muscle, the Rota Rod (Harvard & Panlab, LE8205) was measured under the conditions shown in Table 3 below, and the results were illustrated in FIG. 14. The measurement before injecting CTX into the same animal group as the Rota Rod was set as day 0, and on days 5, 9, and 13, the grip strength was measured with 2 paws and 4 paws of the mouse, and the results were shown in FIGS. 15A and 15B ((*) p≤0.05 vs G2).

TABLE 3

| Constant test | Acceleration |
|---|---|
| 2 rpm in 30 second (mouse standing) | 2-20 rpm in 300 second (until mouse fall down) |

Wash with 50% EtOH
Interval 15 min

As shown in FIG. 14, it was confirmed that as the dose of sulfasalazine increased and the administration day increased as compared to a group injected with CTX, the recovery of balance ability of the mouse on the Rota Rod was improved.

In addition, as shown in FIGS. 15A and 15B, in both 2 paws and 4 paws measurement, it was confirmed that the grip strength was improved with the increase in sulfasalazine dose compared to the group injected with CTX, and the grip strength was improved as the administration day was increased.

Example 5: Confirmation of Effect in Sarcopenia Mouse Model Caused by Velcro Injury 5-1. Construction of Sarcopenia Mouse Model Caused by Velcro Injury The left leg of an 8-week-old C57BL/6J male mouse was anesthetized with isoflurane, the entire leg was wound from the ankle with a 5 cm sports tape, and then wound and fixed with a Velcro with a width of 10 mm, and the Velcro condition was checked every day for 14 days (FIG. 16). Meanwhile, in the present disclosure, Velcro injury means that muscle damage is caused by such Velcro by winding the muscle with the Velcro so as not to move.

5-2. Confirmation of Treadmill Exercise Capacity According to Sulfasalazine Dose in Sarcopenia Mouse Model Caused by Velcro Injury In order to confirm the amount of treadmill exercise according to the dose of sulfasalazine, Group 1 (n=5) of orally administering PBS to 8-week-old C57BL/6J male mice without injury, Group 2 (n=5) of orally administering PBS to mice with Velcro injury, Group 3 (n=5) of orally administering sulfasalazine 5 mg/kg to mice with Velcro injury, Group 4 (n=5) of orally administering sulfasalazine 50 mg/kg to mice with Velcro injury, and Group 5 (n=5) of orally administering sulfasalazine 500 mg/kg to mice with Velcro injury were divided and orally administered at 10 am every day for 14 days, and the body weights were measured and the results were illustrated in FIG. 18. After 14 days, the Velcro was unwound, the treadmill was measured on days 0, 3, 6, 10, and 14, and after fasting for 3 hours before measurement, the mice were warmed up at 15 cm/sec for 2 minutes, and the speed was changed to 25 cm/sec, and then increased to 15 cm/sec every minute until exhaustion (Table 4).

TABLE 4

| Grade (%) | Time (min) | Speed (cm/sec) |
|---|---|---|
| 0 | 0~2 | 15 |
| 0 | 2~3 | 25 |
| 0 | 3~4 | 26 |
| 0 | 4~5 | 27 |
| 0 | 5~6 | 28 |
| 0 | 6~7 | 29 |

Electrical stimulation 02 AM
Inclination 10°
Continue to increase until exhaustion at 1 cm/sec per minute
Day 0 before administration, days 3, 6, 10, and 14 after administration
Defined as exhaustion when electrical stimulation occurred for 5 seconds For a total of 14 days, the body weights of the mice were measured, and any change in body weight was confirmed.

As shown in FIG. 17, no difference in body weight was observed for each group during the entire experimental period.

In order to confirm the treadmill exercise capacity of mice with Velcro injury and mice without Velcro injury, as illustrated in FIG. 18A, as a result of comparing distances run on the treadmill on the first day after unwinding the Velcro, it was confirmed that the mice wound with Velcro were injured with Velcro equally in each group (Group 2 to Group 5) compared to the mice unwound with Velcro (Group 1). As illustrated in FIG. 18B, the same result as the treadmill running distance was confirmed as compared with the treadmill running time.

In addition, as illustrated in FIG. 19A, as a result of comparing the treadmill running distances on the day of unwinding the Velcro, and days 3, 6, 10, and 14, respectively, it was confirmed that the dose of sulfasalazine was high after day 6 of administration compared to a comparative group without winding Velcro, and the treadmill running distances were increased as the administration period was increased.

In addition, as illustrated in FIG. 19B, as a result of comparing the treadmill running distances on the day of unwinding the Velcro, and days 3, 6, 10, and 14, respectively, it was confirmed that the dose of sulfasalazine was high after day 6 of administration compared to a comparative group without winding Velcro, and the treadmill running time was increased as the administration period was increased ((*) p≤0.05, () p≤0.01, (*) p≤0.001).

Example 6: Confirmation of Effect in Sarcopenia Mouse Model 6-1. Confirmation of Muscle Regeneration Effect of CTX-Induced Sarcopenia Mouse Model As experimental animals, 7-week-old male and female C57BL/6J mice with the body weight of 20±3 g were obtained from DooYeol Biotech (Seoul, South Korea).

The mice were bred under constant room temperature and 12 h night/day cycle for 1 week before the experiment, and the mice were fed with a standard rodent diet and were freely taken with water.

In order to construct a CTX-induced sarcopenia mouse model, cardiotoxin (LATOXAN, Portes-les-Valence, France) was dissolved at 1 mg/ml in PBS to make a high-concentration stock solution. To apply to the mice, the stock solution was diluted again in PBS at a final concentration of 0.03 mg/ml and used, and intramuscularly injected into both thigh muscles of the mouse using a 1 ml syringe (24 G) to construct a sarcopenia mouse model.

Thereafter, in an experiment for confirming the effect of the sulfonamide-based compounds of the present disclosure, the efficacy was confirmed using the CTX-induced sarcopenia mouse model.

6-2. Confirmation of Muscle Regeneration Effect of CTX-Induced Sarcopenia Mouse Model 4 μM of sulfamethazine was orally administered to the mouse model of 6-1 (after 24 hours of CTX administration), the muscle tissue was collected from mice on days 3, 6, and 10, and then the degree of muscle differentiation was confirmed by H&E staining.

Specifically, for mouse muscle tissue immunostaining, the muscle tissues of a comparative group and a sulfamethazine-treated group were fixed in 4% paraformaldehyde, washed, and fixed in paraffin. Tissues were cut to a thickness of about 4 mm, fixed to a slide, and then stained using an antibody for each muscle type.

As illustrated in FIG. 20, as a result of confirming the degree of muscle differentiation of the muscle tissue of the mouse through H&E staining, in a control group (a non-sulfamethazine administered group), it was confirmed that the muscle were damaged by CTX, and in a group orally administered with sulfamethazine, it was confirmed that the muscle was regenerated compared to the control group. In particular, after treatment with sulfamethazine, it may be seen that muscle regeneration occurs from day 3, and muscle regeneration occurs quickly on days 6 and 10, and at the same time, the muscles are denser.

6-3. Confirmation of Effect of Sulfamethazine by Muscle Type

In the same manner as in 6-2 above, 4 μM of sulfamethazine was administered to the mouse, and on days 3, 6 and 10, muscle tissue was collected from the mice. In the muscle tissue sample, through antibody staining of each of myosin type I (DSHB BA-75) as dark blue, myosin type IIa (DSHB, BF-F3) as green, and myosin type IIb (DSHB, SC-71) as red, how the recovery of muscle damage was varied for each muscle type by the treatment of sulfamethazine was confirmed using a confocal microscope (Confocal, Leica, Wetzlar, Germany).

As illustrated in FIG. 21, in the sulfamethazine-treated group, compared to the control group, an increase in expressions of green myosin IIa and red myosin IIb was confirmed, and on day 6, the expression of blue-stained myosin I was increased, and the image on day 10 was observed to be recovered similarly to that of a normal control group on day 0. This means that the recovery of muscle damage in the sulfamethazine-administered group is faster than that of a CTX-induced muscle loss mouse (the non-sulfamethazine administered group).

6-4. Confirmation of Balance Ability of Rota Rod According to Dose of Sulfamethazine In order to confirm the balance ability according to a dose of sulfamethazine, 7-week-old male mice were divided into groups of 10 mice to set experimental groups as shown in Table 5, and the experiment was conducted. Specifically, the Rota Rod was measured before CTX injection, and after CTX was injected (day 0), the drug was orally administered once/day for 10 days, and on days 4, 9, and 14, the Rota Rod was measured, respectively. The measurement conditions of the Rota Rod were as shown in FIG. 23.

TABLE 5

| | (−)PBS group | (+)PBS group | 50 mpk group | 100 mpk group | 500 mpk group |
|---|---|---|---|---|---|
| CTX-administration | X | ○ | ○ | ○ | ○ |
| Sulfamethazine | PBS | PBS | 50 mg/kg | 100 mg/kg | 500 mg/kg |

CTX-administration: 0.03 mg/ml, 50 μl injection to each of both hind legs
Administration period of sulfamethazine: For 10 days, once/day, oral administration
Rota Rod measurement: Before CTX injection, and 4 days, 9 days, and 14 days after drug administration
10 mice per each group
Sulfamethazine: Thermo Fisher, Cat. A19276. CAS Number 57-68-1
Administration: DMSO 10% and Cremorphor 12.5% were mixed and then diluted with PBS and administered For a total of 14 days, the body weights of the mice were measured, and any change in body weight was confirmed. As illustrated in FIG. 22, no change in body weight was observed for each group during the entire experimental period, except for a decrease in body weight in all groups on day 10 without diet supply.

As a result of confirming the balance ability of the Rota Rod, as illustrated in FIGS. 24A and 24B, compared to a PBS-administered group ((+)PBS group) after CTX injection, it was confirmed that the higher the dose of sulfamethazine, the higher the balance ability of the Rota Rod of the mouse. In the case of a group without inducing muscle loss ((−)PBS group), the improvement in the balance ability of the Rota Rod according to repeated exercise was observed, but in the case of a sulfametazine-administered group, the balance ability was improved in a dose-dependent manner.

6-5. Confirmation of Grip Strength Recovery According to Dose of Sulfamethazine

In order to confirm the grip strength recovery according to a dose of sulfamethazine, 7-week-old male mice were divided into groups of 10 mice to set experimental groups as shown in Table 6, and the experiment was conducted. Specifically, the grip strength was measured before CTX injection, and after CTX was injected (day 0), the drug was orally administered once/day for 10 days, and on days 4, 9, and 14, the grip strength was measured, respectively.

TABLE 6

| | (−)PBS group | (+)PBS group | 50 mpk group | 100 mpk group | 500 mpk group |
|---|---|---|---|---|---|
| CTX-injection | X | ○ | ○ | ○ | ○ |
| Sulfamethazine | PBS | PBS | 50 mg/kg | 100 mg/kg | 500 mg/kg |

CTX-administration: 0.03 mg/ml, 50 μl injection to each of both hind legs
Administration period of sulfamethazine: For 10 days, once/day, oral administration
Rota Rod measurement: Before CTX injection, and 4 days, 9 days, and 14 days after drug administration
10 mice per each group
Sulfamethazine: Thermo Fisher, Cat. A19276. CAS Number 57-68-1
Administration: DMSO 10% and Cremorphor 12.5% were mixed and then diluted with PBS and administered For a total of 14 days, the body weights of the mice were measured, and any change in body weight was confirmed. As illustrated in FIG. 22, no change in body weight was observed for each group during the entire experimental period, except for a decrease in body weight in all groups on day 10 without diet supply.

As a result of confirming the grip strength recovery effect, as shown in FIGS. 26A to 26D, for the exercise capacity of the hind legs (2 paws) injected with CTX, compared to the PBS-administered group ((+)PBS group) after CTX injection, it was confirmed that the grip strength of mice increased as the dose of sulfamethazine increased. As a result of measuring the grip strength of all four paws, it was also showed that the grip strength was increased in a sulfamethazine concentration-dependent manner. Similarly to the group ((−)PBS group) without inducing muscle loss on the Rota Rod, which had showed a repeated level of improvement in balance ability, even in the grip strength, it was confirmed that the grip strength recovery was improved in a dose-dependent manner in the sulfamethazine-administered group.

Example 7: Confirmation of Toxicity of Single Oral Dose 7-1. Confirmation of Toxicity of Single Oral Dose 7-week-old male and female C57BL/6J mice with the body weight of 20±3 g were obtained from DooYeol Biotech (Seoul, South Korea). The mice were bred under constant room temperature and 12 h night/day cycle for 1 week before the experiment, and the mice were fed with a standard rodent diet and were freely taken with water. The experiment was conducted by dividing the mice into a control group and test groups (100 mg/kg, 500 mg/kg, and 1000 mg/kg), and sulfamethazine was diluted with 12.5% DMSO and 12.5% cremophor and orally administered at 10 ml/kg.

Control group: PBS (without administration of sulfamethazine)

Group 1: 100 mg/kg (experimental group, administration of sulfamethazine)

Group 2: 500 mg/kg (experimental group, administration of sulfamethazine)

Group 3: 1,000 mg/kg (experimental group, administration of sulfamethazine)

The experiment was conducted for 2 weeks, and the general condition and the presence or absence of death were observed at least once a day. The body weights were measured before administration, and on 1 day, 3 days, 7 days, and 14 days after administration, and an autopsy was performed on day 14.

In the present disclosure, a single oral dose toxicity test refers to a test that qualitatively and quantitatively examines toxicity in a short period of time when a test substance was administered to test animals in a single dose (including divided doses within 24 hours).

Specifically, FIG. 27A shows all mice for confirming toxicity according to single oral administration of female and male mice, FIG. 27B shows photographs of male mice before organ harvesting, and FIG. 27C shows photographs of female mice before organ harvesting.

In addition, all organs of the head, the thoracic cavity, and the abdominal cavity were observed, which were shown in FIGS. 28A to 39.

Specifically, FIG. 28A is a photograph confirming toxicity by dissecting the livers of male mice, FIG. 28B is a photograph confirming toxicity by dissecting the livers of female mice, FIG. 29A is a photograph confirming toxicity by dissecting the lungs of male mice, and FIG. 29B is a photograph confirming toxicity by dissecting the lungs of female mice. FIG. 30 is a photograph of confirming toxicity by dissecting the brains of male and female mice, FIG. 31 is a photograph of confirming toxicity by dissecting the hearts of male and female mice, FIG. 32 is a photograph of confirming toxicity by dissecting the stomachs of male and female mice, FIG. 33 is a photograph of confirming toxicity by dissecting the pancreases of male and female mice, and FIG. 34 is a photograph of confirming toxicity by dissecting the spleens of male and female mice. FIG. 35A is a photograph of confirming toxicity by dissecting the kidneys of male mice, FIG. 35B is a photograph of confirming toxicity by dissecting the kidneys of female mice, FIG. 36A is a photograph of confirming toxicity by dissecting the S. intestines of male mice, and FIG. 36B is a photograph of confirming toxicity by dissecting the S. intestines of female mice. FIG. 37A is a photograph of confirming toxicity by dissecting the L. intestines of male mice, FIG. 37B is a photograph of confirming toxicity by dissecting the L. intestines of female mice, FIG. 38 is a photograph of confirming toxicity by dissecting the testis of male mice, and FIG. 39 is a photograph of confirming toxicity by dissecting the wombs of female mice.

In addition, after oral administration of the PBS or sulfamethazine, the results of measuring the body weights of male mice and female mice in each group on days 1, 3, 7 or 14 were shown in FIG. 40, the results of measuring the weight of each tissue of each male mouse on day 14 were shown in FIG. 41A, and the results of measuring the weight of each tissue of each female mouse on day 14 were shown in FIG. 41B. There was no singularity in tissue weight for each group, and it was confirmed that the decrease in pancreas weights of females in the 500 mpk group was caused by the loss of some tissues during dissection.

7-2. Histochemical Evaluation of Toxicity by Single Oral Administration

As in Example 7-1, mice with single oral administration were dissected on day 14 after administration, and histochemical toxicity was evaluated. The pathology of the liver was observed through H&E staining on the dissected liver tissue.

As shown in FIGS. 42A and 42B, no specific pathological findings were observed between each group, similarly to the fact that the toxicity was not confirmed in the harvested livers of male and female mice.

7-3. Confirmation of Blood Liver Toxicity, Heart Toxicity, and Kidney Toxicity

In mice orally administered once as in Experimental Example 7-1, blood was collected from the heart of the mouse on day 14 after administration, and serum was collected to confirm the expression of a liver toxicity marker, a heart toxicity marker, and a kidney toxicity marker, respectively. Specifically, blood samples were collected from the heart after surgery on day 14 after administration of sulfamethazine. The collected blood was left at room temperature for 1 hour to be coagulated, and the serum was isolated by operating a centrifuge (13,000 rpm) for 20 minutes. Blood analysis was performed by dividing liver toxicity, heart toxicity, and kidney toxicity, and the analysis was conducted by requesting DooYeol Biotech (Seoul, Korea).

As a result, as shown in FIGS. 43A and 43B, no specific phenomena related to liver toxicity, heart toxicity, and kidney toxicity in male and female mice were observed in the sulfamethazine-administered group.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method for preventing inhibition of myoblast differentiation comprising administering to a subject in need thereof, a therapeutically effective amount of a composition comprising one or more of sulfonamide-based compounds of Chemical Formula 1 below or a pharmaceutically acceptable salt thereof to decrease the expression of PHF20 and YY1:

[Chemical Formula 1]

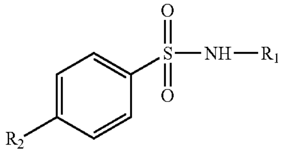

wherein $R_1$ is hydrogen, $C(=N)NH_2$, acetyl, or $C_{5-6}$ aryl or heteroaryl, wherein $R_1$ is optionally substituted with at least one substituent selected from the group consisting of $C_{1-3}$ alkyl, $C_{1-3}$ alkoxy, and phenyl, and $R_2$ is $-NH_2$ or

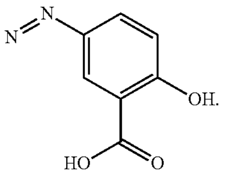 [SMILES: N=Nc1ccc(O)c(C(=O)O)c1]

2. The method of claim 1, wherein the aryl or heteroaryl includes thiazole, diazole, thiadiazole, phenyl, pyridine or pyrimidine, and the aryl or heteroaryl is optionally substituted with at least one substituent selected from the group consisting of $C_{1-3}$ alkyl, $C_{1-3}$ alkoxy, and phenyl.

3. The method of claim 1, wherein the at least one substituent selected from the group consisting of $C_{1-3}$ alkyl and $C_{1-3}$ alkoxy is methyl or methoxy.

4. The method of claim 1, wherein the sulfonaminde-based compound is selected from the group consisting of sulfasalazine, sulfamethazine, sulfathiazole, sulfapyridine, sulfaphenazole, sulfameter, sulfamethizole, sulfaguanidine, sulfacetamide, sulfadoxine, sulfadimethoxine, sulfanilamide, and sulfadiazine.

5. The method of claim 1, wherein the composition is a pharmaceutical composition or a food composition.

6. The method of claim 1, wherein the subject is a human.

* * * * *